(12) United States Patent
Binggeli et al.

(10) Patent No.: US 7,109,225 B2
(45) Date of Patent: Sep. 19, 2006

(54) SUBSTITUTED OXAZOLE DERIVATIVES

(75) Inventors: Alfred Binggeli, Binningen (CH); Uwe Grether, Loerrach (DE); Hans Hilpert, Muenchenstein (CH); Georges Hirth, Huningue (FR); Hans-Peter Maerki, Basel (CH); Markus Meyer, Neuenburg (DE); Peter Mohr, Basel (CH)

(73) Assignee: Hofmann-la Roche Inc., Nutley, NJ (US)

( * ) Notice: Subject to any disclaimer, the term of this patent is extended or adjusted under 35 U.S.C. 154(b) by 0 days.

(21) Appl. No.: 10/700,417

(22) Filed: Nov. 4, 2003

(65) Prior Publication Data
US 2004/0157898 A1 Aug. 12, 2004

(30) Foreign Application Priority Data
Nov. 8, 2002 (EP) .................. 02025001

(51) Int. Cl.
*A61K 31/421* (2006.01)
*A61K 31/422* (2006.01)
*C07D 263/32* (2006.01)

(52) U.S. Cl. ..................... 514/374; 548/235
(58) Field of Classification Search ............... 548/235; 514/374
See application file for complete search history.

(56) References Cited
FOREIGN PATENT DOCUMENTS

| WO | WO 91/19702 | 12/1991 |
| WO | WO 98/57636 | 12/1998 |
| WO | WO 00/66572 | 11/2000 |
| WO | WO 02/16331 | 2/2002 |
| WO | WO 02/16332 | 2/2002 |

OTHER PUBLICATIONS

Keller et al., Trends Endocrin. Metab., 4, pp. 291-296 (1993).
MacDougald et al., Current Biology, 5, pp. 618-621 (1995).
Guerre-Millo et al., J. Biol. Chem., 275, pp. 16638-16642 (2000).
Balfour et al., Drugs, 57, pp. 921-930 (1999).

*Primary Examiner*—Laura L. Stockton
(74) *Attorney, Agent, or Firm*—George W. Johnston; Patricia S. Rocha-Tramaloni; Brian C. Remy

(57) ABSTRACT

The present invention relates to compounds of formula (I)

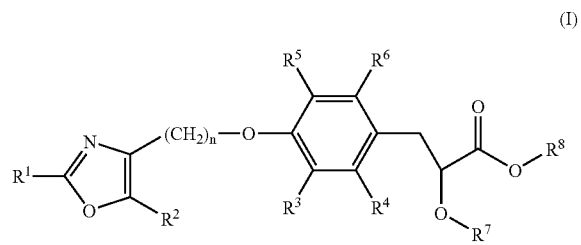

wherein $R^1$ to $R^8$ and n are as defined in the description and claims, and pharmaceutically acceptable salts and esters thereof. The compounds are useful for the treatment of diseases such as diabetes.

53 Claims, No Drawings

SUBSTITUTED OXAZOLE DERIVATIVES

BACKGROUND OF THE INVENTION

The present invention is concerned with novel substituted oxazole derivatives, their manufacture and their use as medicaments.

Peroxisome Proliferator Activated Receptors (PPAR's) are members of the nuclear hormone receptor super family, which are ligand-activated transcription factors regulating gene expression. Various subtypes thereof have been identified and cloned. These include PPARα, PPARβ (also known as PPARδ), and PPARγ. There exist at least two major isoforms of PPARγ. While PPARγ1 is ubiquitously expressed in most tissues, the longer isoform PPARγ2 is almost exclusively found in adipocytes. In contrast, PPARα is predominantly expressed in the liver, kidney and heart. PPAR's modulate a variety of body responses including glucose- and lipid-homeostasis, cell differentiation, inflammatory responses and cardiovascular events.

Diabetes is a disease in which a patient's ability to control glucose levels in blood is impaired, because he has partially lost the ability to respond properly to the action of insulin. In type II diabetes (T2D), often referred to as non-insulin dependent diabetes mellitus (NIDDM), which afflicts 80–90% of all diabetic patients in developed countries, the Isles of Langerhans in the pancreas still produce insulin. However, the target organs, mainly muscle, liver and adipose tissue, exhibit a profound resistance to insulin stimulation, and the body compensates by producing unphysiologically high levels of insulin. In later stage of disease, however, insulin secretion decreases due to exhaustion of the pancreas. In addition to that T2D is a metabolic-cardiovascular disease syndrome. Among the comorbidities associated with T2D are for example insulin resistance, dyslipidemia, hypertension, endothelial dysfunction and inflammatory atherosclerosis.

Current first line treatment for diabetes generally involves low fat—and glucose—diet and exercise. However, compliance can be moderate and as the disease progresses, treatment with hypoglycemic drugs, e.g. sulfonylureas or metformin, becomes necessary. A promising new class of drugs has recently been introduced that resensitizes patients to their own insulin (insulin sensitizers), thereby reverting blood glucose and triglyceride levels to normal, and thus abolishing, or at least reducing, the requirement for exogenous insulin. Pioglitazone (Actos™) and rosiglitazone (Avandia™) belong to the thiazolidinediones (TZD) class of PPARγ-agonists and were the first representatives who had been approved for NIDDM in several countries. These compounds, however, suffer from side effects including rare but severe liver toxicity (as seen with troglitazone), and they increase body weight in humans. Therefore, new, better and more efficacious drugs for the treatment of NIDDM are urgently needed. Recent studies provide evidence that a coagonism on PPARα and PPARγ would result in compounds with enhanced therapeutic potential, i.e. such compounds should improve the lipid profile in addition to the normalization of glucose- and insulin-levels (Keller and Wahli: Trends Endocrin. Metab. 1993; 4:291–296, Macdonald and Lane: Current Biology Vol. 5 pp. 618–621 (1995)). Recent observations suggest furthermore that there is an independent PPARα mediated effect on insulin-sensitzation that could result secondary to the reduction in lipids (Guerre-Millo et al; J Biol Chem2000; 275: 16638–16642). Consequently, the incorporation of PPARα activity into PPARγ agonists is expected to give rise to more efficacious drugs for the treatment and/or prevention of diabetes.

The novel compounds of the present invention exceed the compounds known in the art, inasmuch as they bind to and activate both, PPARα and PPARγ, simultaneously and very efficiently. Therefore, these compounds combine the anti-glycemic effect of PPARγ activation with the anti-dyslipidemic effect of PPARα activation. Consequently, plasma glucose and insulin are reduced (=insulin sensitization), triglycerides lowered and HDL cholesterol increased (=improved lipid profile). In addition, such compounds may also lower LDL cholesterol, decrease blood pressure and counteract inflammatory atherosclerosis. Since multiple facets of the T2D disease syndrome are addressed by PPARα and γ coagonists, they are expected to have an enhanced therapeutic potential compared to the compounds already known in the art.

SUMMARY OF THE INVENTION

The present invention relates to compounds of the formula (I)

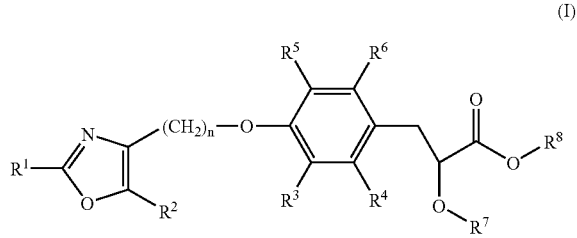

wherein $R^1$, $R^2$, $R^3$, $R^4$, $R^5$, $R^6$, $R^7$, $R^8$ and n are as defined herein, or pharmaceutically acceptable salts or pharmaceutically acceptable esters thereof.

The compounds of the present invention further exhibit improved pharmacological properties compared to known compounds.

Unless otherwise indicated the following definitions are set forth to illustrate and define the meaning and scope of the various terms used to describe the invention herein.

In this specification the term "lower" is used to mean a group consisting of one to seven, preferably of one to four carbon atom(s).

The term "halogen" refers to fluorine, chlorine, bromine and iodine.

The term "protecting group" refers to groups such as e.g. acyl, alkoxycarbonyl, aryloxycarbonyl, silyl, or imine-derivatives, which are used to temporarily block the reactivity of functional groups. Well known protecting groups are e.g. t-butyloxycarbonyl, benzyloxycarbonyl, fluorenylmethyloxycarbonyl or diphenylmethylene which can be used for the protection of amino groups, or lower-alkyl-, β-trimethylsilylethyl- and β-trichloroethyl-esters, which can be used for the protection of carboxy groups.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like.

The term "fluoro-lower-alkyl" refers to lower-alkyl groups which are mono- or multiply substituted with fluorine, preferably with up to 6 fluorine atoms. Examples of fluoro-lower-alkyl groups are e.g. $CF_3$, $CF_3CH_2$ and $(CF_3)_2CH$.

The term "alkoxy" refers to the group R'—O—, wherein R' is alkyl. The term "lower-alkoxy" refers to the group R'—O—, wherein R' is lower-alkyl. Examples of lower-alkoxy groups are e.g. methoxy, ethoxy, propoxy, isopropoxy, butoxy, isobutoxy and hexyloxy.

The term "fluoro-lower-alkoxy" refers to the group R"—O—, wherein R" is fluoro-lower-alkyl. Examples of fluoro-lower-alkoxy groups are e.g. $CF_3$—O, $CF_3CH_2$—O and $(CF_3)_2CH$—O.

The term "lower-alkenyl", alone or in combination, signifies a straight-chain or branched hydrocarbon residue comprising an olefinic bond and 2 to 8, preferably 2 to 6, particularly preferred 2 to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl.

The term "cycloalkyl" refers to a monovalent carbocyclic radical of 3 to 10 carbon atoms, preferably 3 to 6 carbon atoms, such as cyclopropyl, cyclobutyl, cyclopentyl, or cyclohexyl. A cycloalkyl group can optionally be substituted with lower-alkyl. Unsubstituted cycloalkyl groups are preferred.

The term "bicyclic cycloalkyl" refers to a monovalent radical of 8 to 12 carbon atoms which comprises two fused or bridged cycloalkyl groups, such as hexahydroindanyl, decalinyl, or norbornanyl. A bicyclic cycloalkyl group can optionally be substituted with lower-alkyl. Unsubstituted bicyclic cycloalkyl groups are preferred.

The term "tricyclic cycloalkyl" refers to a monovalent radical of 10 to 13 carbon atoms which comprises three fused or bridged cycloalkyl groups, such as adamantyl. A tricyclic cycloalkyl group can optionally be substituted with lower-alkyl. Unsubstituted tricyclic cycloalkyl groups are preferred.

The term "aryl" relates to the phenyl or naphthyl group, preferably the phenyl group, which can optionally be mono- or multiply-substituted, particularly mono- or di-substituted by halogen, hydroxy, CN, $CF_3$, $NO_2$, $NH_2$, N(H, lower-alkyl), N(lower-alkyl)$_2$, carboxy, aminocarbonyl, lower-alkyl, lower-alkoxy, phenyl and/or phenyloxy. Preferred substituents are halogen, $CF_3$, lower-alkyl and/or lower-alkoxy.

The term "pharmaceutically acceptable salts" embraces salts of the compounds of formula (I) with pharmaceutically acceptable bases such as alkali salts, e.g. Na- and K-salts, alkaline earth salts, e.g. Ca- and Mg-salts, and ammonium or substituted ammonium salts, such as e.g. trimethylammonium salts. The term "pharmaceutically acceptable salts" also relates to such salts.

The compounds of formula (I) can also be solvated, e.g. hydrated. The solvation can be effected in the course of the manufacturing process or can take place e.g. as a consequence of hygroscopic properties of an initially anhydrous compound of formula (I) (hydration). The term pharmaceutically acceptable salts also includes pharmaceutically acceptable solvates.

The term "pharmaceutically acceptable esters" embraces derivatives of the compounds of formula (I), in which a carboxy group has been converted to an ester. Lower-alkyl, hydroxy-lower-alkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. The methyl, ethyl, propyl, butyl and benzyl esters are preferred esters. The methyl and ethyl esters are especially preferred. The term "pharmaceutically acceptable esters" furthermore embraces compounds of formula (I) in which hydroxy groups have been converted to the corresponding esters with inorganic or organic acids such as nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

DETAILED DESCRIPTION OF THE INVENTION

In detail, the present invention relates to compounds of formula (I)

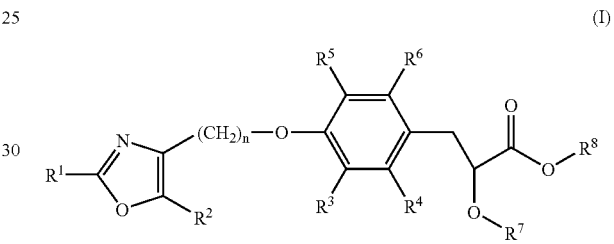

wherein $R^1$ is alkyl, fluoro-lower-alkyl, cycloalkyl, bicyclic cycloalkyl, or tricyclic cycloalkyl;

$R^2$ is hydrogen, lower-alkyl, or fluoro-lower-alkyl;

$R^3$, $R^4$, $R^5$, and $R^6$ are independently selected from the group consisting of hydrogen, hydroxy, halogen, lower-alkyl, fluoro-lower-alkyl, hydroxy-lower-alkyl, lower-alkoxy-lower-alkyl, lower-alkoxy, fluoro-lower-alkoxy, hydroxy-lower-alkoxy, lower-alkoxy-lower-alkoxy, and lower-alkenyl, wherein at least one of $R^3$, $R^4$, $R^5$, or $R^6$ is not hydrogen, or $R^3$ and $R^4$ are bonded to each other to form a ring together with the carbon atoms to which they are attached, and $R^3$ and $R^4$ together are —CH=CH—S—, —S—CH=CH—, —CH=CH—O—, —O—CH=CH—, —CH=CH—CH=CH—, —O—(CH$_2$)$_{2-3}$—, —(CH$_2$)$_{2-3}$—O—, or —(CH$_2$)$_{3-5}$—, and $R^5$ and $R^6$ are as defined above, $R^7$ is lower-alkyl, fluoro-lower-alkyl, lower-alkenyl, aryl, or aryl-lower-alkyl;

$R^8$ is hydrogen or lower-alkyl;

n is 1, 2 or 3;

or pharmaceutically acceptable salts or pharmaceutically acceptable esters thereof.

Preferred compounds of the present invention are those, in which $R^1$ is lower-alkyl, fluoro-lower-alkyl, cycloalkyl, bicyclic cycloalkyl, or tricyclic cycloalkyl. Compounds, in which $R^1$ is lower-alkyl or cycloalkyl are more preferred and most preferably $R^1$ is t-butyl, 2,2-dimethyl-propyl, cyclopropyl, or cyclohexyl. If $R^1$ is alkyl, an alkyl group with 1 to 10 carbon atoms is preferred. In another preferred embodiment of the present invention, $R^2$ is lower-alkyl, more preferably methyl.

Furthermore, compounds of formula (I) as defined above, wherein $R^3$, $R^4$, $R^5$, and $R^6$ independently from each other are hydrogen, halogen, lower-alkyl, or lower-alkoxy, wherein at least one of $R^3$, $R^4$, $R^5$, or $R^6$ is not hydrogen; or $R^3$ and $R^4$ are bonded to each other to form a ring together with the carbon atoms to which they are attached, and $R^3$ and $R^4$ together are —CH=CH—S— or —CH=CH—CH=CH—, and $R^5$ and $R^6$ are hydrogen are also preferred. Compounds as defined above, wherein $R^3$, $R^4$, $R^5$, and $R^6$ independently from each other are hydrogen or lower-alkyl, wherein at least one of $R^3$, $R^4$, $R^5$, or $R^6$ is not hydrogen, are also preferred, particularly those, wherein $R^3$, $R^4$, $R^5$, and $R^6$ independently from each other are hydrogen or methyl, wherein at least one of $R^3$, $R^4$, $R^5$, or $R^6$ is not hydrogen.

Another preferred embodiment of the present invention relates to compounds of formula (I) wherein R and $R^4$ are bonded to each other to form a ring together with the carbon atoms to which they are attached, and $R^3$ and $R^4$ together are —CH=CH—S— or —CH=CH—CH=CH—, and $R^5$ and $R^6$ are hydrogen. Such compounds are consequently of the formula (Ia) or formula (Ib) respectively.

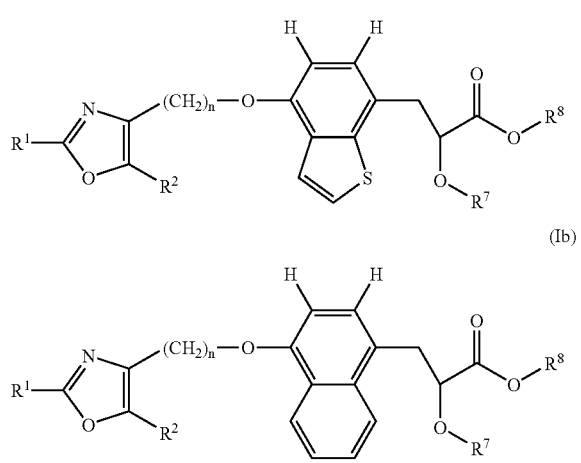

Further preferred compounds of formula (I) are those, wherein $R^7$ is lower-alkyl or lower-alkenyl, particularly ethyl, n-propyl, i-propyl, or but-3-enyl. Also preferred are compounds of formula (I), wherein $R^8$ is hydrogen. Also preferred are compounds of formula (I), wherein n is 1 or 2, more preferably 2.

The pharmaceutically acceptable salts of the compound of formula (I) and the pharmaceutically acceptable esters of the compounds of formula (I) individually constitute preferred embodiments of the present invention. Particularly preferred are compounds of formula (I).

Furthermore, the S-enantiomers of the compounds of the present invention relate to a preferred embodiment. Therefore, compounds of formula (Ic)

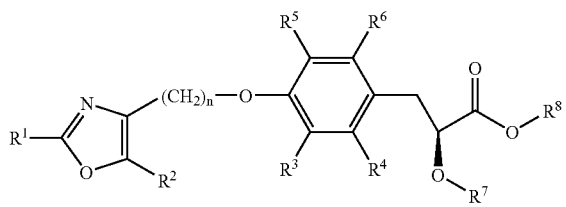

wherein $R^1$, $R^2$, $R^3$, $R^4$, $R^5$, $R^6$, $R^7$, $R^8$ and n are as defined as before, are also preferred.

Preferred compounds of general formula (I) are those selected from the group consisting of (S)-3-{4-[2-(2-tert-Butyl-5-methyl-oxazol-4-yl)-ethoxy]-naphthalen-1-yl}-2-ethoxy-propionic acid, (S)-2-But-3-enyloxy-3-{4-[2-(2-tert-butyl-5-methyl-oxazol-4-yl)-ethoxy]-naphthalen-1-yl}-propionic acid, (S)-3-{4-[2-(2-tert-Butyl-5-methyl-oxazol-4-yl)-ethoxy]-3,5-dimethyl-phenyl}-2-ethoxy-propionic acid, (S)-3-{4-[2-(2-tert-Butyl-5-methyl-oxazol-4-yl)-ethoxy]-3,5-dimethyl-phenyl}-2-propoxy-propionic acid, (S)-3-{4-[2-(2-tert-Butyl-5-methyl-oxazol-4-yl)-ethoxy]-3,5-dimethyl-phenyl}-2-isopropoxy-propionic acid, (S)-3-{4-[2-(2-tert-Butyl-5-methyl-oxazol-4-yl)-ethoxy]-benzo[b]thiophen-7-yl}-2-ethoxy-propionic acid, (S)-2-But-3-enyloxy-3-{4-[2-(2-tert-butyl-5-methyl-oxazol-4-yl)-ethoxy]-benzo[b]thiophen-7-yl}-propionic acid, 3-{4-[2-(2-tert-Butyl-5-methyl-oxazol-4-yl)-ethoxy]-benzo[b]thiophen-7-yl}-2-isopropoxy-propionic acid, 3-{4-[2-(2-tert-Butyl-5-methyl-oxazol-4-yl)-ethoxy]-benzo[b]thiophen-7-yl}-2-ethoxy-propionic acid, 3-{4-[2-(2-tert-Butyl-5-methyl-oxazol-4-yl)-ethoxy]-benzo[b]thiophen-7-yl}-2-methoxy-propionic acid, 3-{4-[2-(2-tert-Butyl-5-methyl-oxazol-4-yl)-ethoxy]-naphthalen-1-yl}-2-isopropoxy-propionic acid, 3-{4-[2-(2-tert-Butyl-5-methyl-oxazol-4-yl)-ethoxy]-naphthalen-1-yl}-2-ethoxy-propionic acid, 3-{4-[2-(2-tert-Butyl-5-methyl-oxazol-4-yl)-ethoxy]-naphthalen-1-yl}-2-methoxy-propionic acid, 3-{4-[2-(2-tert-Butyl-5-methyl-oxazol-4-yl)-ethoxy]-naphthalen-1-yl}-2-propoxy-propionic acid, 3-{4-[2-(2-tert-Butyl-5-methyl-oxazol-4-yl)-ethoxy]-3,5-dimethyl-phenyl}-2-methoxy-propionic acid, 3-{4-[2-(2-tert-Butyl-5-methyl-oxazol-4-yl)-ethoxy]-3,5-dimethyl-phenyl}-2-ethoxy-propionic acid, 3-{4-[2-(2-tert-Butyl-5-methyl-oxazol-4-yl)-ethoxy]-3-methyl-phenyl}-2-ethoxy-propionic acid, 3-{4-[2-(2-tert-Butyl-5-methyl-oxazol-4-yl)-ethoxy]-3-methyl-phenyl}-2-isopropoxy-propionic acid, 3-[4-(2-tert-Butyl-5-methyl-oxazol-4-ylmethoxy)-benzo[b]thiophen-7-yl]-2-ethoxy-propionic acid, 3-[4-(2-tert-Butyl-5-methyl-oxazol-4-ylmethoxy)-3,5-dimethyl-phenyl]-2-ethoxy-propionic acid, 3-[4-(2-tert-Butyl-5-methyl-oxazol-4-ylmethoxy)-3-methyl-phenyl]-2-ethoxy-propionic acid, 3-[4-(2-tert-Butyl-5-methyl-oxazol-4-ylmethoxy)-naphthalen-1-yl]-2-ethoxy-propionic acid, 3-[4-(2-tert-Butyl-5-methyl-oxazol-4-ylmethoxy)-benzo[b]thiophen-7-yl]-2-isopropoxy-propionic acid, 3-[4-(2-tert-Butyl-5-methyl-oxazol-4-ylmethoxy)-naphtha-
len-1-yl]-2-propoxy-propionic acid,
3-{4-[2-(2-Cyclohexyl-5-methyl-oxazol-4-yl)-ethoxy]-3,5-
dimethyl-phenyl}-2-isopropoxy-propionic acid,
3-{4-[2-(2-Cyclohexyl-5-methyl-oxazol-4-yl)-ethoxy]-3,5-
dimethyl-phenyl}-2-ethoxy-propionic acid,
3-{4-[2-(2-Cyclohexyl-5-methyl-oxazol-4-yl)-ethoxy]-
naphthalen-1-yl}-2-ethoxy-propionic acid,
3-{4-[2-(2-Cyclohexyl-5-methyl-oxazol-4-yl)-ethoxy]-
naphthalen-1-yl}-2-propoxy-propionic acid,
3-{4-[2-(2-Cyclopropyl-5-methyl-oxazol-4-yl)-ethoxy]-
naphthalen-1-yl}-2-isopropoxy-propionic acid,
3-{4-[2-(2-Cyclopropyl-5-methyl-oxazol-4-yl)-ethoxy]-
naphthalen-1-yl}-2-ethoxy-propionic acid,
3-{4-[2-(2-Cyclopropyl-5-methyl-oxazol-4-yl)-ethoxy]-
benzo[b]thiophen-7-yl}-2-propoxy-propionic acid,
3-{4-[2-(2-Cyclopropyl-5-methyl-oxazol-4-yl)-ethoxy]-
benzo[b]thiophen-7-yl}-2-ethoxy-propionic acid,
3-(4-{2-[2-(2,2-Dimethyl-propyl)-5-methyl-oxazol-4-yl]-
ethoxy}-naphthalen-1-yl)-2-propoxy-propionic acid,
3-(4-{2-[2-(2,2-Dimethyl-propyl)-5-methyl-oxazol-4-yl]-
ethoxy}-naphthalen-1-yl)-2-ethoxy-propionic acid,
3-{4-[2-(2-tert-Butyl-5-ethyl-oxazol-4-yl)-ethoxy]-benzo
[b]thiophen-7-yl}-2-ethoxy-propionic acid,
3-(4-{2-[2-(2,2-Dimethyl-propyl)-5-methyl-oxazol-4-yl]-
ethoxy}-benzo[b]thiophen-7-yl)-2-ethoxy-propionic
acid,
3-(4-{2-[2-(2,2-Dimethyl-propyl)-5-methyl-oxazol-4-yl]-
ethoxy}-benzo[b]thiophen-7-yl)-2-isopropoxy-propionic
acid,
3-[4-(2-Cyclopropyl-5-methyl-oxazol-4-ylmethoxy)-naph-
thalen-1-yl]-2-ethoxy-propionic acid,
3-[4-(2-Cyclopropyl-5-methyl-oxazol-4-ylmethoxy)-naph-
thalen-1-yl]-2-propoxy-propionic acid,
3-[4-(2-Cyclopropyl-5-methyl-oxazol-4-ylmethoxy)-naph-
thalen-1-yl]-2-isopropoxy-propionic acid,
3-[4-(2-Cyclopropyl-5-methyl-oxazol-4-ylmethoxy)-benzo
[b]thiophen-7-yl]-2-propoxy-propionic acid,
3-[4-(2-Cyclopropyl-5-methyl-oxazol-4-ylmethoxy)-benzo
[b]thiophen-7-yl]-2-isopropoxy-propionic acid,
3-[4-(2-Cyclopropyl-5-methyl-oxazol-4-ylmethoxy)-benzo
[b]thiophen-7-yl]-2-ethoxy-propionic acid,
3-[4-(2-tert-Butyl-5-methyl-oxazol-4-ylmethoxy)-3,5-dim-
ethyl-phenyl]-2-isopropoxy-propionic acid,
3-[4-(2-tert-Butyl-5-methyl-oxazol-4-ylmethoxy)-3-me-
thyl-phenyl]-2-propoxy-propionic acid,
[rac]-3-[4-(2-tert-Butyl-5-methyl-oxazol-4-ylmethoxy)-2-
methyl-phenyl]-2-ethoxy-propionic acid,
[rac]-3-{4-[2-(2-tert-Butyl-5-methyl-oxazol-4-yl)-ethoxy]-
2-methyl-phenyl}-2-ethoxy-propionic acid,
(S)-3-[4-(2-tert-Butyl-5-methyl-oxazol-4-ylmethoxy)-2-
ethyl-phenyl]-2-ethoxy-propionic acid,
(S)-3-[4-(2-tert-Butyl-5-methyl-oxazol-4-ylmethoxy)-2-
chloro-phenyl]-2-ethoxy-propionic acid,
(S)-3-[4-(2-tert-Butyl-5-methyl-oxazol-4-ylmethoxy)-2-
methoxy-phenyl]-2-ethoxy-propionic acid,
(S)-3-[4-(2-tert-Butyl-5-methyl-oxazol-4-ylmethoxy)-2,6-
dimethyl-phenyl]-2-ethoxy-propionic acid,
(S)-3-{4-[2-(2-tert-Butyl-5-methyl-oxazol-4-yl)-ethoxy]-2,
6-dimethyl-phenyl}-2-ethoxy-propionic acid,
3-{4-[3-(2-tert-Butyl-5-methyl-oxazol-4-yl)-propoxy]-benzo
[b]thiophen-7-yl}-2-ethoxy-propionic acid,
3-{4-[3-(2-tert-Butyl-5-methyl-oxazol-4-yl)-propoxy]-
benzo[b]thiophen-7-yl}-2-ethoxy-propionic acid,
3-{4-[3-(2-tert-Butyl-5-methyl-oxazol-4-yl)-propoxy]-
naphthalen-1-yl}-2-isopropoxy-propionic acid,
3-{4-[3-(2-tert-Butyl-5-methyl-oxazol-4-yl)-propoxy]-
naphthalen-1-yl}-2-ethoxy-propionic acid,
3-{4-[3-(2-tert-Butyl-5-methyl-oxazol-4-yl)-propoxy]-
naphthalen-1-yl}-2-propoxy-propionic acid,
3-{4-[3-(2-tert-Butyl-5-methyl-oxazol-4-yl)-propoxy]-
benzo[b]thiophen-7-yl}-2-methoxy-propionic acid,
2-Ethoxy-3-{4-[2-(2-isopropyl-5-methyl-oxazol-4-yl)-
ethoxy]-naphthalen-1-yl}-propionic acid,
2-Isopropoxy-3-{4-[2-(2-isopropyl-5-methyl-oxazol-4-yl)-
ethoxy]-naphthalen-1-yl}-propionic acid,
2-Ethoxy-3-{4-[3-(2-isopropyl-5-methyl-oxazol-4-yl)-pro-
poxy]-benzo[b]thiophen-7-yl}-propionic acid,
2-Isopropoxy-3-{4-[3-(2-isopropyl-5-methyl-oxazol-4-yl)-
propoxy]-benzo[b]thiophen-7-yl}-propionic acid,
2-Ethoxy-3-{4-[2-(2-isopropyl-5-methyl-oxazol-4-yl)-
ethoxy]-benzo[b]thiophen-7-yl}-propionic acid,
2-Isopropoxy-3-{4-[2-(2-isopropyl-5-methyl-oxazol-4-yl)-
ethoxy]-benzo[b]thiophen-7-yl}-propionic acid,
2-Ethoxy-3-{4-[3-(2-ethyl-5-methyl-oxazol-4-yl)-pro-
poxy]-naphthalen-1-yl}-propionic acid,
2-Ethoxy-3-{4-[2-(2-ethyl-5-methyl-oxazol-4-yl)-ethoxy]-
benzo[b]thiophen-7-yl}-propionic acid,
2-Ethoxy-3-(4-{3-[2-(1-ethyl-propyl)-5-methyl-oxazol-4-
yl]-propoxy}-benzo[b]thiophen-7-yl)-propionic acid, and
2-Ethoxy-3-(4-{2-[2-(1-ethyl-propyl)-5-methyl-oxazol-4-
yl]-ethoxy}-benzo[b]thiophen-7-yl)-propionic acid, or pharmaceutically acceptable salts and/or pharmaceutically acceptable esters thereof.

Particularly preferred compounds of formula (I) are those selected from the group consisting of
(S)-3-{4-[2-(2-tert-Butyl-5-methyl-oxazol-4-yl)-ethoxy]-
naphthalen-1-yl}-2-ethoxy-propionic acid,
(S)-2-But-3-enyloxy-3-{4-[2-(2-tert-butyl-5-methyl-ox-
azol-4-yl)-ethoxy]-naphthalen-1-yl}-propionic acid,
3-{4-[2-(2-tert-Butyl-5-methyl-oxazol-4-yl)-ethoxy]-benzo
[b]thiophen-7-yl}-2-isopropoxy-propionic acid,
3-{4-[2-(2-tert-Butyl-5-methyl-oxazol-4-yl)-ethoxy]-benzo
[b]thiophen-7-yl}-2-ethoxy-propionic acid,
3-{4-[2-(2-tert-Butyl-5-methyl-oxazol-4-yl)-ethoxy]-naph-
thalen-1-yl}-2-isopropoxy-propionic acid,
3-{4-[2-(2-tert-Butyl-5-methyl-oxazol-4-yl)-ethoxy]-3-me-
thyl-phenyl}-2-isopropoxy-propionic acid,
3-{4-[2-(2-Cyclohexyl-5-methyl-oxazol-4-yl)-ethoxy]-
naphthalen-1-yl}-2-propoxy-propionic acid,
3-{4-[2-(2-Cyclopropyl-5-methyl-oxazol-4-yl)-ethoxy]-
benzo[b]thiophen-7-yl}-2-propoxy-propionic acid,
3-{4-[2-(2-Cyclopropyl-5-methyl-oxazol-4-yl)-ethoxy]-
benzo[b]thiophen-7-yl}-2-ethoxy-propionic acid,
3-(4-{2-[2-(2,2-Dimethyl-propyl)-5-methyl-oxazol-4-yl]-
ethoxy}-naphthalen-1-yl)-2-propoxy-propionic acid, and
[rac]-3-{4-[2-(2-tert-Butyl-5-methyl-oxazol-4-yl)-ethoxy]-
2-methyl-phenyl}-2-ethoxy-propionic acid, or pharmaceutically acceptable salts and/or pharmaceutically acceptable esters thereof.

Compounds of formula (I) can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of general formula (I) in this invention may be derivatised at functional groups to provide derivatives which are capable of conversion back to the parent compound in vivo. Physiologically acceptable and metabolically labile derivatives, which are capable of producing the parent compounds of general formula (I) in vivo are also within the scope of this invention.

A further aspect of the present invention is the process for the manufacture of compounds of formula (I) as defined above, which process comprises removing a protecting group in a compound of formula (II)

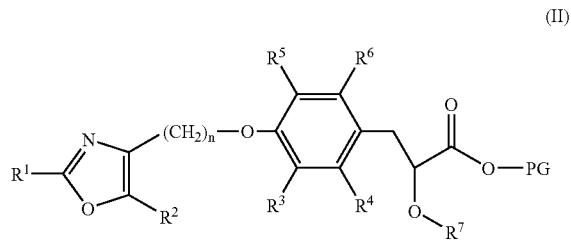

(II)

wherein $R^1$, $R^2$, $R^3$, $R^4$, $R^5$, $R^6$, $R^7$ and n are as defined before and PG is a protecting group.

Possible protecting groups PG in compounds of formula (II) are e.g. lower-alkyl-, β-trimethylsilylethyl- and β-trichloroethyl-esters, which can be used for the protection of the corresponding carboxy group. Lower-alkyl-ester protecting groups can be removed in the presence of a base such as e.g. LiOH or NaOH in a solvent such as e.g. $H_2O$, ethanol, tetrahydrofuran, or dioxan, or in a mixture of such solvents, e.g. in a temperature range of 10–50° C. The β-trichloroethyl-ester protecting group can be removed in the presence of Zn in acetic acid, e.g. in a temperature range of 10–50° C. The β-trimethylsilylethyl-ester protecting group can be removed in the presence of tetrabutylammonium fluoride in tetrahydrofuran, e.g. in a temperature range of 20–65° C. Methods for converting a compound of formula (I) as defined above to a pharmaceutically acceptable salt are known in the art.

The invention further relates to compounds of formula (I) as defined above, when manufactured according to a process as defined above.

As described above, the compounds of formula (I) of the present invention can be used as medicaments for the treatment and/or prevention of diseases which are modulated by PPARα and/or PPARγ agonists. Examples of such diseases are diabetes, particularly non-insulin dependent diabetes mellitus, elevated blood pressure, increased lipid and cholesterol levels, atherosclerotic diseases, metabolic syndrome, endothelial dysfunction, procoagulant state, dyslipidemia, polycystic ovary syndrome, inflammatory diseases (such as e.g. crown disease, inflammatory bowel disease, collitis, pancreatitis, cholestasis/fibrosis of the liver, and diseases that have an inflammatory component such as e.g. Alzheimer's disease or impaired/improvable cognitive function) and proliferative diseases (cancers such as e.g. liposarcoma, colon cancer, prostate cancer, pancreatic cancer and breast cancer). The use as medicament for the treatment and/or prevention of non-insulin dependent diabetes mellitus is preferred.

The invention therefore also relates to pharmaceutical compositions comprising a compound as defined above and a pharmaceutically acceptable carrier and/or adjuvant.

Further, the invention relates to compounds as defined above for use as therapeutic active substances, particularly as therapeutic active substances for the treatment and/or prevention of diseases which are modulated by PPARα and/or PPARγ agonists. Examples of such diseases are diabetes, particularly non-insulin dependent diabetes mellitus, elevated blood pressure, increased lipid and cholesterol levels, atherosclerotic diseases, metabolic syndrome, endothelial dysfunction, procoagulant state, dyslipidemia, polycystic ovary syndrome, inflammatory diseases and proliferative diseases, preferably non-insulin dependent diabetes mellitus.

In another embodiment, the invention relates to a method for the treatment and/or prevention of diseases which are modulated by PPARα and/or PPARγ agonists, which method comprises administering a compound of formula (I) to a human or animal. Preferred examples of such diseases are diabetes, particularly non-insulin dependent diabetes mellitus, elevated blood pressure, increased lipid and cholesterol levels, atherosclerotic diseases, metabolic syndrome, endothelial dysfunction, procoagulant state, dyslipidemia, polycystic ovary syndrome, inflammatory diseases and proliferative diseases, preferably for the treatment and/or prevention of non-insulin dependent diabetes mellitus.

The invention further relates to the use of compounds as defined above for the treatment and/or prevention of diseases which are modulated by PPARα and/or PPARγ agonists. Preferred examples of such diseases are diabetes, particularly non-insulin dependent diabetes mellitus, elevated blood pressure, increased lipid and cholesterol levels, atherosclerotic diseases, metabolic syndrome, endothelial dysfunction, procoagulant state, dyslipidemia, polycystic ovary syndrome, inflammatory diseases and proliferative diseases, preferably non-insulin dependent diabetes mellitus.

In addition, the invention relates to the use of compounds as defined above for the preparation of medicaments for the treatment and/or prevention of diseases which are modulated by PPARα and/or PPARγ agonists. Preferred examples of such diseases are diabetes, particularly non-insulin dependent diabetes mellitus, elevated blood pressure, increased lipid and cholesterol levels, atherosclerotic diseases, metabolic syndrome, endothelial dysfunction, procoagulant state, dyslipidemia, polycystic ovary syndrome, inflammatory diseases and proliferative diseases, preferably non-insulin dependent diabetes mellitus. Such medicaments comprise a compound as defined above.

The compounds of formula (I) can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the text or in the examples, or by methods known in the art.

Homochiral compounds of formula (I) (compounds 10 and 11 in scheme 1 and compounds 6 and 7 in scheme 3) can be prepared according to the methods depicted in scheme 1 and 3 or by analogous methods.

Racemates of compounds of formula (I) (compounds 9 and compounds 10 in scheme 2 and compounds 9 and 11 in scheme 4) can e.g. be synthesized according to the methods depicted in scheme 2 or 4 or by analogous methods. The optically pure (S)-enantiomer can then be prepared from racemates of compounds of formula (I) by methods known in the art, such as separation of the antipodes via diastereomeric salts by crystallization with optically pure amines such as e.g. (R) or (S)-1-phenyl-ethylamine, (R) or (S)-1- naphthalen-1-yl-ethylamine, brucine, quinine, quinidine, or by separation of the antipodes by specific chromatographic methods using either a chiral adsorbens or a chiral eluent.

Scheme 1

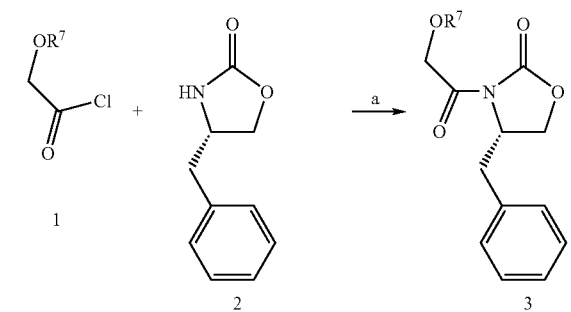

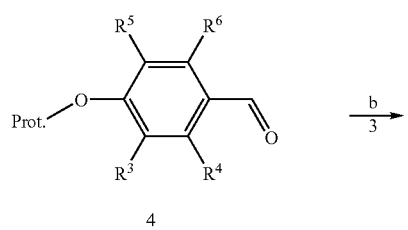

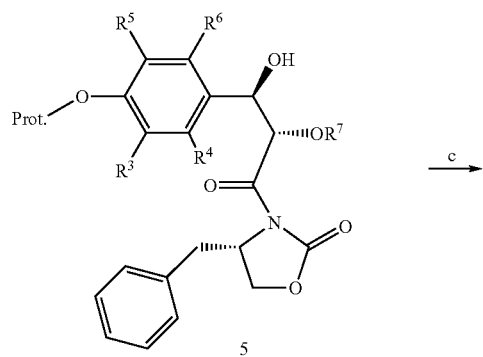

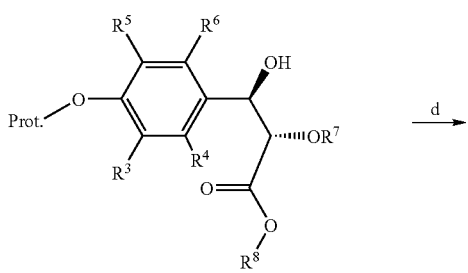

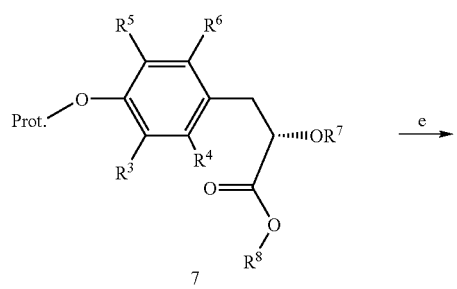

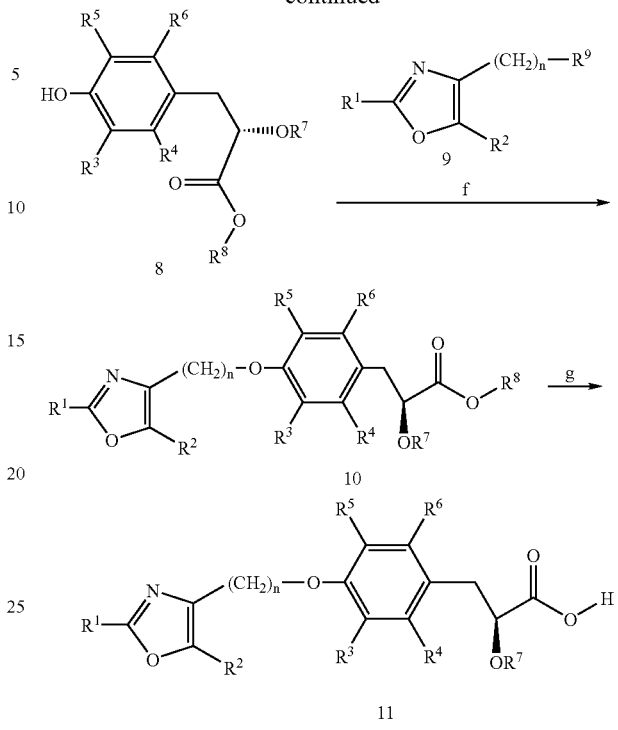

Homochiral alpha-alkoxy-phenyl-propionic acid esters of formula 10 and free acids of formula 11 can be prepared according to the method depicted in scheme 1 or by analogous methods known in the art.

The well known chiral auxiliary 2 [(S)-4-benzyl-oxazolidin-2-one] is condensed with an alkoxy-acetyl chloride 1 in the presence of a strong base like n-butyl lithium in an inert solvent like tetrahydrofuran at temperatures around −78° C. to produce building block 3 (step a). The latter is then treated according to literature precedence [Tetrahedron Asymmetry (1999), 10, 1353–1367] with dibutylboron-triflate and a tertiary amine like triethylamine in dichloromethane to generate the corresponding boron enolate, which is subsequently reacted at low temperatures with aldehydes 4 (prepared as outlined in schemes 5–11) resulting in compounds 5 (step b). In these aldol products 5, one of all four possible stereoisomers is strongly predominating (stereochemistry as indicated without rigorous proof with respect to the benzylic position). Compounds 5 are converted into phenolic intermediates 8 via a three step sequence encompassing: i) carefully controlled ester formation using only a minimal excess of an alkali alcoholate in the corresponding alcohol as solvent or in solvents like tetrahydrofuran or dioxane at temperatures ranging from −20° C. to room temperature to give ester compounds 6 (step c); ii) removal of the benzylic hydroxy group in 6 with a reducing agent like e.g. triethylsilane in the presence of a Lewis acid, like boron-trifluoride, or a protic acid, like trifluoroacetic acid, in a suitable solvent like trifluoroacetic acid itself or dichloromethane between 0° C. and 60° C. to yield protected phenol compounds 7 (step d); iii) ensuing removal of the protecting group, e.g. a benzyl group, by standard technology, e.g. catalytic hydrogenation using hydrogen and a catalyst like palladium or by using dimethyl sulfide and boron trifluoride diethyl etherate in a solvent like dichloromethane between room temperature and the reflux temperature of the solvent to give phenolic compounds. 8 (step e); the order of the three reaction steps c, d, e is interchangeable, and catalytic hydrogenation can also be used for the simultaneous removal of the benzylic hydroxy function and a benzyl protecting group, preferably using palladium on charcoal as catalyst in the presence of an acid like oxalic acid in solvents like alcohols at temperatures around room temperature and a hydrogen pressure up to 100 bar.

Alkyl-oxazole compounds 9 (prepared as outlined in schemes 12 and 13) are condensed with phenols 8 according to well known procedures: if $R^9$ represents a hydroxy group e.g. via Mitsunobu-reaction, e.g. with triphenylphosphine and di-tert-butyl-, diisopropyl-, or diethyl-azodicarboxylate as reagents; this transformation is preferably carried out in a solvent like toluene, dichloromethane or tetrahydrofuran at ambient temperature. Alternatively, if $R^9$ represents a halide, mesylate or tosylate moiety, the aryl-oxazole compounds 9 can be reacted with phenols 8 in solvents like N,N-dimethylformamide, acetonitrile, acetone or methyl-ethyl ketone in the presence of a weak base like cesium or potassium carbonate at a temperature ranging from room temperature to 140° C., preferably around 50° C., to yield ether compounds 10 (step f). Those can optionally be hydrolyzed according to standard procedures, e.g. by treatment with an alkali hydroxide like LiOH or NaOH in a polar solvent mixture like tetrahydrofuran/ethanol/water leading to carboxylic acids 11 (step g). If carefully controlled reaction conditions are applied as detailed in the experimental part, hardly any racemisation occurs during this reaction sequence. The optical purity of compounds 10 and 11 can be determined by chiral HPLC or by $^1$H-NMR-spectroscopy in the presence of a chiral solvent like 1-(9-anthryl)-2,2,2-trifluoro-ethanol, and has been found higher than 95% in all cases exemplified.

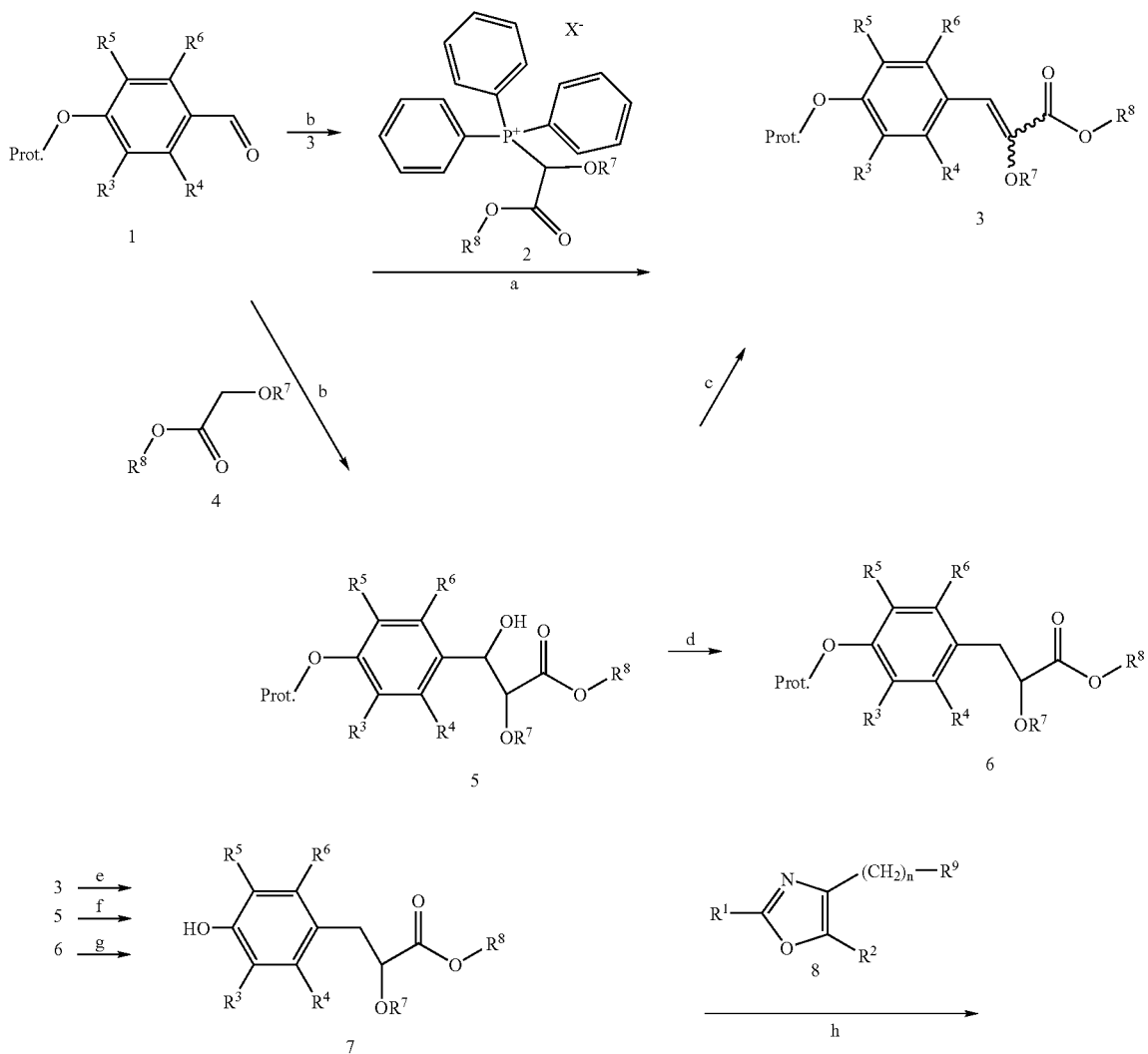

Scheme 2

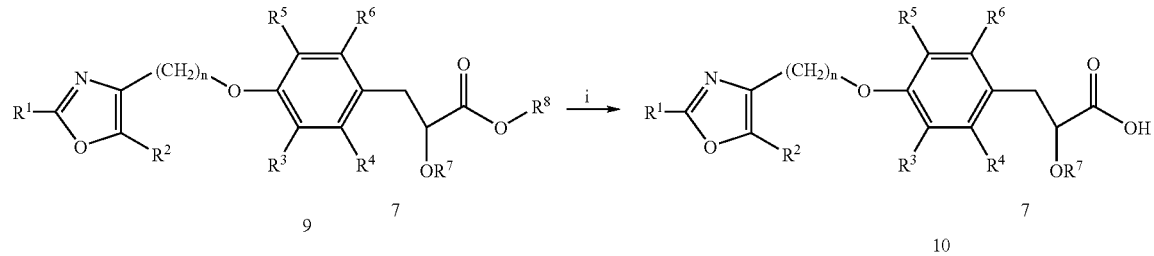

Aldehydes 1 (prepared as outlined in schemes 5–11) can be reacted with a Wittig salt 2 such as (1,2-diethoxy-2-oxoethyl)triphenyl phosphonium chloride or (1,2-dimethoxy-2-oxoethyl)triphenyl phosphonium bromide in solvents like isopropanol, dichloromethane, or tetrahydrofuran, or mixtures thereof in the presence of a base like potassium carbonate, 1,8-diazabicyclo [5.4.0] undec-7-ene (DBU) or 1,1,3,3-tetramethyl-guanidine, preferably between 0° C. and the reflux temperature of the solvents, giving acrylic esters 3 as E and/or Z isomers (step a). Hydrogenation of cinnamic esters 3 using palladium on charcoal as catalyst, preferably at room temperature and 1 atm. pressure of hydrogen, in solvents like methanol, ethanol, tetrahydrofuran, acetic acid, dichloromethane and mixtures thereof, affords racemic esters 7, provided that the protecting group can be cleaved reductively (step e).

Alternatively, aldehydes 1 are reacted with the enolate of alkoxy-acetic acid esters 4 (preferably the lithium-enolate, prepared at –78° C. by treatment of 4 with a strong, non-nucleophilic base like lithium diisopropylamide in an inert solvent like tetrahydrofuran), preferably at temperatures around –78° C., in solvents like tetrahydrofuran, giving the aldol product 5 as a mixture of diasteromers (step b). Removal of the benzylic hydroxy group as described above for the conversion of compounds 6 to compounds 7 in scheme 1 yields racemic esters 6 (step d); ensuing removal of the protecting group, e.g. a benzyl group, can then be performed by standard technology as described for the conversion of compounds 7 to compounds 8 in scheme 1 to give phenolic compounds 7 (step g). Catalytic hydrogenation can also be used to convert in one step benzyl protected hydroxy compounds 5 into phenolic compounds 7 (step f) as described for the conversion of compounds 6 to compounds 8 in scheme 1. The cleavage of the protective function can also be performed before the removal of the benzylic hydroxy group; in such a case, similar reaction conditions can be chosen for the removal of the benzylic hydroxy group as just described for the transformation of compounds 5.

As an alternative method, compounds 5 can be treated with catalytic amounts of an acid like para toluene sulfonic acid in a solvent like benzene or toluene, preferably under conditions allowing the removal of the water formed (e.g. with a Dean Stark trap or in the presence of molecular sieves) at temperatures between room temperature and the reflux temperature of the solvents to yield cinnamic esters 3 (step c).

The transformation of phenolic intermediates 7 into esters 9 and/or acids 10 can be performed in perfect analogy as described for homochiral phenolic intermediates 8 in scheme 1 (steps h and i).

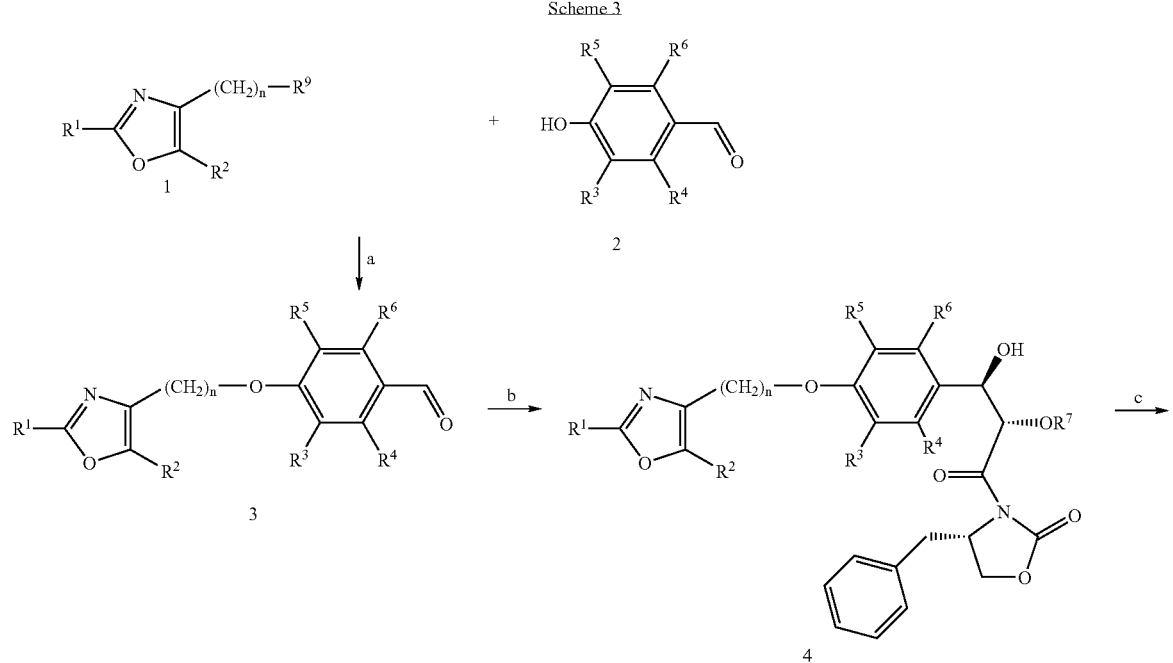

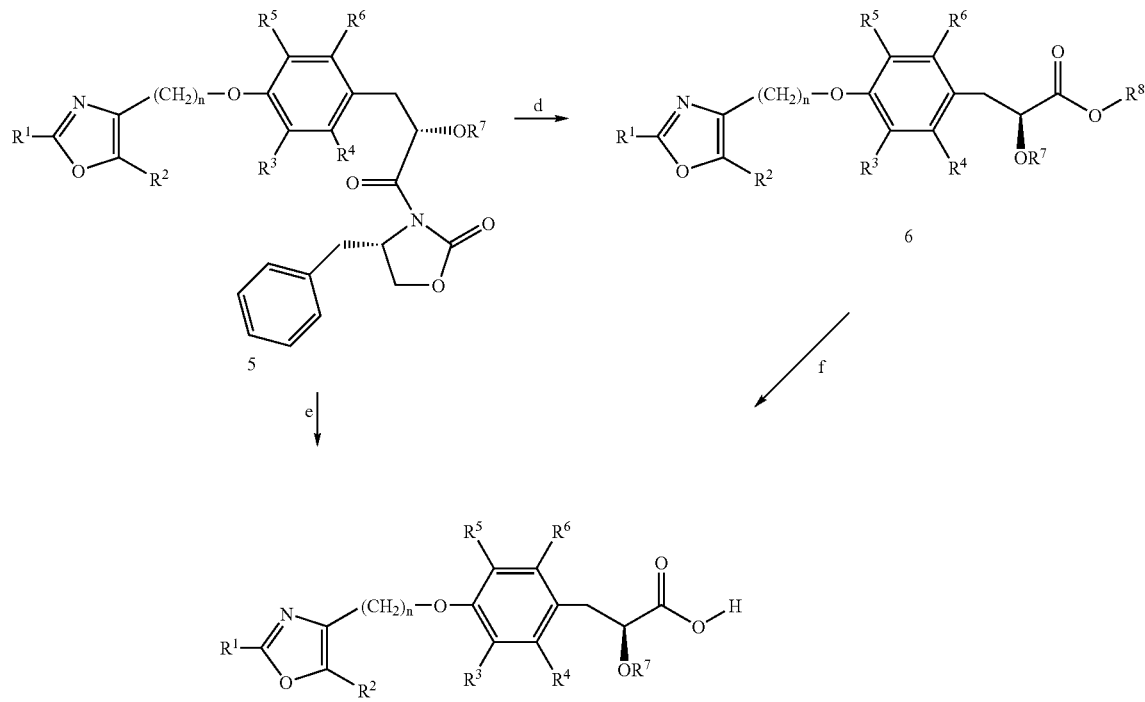

Homochiral alpha-alkoxy-phenyl-propionic acid esters of formula 6 and free acids of formula 7 can also be prepared according to a linear synthetic sequence depicted in scheme 3. Thus, reaction types already described in scheme 1 are used in a different order beginning with the condensation of alkyl-oxazole synthons 1 (prepared as outlined in schemes 12 and 13) with phenols 2 (prepared as outlined in schemes 5–11) affording ether compounds 3 bearing an aldehyde moiety (step a). In case $R^3$, $R^4$, $R^5$, or $R^6$ contain a functional group, which might not be compatible with the following reaction steps, e.g. a phenolic OH-function, then a protective group should be attached to such a functional group, e.g. a tert-butyl-dimethyl-silyl moiety. Such a protective group can then be removed at a suitable stage later in the reaction sequence.

These ether compounds 3 are then reacted with the chiral synthons (compounds 3 in scheme 1) to form aldol-adducts 4 (step b). Removal of the benzylic hydroxy function in compounds 4 leads to compounds 5 (step c), which can be converted into the corresponding esters 6 (step d) or acids 7 (step e) as described for the analogous reactions in scheme 1 and 2, respectively.

Optionally, ester compounds 6 can be hydrolysed to acids 7 (step f). The optical purity of compounds 6 and 7 can be determined by chiral HPLC or by $^1$H-NMR-spectroscopy in the presence of a chiral solvent like 1-(9-anthryl)-2,2,2-trifluoro-ethanol and has been found to be higher than 95% in all cases exemplified.

Scheme 4, Part I

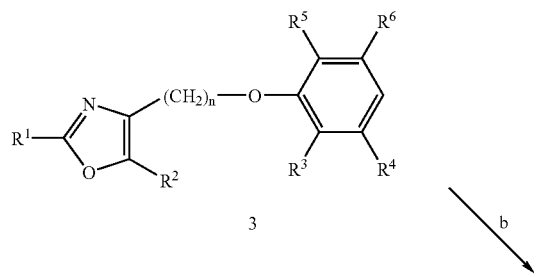

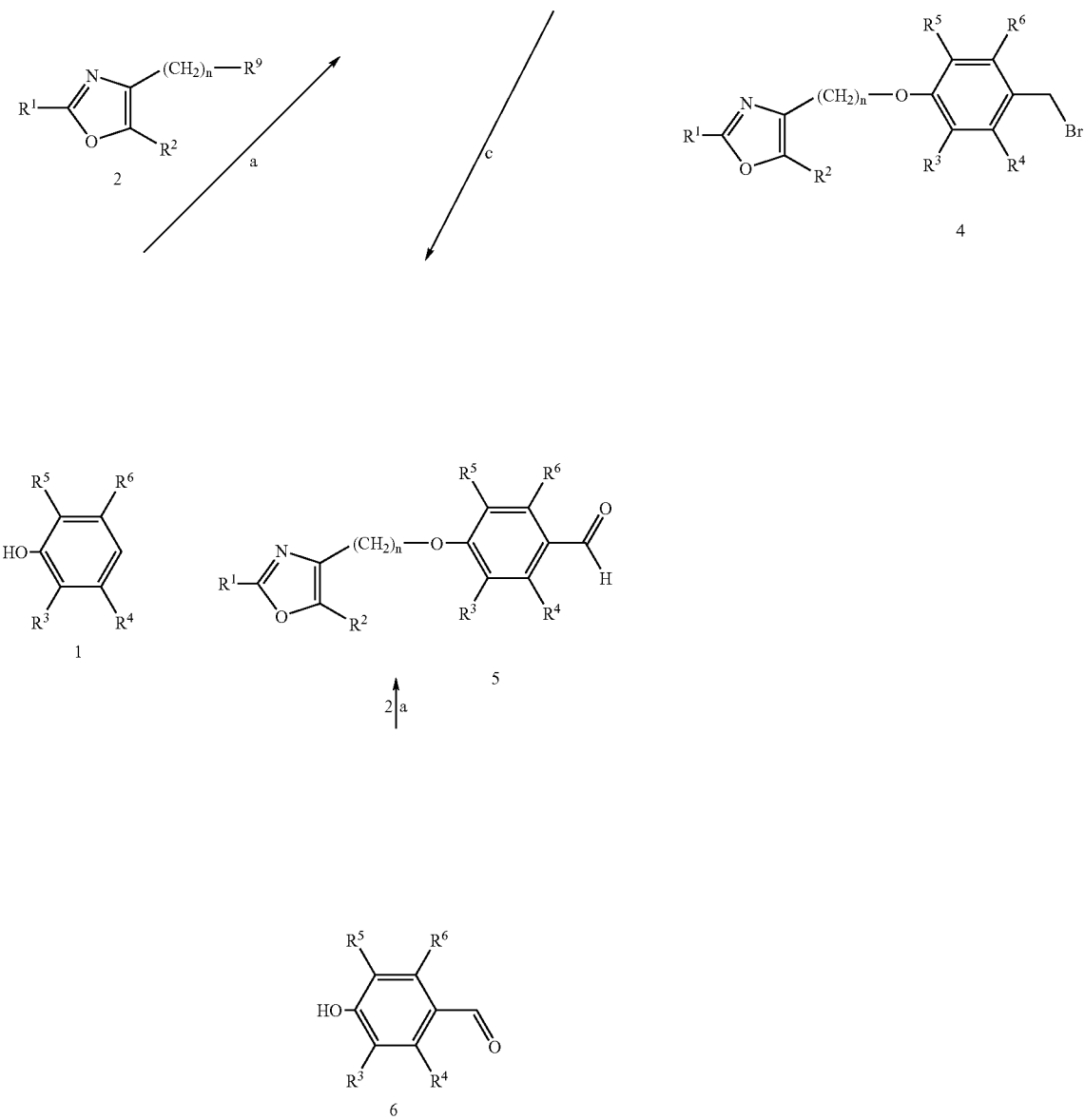
Scheme 4, Part II
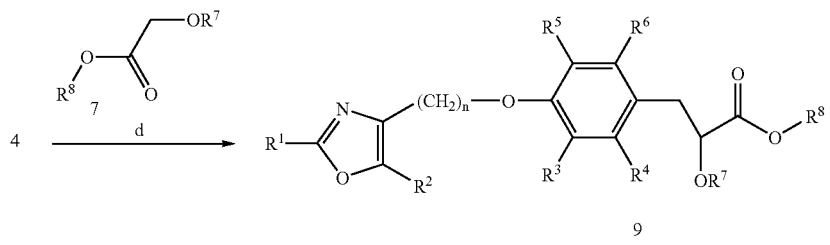

-continued

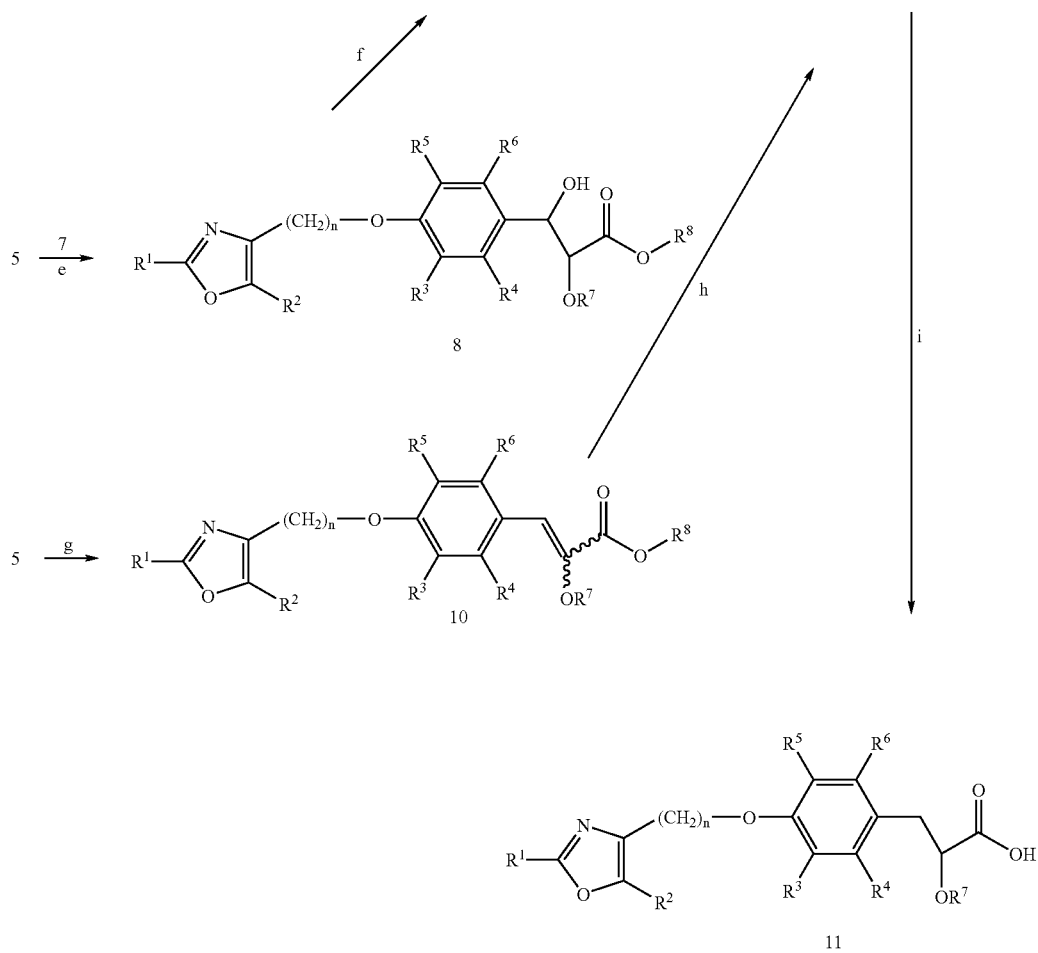

Alkyl-oxazole compounds 2 (prepared as outlined in schemes 12 and 13) are condensed with phenols 1 or aldehydes 6 (prepared as outlined in schemes 5–11) in perfect analogy as described for homochiral phenolic intermediates 8 and alkyl-oxazole compounds 9 in scheme 1; thus ether compounds 3 or aldehydes 5 are obtained (step a). The former are then subjected to bromomethylation, e.g. by treatment with trioxane and HBr, preferably 62% aq. HBr, in an inert solvent, preferably dichloromethane, preferably at 0° C., giving a highly reactive, often quite unstable electrophile 4 (step b). The electrophile 4 is suitable to alkylate an enolate of alkoxy-acetic acid esters 7 ($R^8$=lower alkyl), preferably the lithium-enolate, prepared at −78° C. by treatment of 7 with a strong, non-nucleophilic base like lithium diisopropylamide in an inert solvent like tetrahydrofuran, to give esters 9 (step d). To increase the reactivity of the enolate nucleophile, the reaction is preferably performed in the presence of a cosolvent like hexamethylphosphoramide (HMPA) or 1,3-dimethyl-3,4,5,6-tetrahydro-2(1H)-pyrimidinone (DMPU).

Alternatively, aldehyde compounds 5, which are also available from ether intermediates 3 by Vilsmeier formylation or through formylation with dichloromethyl methyl ether in the presence of titanium tetrachloride, preferably in dichloromethane at temperatures between −78° C. and the reflux temperature of the solvent (step c), are reacted with an enolate of alkoxy-acetic acid esters 7 as described for the analogous reaction of compounds 1 and compounds 4 in scheme 2 giving the aldol products 8 as a mixture of diasteromers (step e). Removal of the benzylic hydroxy group in compounds 8 leads to racemic esters 9 (step f), as described for the analogous reactions in scheme 1, 2 and 3, respectively.

Alternatively, aldehydes 5 can be reacted with a Wittig salt as described for the conversion of compounds 1 to compounds 3 in scheme 2 giving acrylic esters 10 as E and/or Z isomers (step g). Hydrogenation of acrylic esters 10 as described for the analogous reaction in scheme 2 leads to compounds 9 (step h). Hydrolysis of racemic ester compounds 9 can be performed in perfect analogy as described for homochiral compounds 10 in scheme 1 leading to carboxylic acids 11 (step i).

Aldehydes 4 (scheme 1), aldehydes 1 (scheme 2), aldehydes 2 (scheme 3), and aldehydes 6 (scheme 4) are known or can be synthesized by methods known in the art. Examples for possible syntheses of these key intermediates are given in schemes 5–11.

Scheme 5

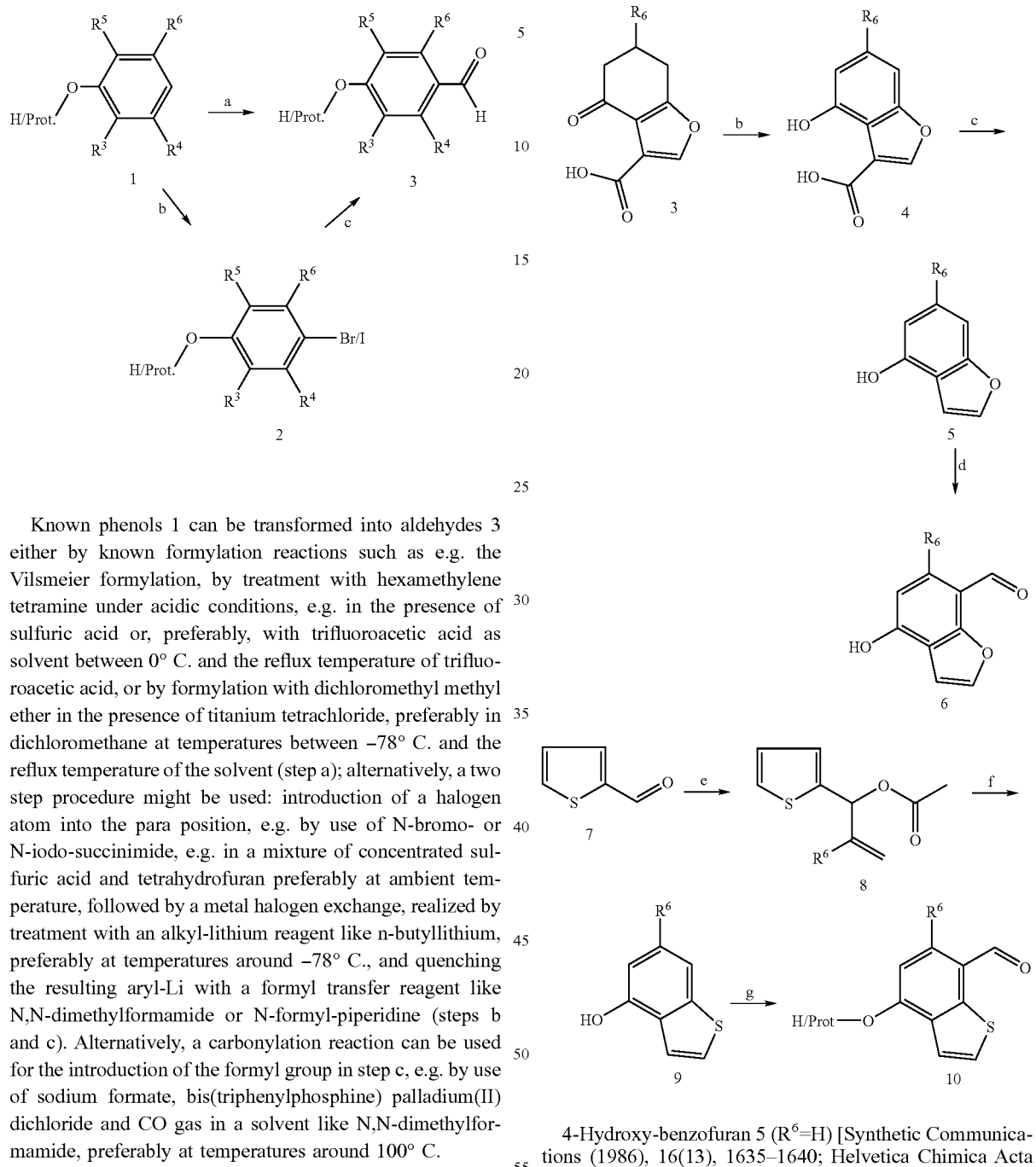

Known phenols 1 can be transformed into aldehydes 3 either by known formylation reactions such as e.g. the Vilsmeier formylation, by treatment with hexamethylene tetramine under acidic conditions, e.g. in the presence of sulfuric acid or, preferably, with trifluoroacetic acid as solvent between 0° C. and the reflux temperature of trifluoroacetic acid, or by formylation with dichloromethyl methyl ether in the presence of titanium tetrachloride, preferably in dichloromethane at temperatures between −78° C. and the reflux temperature of the solvent (step a); alternatively, a two step procedure might be used: introduction of a halogen atom into the para position, e.g. by use of N-bromo- or N-iodo-succinimide, e.g. in a mixture of concentrated sulfuric acid and tetrahydrofuran preferably at ambient temperature, followed by a metal halogen exchange, realized by treatment with an alkyl-lithium reagent like n-butyllithium, preferably at temperatures around −78° C., and quenching the resulting aryl-Li with a formyl transfer reagent like N,N-dimethylformamide or N-formyl-piperidine (steps b and c). Alternatively, a carbonylation reaction can be used for the introduction of the formyl group in step c, e.g. by use of sodium formate, bis(triphenylphosphine) palladium(II) dichloride and CO gas in a solvent like N,N-dimethylformamide, preferably at temperatures around 100° C.

Scheme 6

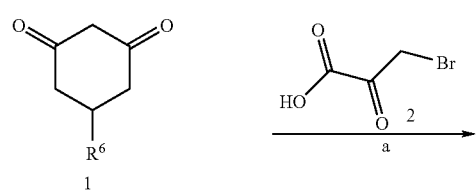

4-Hydroxy-benzofuran 5 ($R^6$=H) [Synthetic Communications (1986), 16(13), 1635–1640; Helvetica Chimica Acta (1933), 16, 121–1291 and 4-hydroxy-benzothiophene 9 ($R^6$=H) [Jpn. Kokai Tokkyo Koho (2001), 2001048876A2] are known. Thus, cyclohexane-1,3-diones 1 carrying variable substituents $R^6$ at the 5-position can be reacted with bromo-pyruvic acid in methanol in the presence of a base like potassium hydroxide at temperatures between 0° C. and the reflux temperature of methanol followed by treatment with hydrochloric acid at around 100° C. to give furan-carboxylic acids 3 (step a). Treatment of these furan-carboxylic acids 3 in an inert solvent like decahydro-naphthalene in the presence of a hydrogen acceptor like dodecene and palladium on carbon, preferably at reflux, provides carboxy-benzofurans 4 (step b), which are decarboxylated to benzofurans 5, e.g. by using copper powder in quinoline at temperatures between 200° C. and 240° C. (step c). Similar to the transformations described in scheme 5, benzofurans 5 can finally be converted into formylated benzofuran intermediates 6 (step d).

Treatment of 2-thiophenecarbaldehyde 7 with suitable vinyl-lithium- or vinyl-magnesium-derivatives in solvents like tetrahydrofuran or 1,2-dimethoxy-ethane, preferably in a temperature range between −78° C. and room temperature, followed by in situ treatment with acetic anhydride yields thiophenes 8 with variable substitution $R^6$ (step e). Treatment of thiophenes 8 with carbon monoxide, preferably at a pressure of 20 to 60 bar, a palladium catalyst like palladium acetate, a phosphine like triphenylphosphine, in solvent mixtures which may typically contain acetic anhydride, triethylamine, toluene or tetrahydrofuran, preferably in a temperature range between 100° C. to 160° C., affords after saponification of the acetate function benzothiophenes 9 (step f). Similar to the transformations described in scheme 5, benzothiophenes 9 can finally be converted into formylated benzothiophene intermediates 10 (step g).

Scheme 7

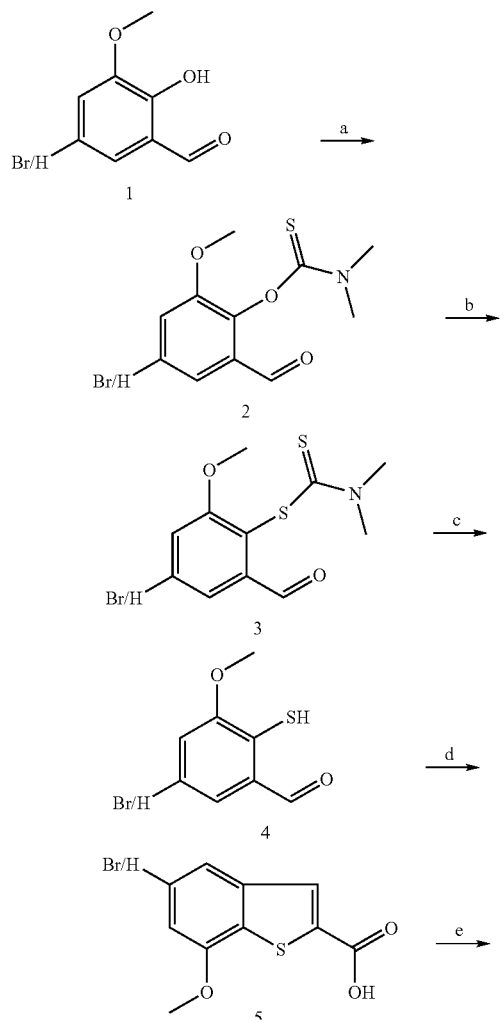

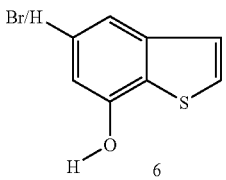

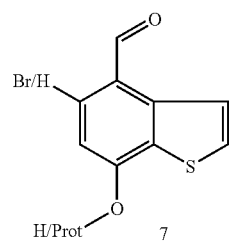

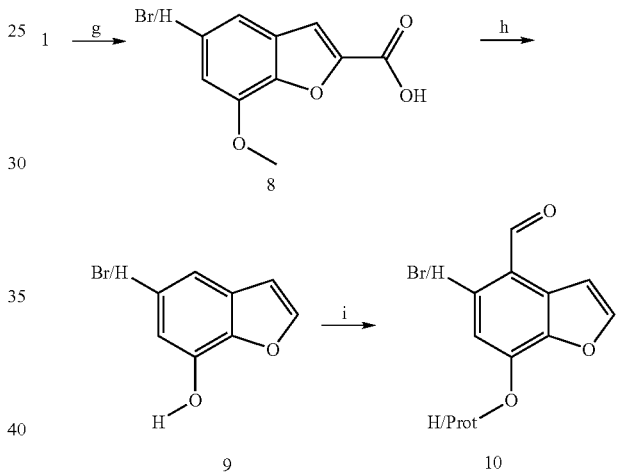

2-Hydroxy-3-methoxy-benzaldehyde 1, optionally substituted with bromine in position 5, can be transformed into benzo[b]thiophen-7-ol 6 or 5-bromo-benzo[b]thiophen-7-ol 6. This sequence can be carried out in analogy to the method described in J. Chem. Soc., Perkin Trans. 1 1983(12), 2973–7 for the transformation of 2-hydroxy-3-methoxy-benzaldehyde into benzo[b]thiophen-7-ol. It involves the following steps: treatment with N,N-dimethylthiocarbamoyl chloride in a solvent like tetrahydrofuran in the presence of an aqueous base like potassium hydroxide in water or in the presence of an organic base like diisopropyl-ethyl-amine, preferably at temperatures between 0° C. and room temperature, generates thionocarbamates 2 (step a); thermal rearrangement of compounds 2 without solvent or preferably in an inert solvent like diphenyl ether at temperatures between 200° C. and 280° C. leads to arylthiocarbamates 3 (step b); saponification in a solvent like an alcohol with a base like sodium or potassium hydroxide, preferably between room temperature and the reflux temperature of the solvents, leads then to thiophenols 4 (step c); reaction of these thiophenols 4 with sodium chloroacetate in water or a water/alcohol mixture in the presence of a base like sodium or potassium hydroxide in a temperature range between room temperature and the reflux temperature of the solvents produces then benzothiophene-carboxylic acids 5 (step d); decarboxylation, e.g. in quinoline in the presence of copper bronze at temperatures between 200° C. and 240° C., followed by cleavage of the methyl ether function, e.g. by treatment with aqueous hydrobromic acid in acetic acid at reflux, then yields benzo[b]thiophen-7-ols 6 (step e). Similar to the transformations described in scheme 5, benzo[b]thiophen-7-ols 6 can finally be converted into formylated benzo[b]thiophen-7-ol intermediates 7 (step f).

7-Hydroxy-benzofuran is known [J. Med. Chem. (1987), 30(1), 62–7] and commercially available. In a sequence similar to that described above, the 5-bromo-analogue can be prepared from 2-hydroxy-3-methoxy-benzaldehyde 1 by reaction with ethyl chloro-acetate in a solvent like N,N-dimethylformamide in the presence of a base like potassium carbonate at temperatures between 60° C. and 120° C. yielding benzofuran carboxylic acid 8 (step g). Decarboxylation as described above and ensuing ether cleavage, preferably with pyridine hydrochloride at temperatures around 200° C., then leads to 5-bromo-7-hydroxy-benzofuran 9 (step h). Similar to the transformations described in scheme 5,5-bromo-7-hydroxy-benzofuran 9 can finally be converted into formylated 5-bromo-7-hydroxy-benzofuran intermediate 10 (step i).

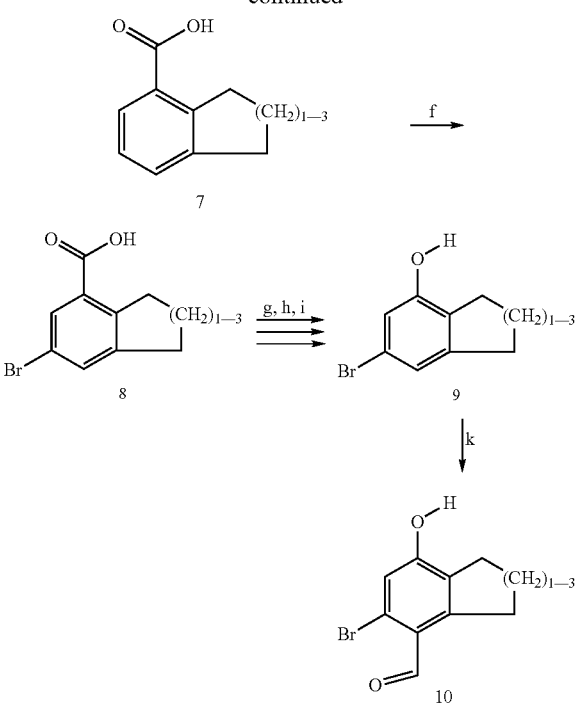

Scheme 8

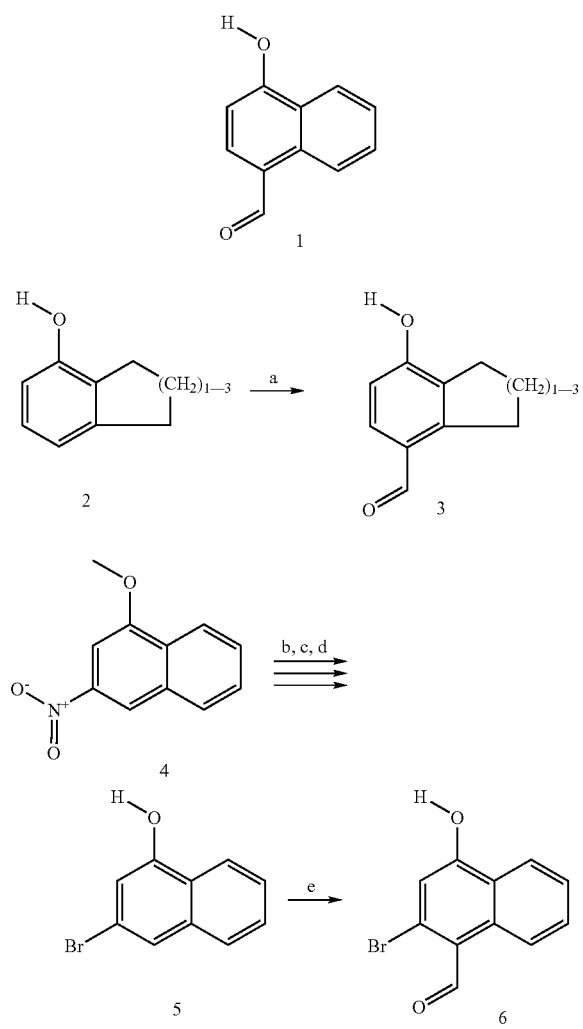

Hydroxy-4-formyl-naphthalene 1 and 2,3-annelated phenols 2 with a ring size of 5, 6 and 7 are commercially available or known [see J. Am. Chem. Soc. (1988), 110(19), 6471–6480; U.S. (2000) U.S. Pat. No. 6,121,397; PCT Int. Appl. (1999) WO99/10339]. Similar to the transformations described in scheme 5,2,3-annelated phenols 2 can be converted into formylated 2,3-annelated phenols 3 (step a).

Bromo-1-hydroxy-naphthalene 5, an intermediate carrying a functionality, which allows synthetic modifications at a later stage, can be prepared from 3-nitro-1-methoxy-naphthalene 4 [Monatsh. Chem. (1992), 123(6–7), 637–645] by well established procedures, i.e. reduction of the nitro function, e.g. by hydrogenation in the presence of a palladium catalyst, followed by diazotisation, Sandmeyer reaction and cleavage of the methyl ether function giving 3-bromo-1-hydroxy-naphthalene 5 (steps b, c, d). Similar to the transformations described in scheme 5,3-bromo-1-hydroxy-naphthalene 5 can be converted into 3-bromo-4-formyl-1-hydroxy-naphthalene 6 (step e).

2,3-Annelated carboxylic acids 7 are known, their 3-bromo analogues 8 are known or can be prepared by established methods of bromination of aromatic nuclei [J. Org. Chem. (1978), 43(11), 2167–70; Ger. Offen. (1977), DE 2633905] (step f). Such 3-bromo-benzoic acids can then be converted into the corresponding phenols 9 by known methods such as e.g. exhaustive reduction with borane to the corresponding alcohol, oxidation, e.g. using Swern conditions (oxalyl chloride/dimethylsulfoxide/triethylamine in dichloromethane, −78° C. to room temperature), to the corresponding aldehyde, followed by Baeyer-Villiger oxidation with peracetic acid (40%) in acetic acid (steps g, h, i). Similar to the transformations described in scheme 5, phenols 9 can be converted into intermediates 10 (step k).

Scheme 9

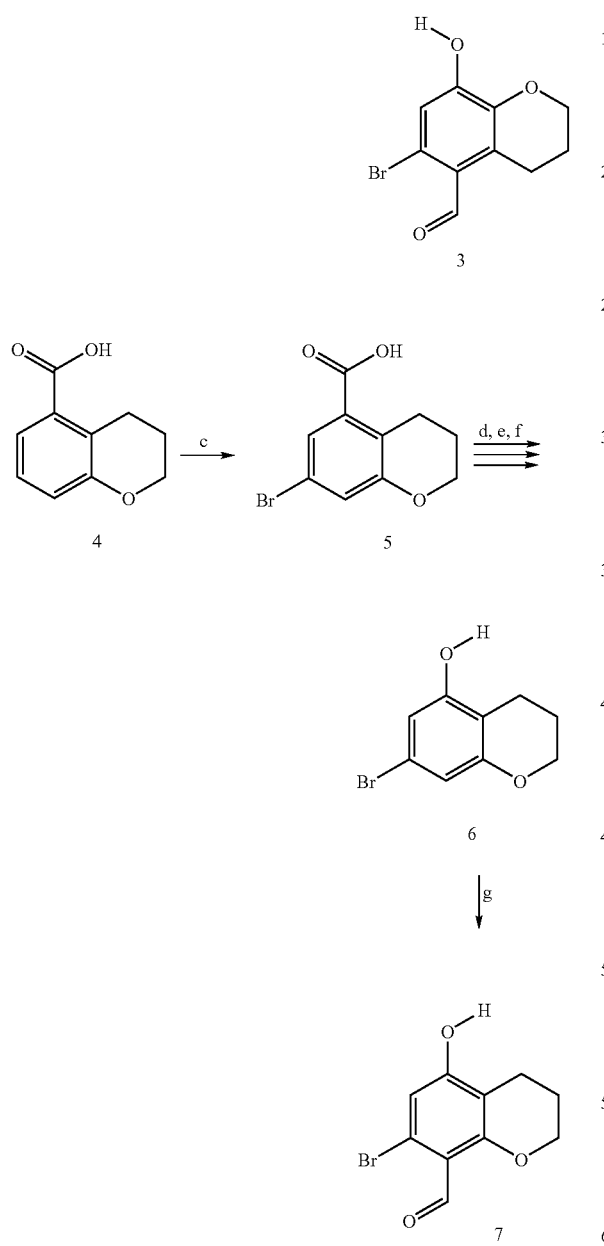

Bromo-methoxy compound 1 characterized by an annelated dihydro-2H-pyran ring is known [Can. J. Chem. (1982), 60(16), 2093–8]. Cleavage of the methoxy ether function with pyridine hydrochloride at temperatures around 200° C. leads to 3-bromo-phenol 2 (step a). Similar to the transformations described in scheme 5, compound 2 can be converted into intermediate 3 (step b).

The isomeric building block can be obtained as follows: Carboxylic acid 4 [U.S. (1999), U.S. Pat. No. 5,856,529 A] can be brominated to give the 3-bromo derivative 5 (step c), which can be transformed into phenol 6 by a sequence analogous to that described for the transformation of compounds 8 into compounds 9 in scheme 8 (steps d, e, f). Similar to the transformations described in scheme 5, phenol 6 can be converted into intermediate 7 (step g).

Scheme 10

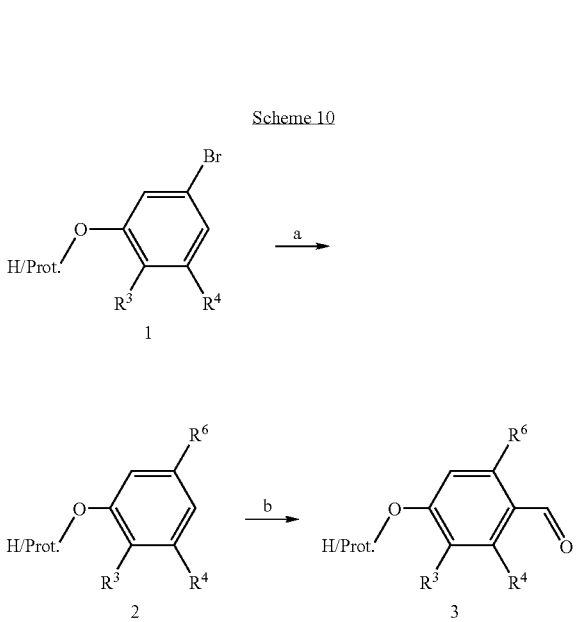

3-Bromo-phenols 1 (intermediates 6, scheme 7, intermediates 9, scheme 7, intermediates 5, scheme 8, intermediates 9, scheme 8, as well as intermediates 2 and 6, scheme 9), optionally carrying a protective function, can be converted into analogous phenols 2 carrying variable substituents $R^6$ by first transforming the bromo-compound into the corresponding aryl-lithium derivative (e.g. by using an alkyl lithium reagent in a solvent like tetrahydrofuran, preferably at a temperature around −78° C.) and then quenching the latter with a variety of electrophiles using methods well known in the art (step a). For the synthesis of phenols ($R^6$=OH), the aryl lithium compounds are reacted with trimethyl-borate at temperatures between −78° C. and the reflux temperature of tetrahydrofuran, followed by oxidation, e.g. with N-methyl morpholine N-oxide or $H_2O_2$/NaOH, preferably at the reflux temperature of tetrahydrofuran [compare Synlett 1995(09), 931–932]. These phenols 2 with $R^6$ equal OH can then be transformed into the corresponding ether compounds by well known methods. Similar to the reaction sequence described in scheme 5, phenolic compounds 2 can finally be converted into phenolic aldehyde intermediates 3 (step b).

Scheme 11

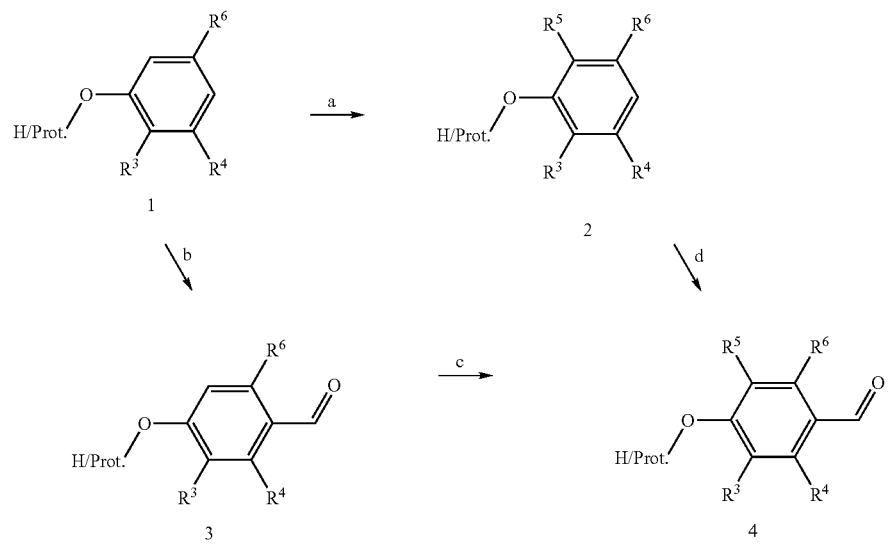

Phenols 1, optionally protected, can be further functionalized into phenols 2 carrying additional substutents $R^5$ by known methods of electrophilic aromatic substitution. In many cases, mixture of ortho/para—substitution-, and ortho/para—disubstitution-products will be formed in ratios depending on the precise reaction conditions. In such cases, the reaction conditions can be optimized in order to achieve the highest possible yield of mono-ortho product; optionally, product mixtures can also be separated into pure isomers by known methods such as silica gel chromatography (step a). 4-Formyl compounds 3 can be obtained from phenols 1, optionally protected, by transformations as described in scheme 5 (step b). 4-Formyl compounds 3 can then again be used as starting materials applying known methods of electrophilic aromatic substitutions leading to compounds 4 carrying an additional $R^5$ substituent (step c). Alternatively, compounds 4 may be obtained from phenols 2 by transformations as described in scheme 5 (step d).

Scheme 12

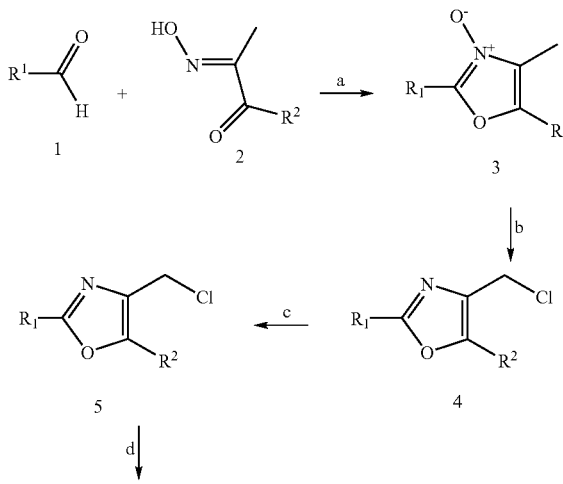

-continued

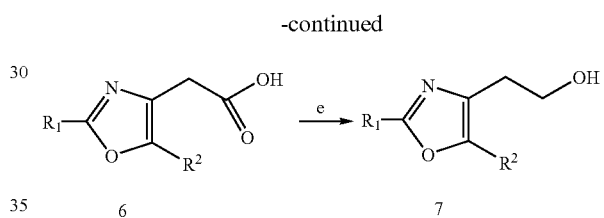

Aldehydes 1 (scheme 12) are commercially available or known. They are condensed with diketo-monoximes 2 according to literature precedence (Chem. Ber. (1915), 48, 897) in the presence of a strong acid, typically HCl, in a polar solvent like AcOH to yield the oxazole-N-oxides 3 (step a). Subsequent treatment with $POCl_3$ in dichloromethane under reflux provides the corresponding primary chlorides 4 (Chem. Pharm. Bull. (1971), 19, 2050; step b). We have surprisingly found, that this method works also with alkyl-oxazole-N-oxides. However, if $R^1$ in 1 contains a hydrogen atom alpha to the carbonyl group, the reaction proceeds in a regio-unselective manner, and the isomers have to be separated by chromatography, optionally after the next step. These intermediates are either used as such, transformed according to well established methods into the corresponding alcohols or activated alcohols like mesylates or tosylates, or into the bromides or iodides, or finally further elaborated via $S_N2$-reaction with NaCN to give, via nitrils 5 (step c), exhaustive hydrolysis (step d) and reduction (step e), e.g. with borane in tetrahydrofuran, the building blocks 7.

4-Chloromethyl-2-alkyl-oxazoles 4 with $R^2$ equal hydrogen are preferably prepared from the corresponding alkyl carboxamides and 1,3-dichloroacetone as described e.g. in Bioorg. Med.), Chem. Lett. (2000), 10(17), 2041–2044.

Scheme 13

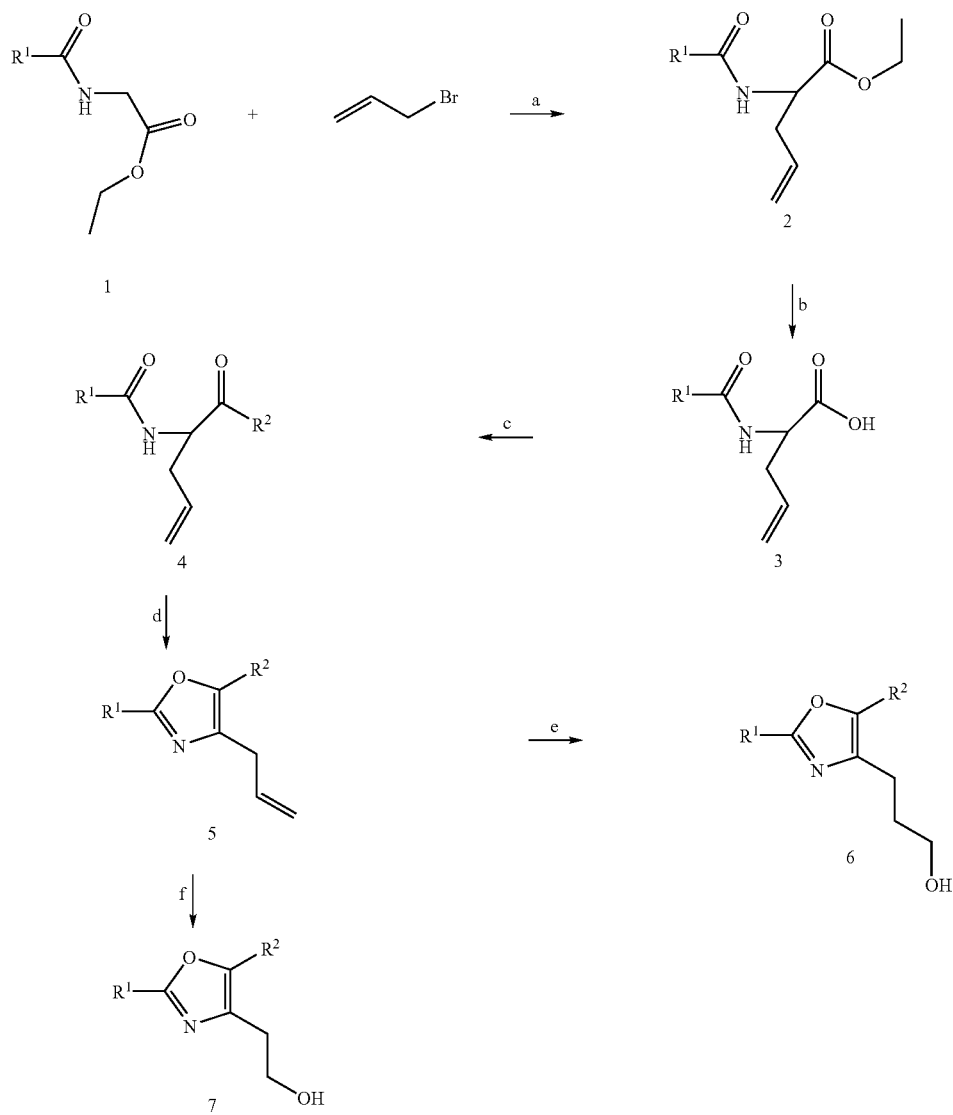

N-Acyl-glycine esters 1 (scheme 13) are either commercially available, known, or can be prepared by standard operations of N-acylation. Mono-allylated esters 2 can easily be obtained by double deprotonation of 1 with a strong, non-nucleophilic base like LiHMDS in an aprotic solvent like tetrahydrofuran, typically at −78° C., followed by treatment with allyl bromide, to produce selectively the C-alkylated products 2 (step a). Standard hydrolysis generates intermediate acids 3 (step b), which are then transformed, following well established literature precedence (J. Med. Chem. (1996), 39, 3897), into compounds 4 (step c). Ring-closure to the oxazole using trifluoro-acetic acid and trifluoro-acetic anhydride or Burgess-reagent (methyl-N-triethylammoniosulfonyl-carbamate) generates key intermediates 5 (step d), which, finally, are elaborated via hydroboration to the target alcohols 6, e.g. with 9-BBN in THF and ensuing oxidative work-up with $H_2O_2$ and NaOH (step e). Alternatively, the double bond in 5 can be cleaved oxidatively, e.g. with catalytic amounts of $OsO_4$ and $NaIO_4$ in a mixture of THF, water and tBuOH, to yield, after reduction of the thereby obtained aldehyde, e.g. with $NaBH_4$ in EtOH, the alcohol 7 (step f).

The following tests were carried out in order to determine the activity of the compounds of formula (I).

Background information on the performed assays can be found in: Nichols J S et al. "Development of a scintillation proximity assay for peroxisome proliferator-activated receptor gamma ligand binding domain", (1998) Anal. Biochem. 257: 112–119.

Full-length cDNA clones for human PPARα and mouse PPARγ were obtained by RT-PCR from human adipose and mouse liver cRNA, respectively, cloned into plasmid vectors and verified by DNA sequencing. Bacterial and mammalian expression vectors were constructed to produce glutathione-s-transferase (GST) and Gal4 DNA binding domain proteins fused to the ligand binding domains (LBD) of PPARγ (aa 174 to 476) and PPARα (aa 167 to 469). To accomplish this, the portions of the cloned sequences encoding the LBDs were amplified from the full-length clones by PCR and then subcloned into the plasmid vectors. Final clones were verified by DNA sequence analysis.

Induction, expression, and purification of GST-LBD fusion proteins were performed in *E. coli* strain BL21 (pLysS) cells by standard methods (Ref: Current Protocols in Molecular Biology, Wiley Press, edited by Ausubel et al.).

Radioligand Binding Assay

PPARα receptor binding was assayed in TKE10 (10 mM Tris-HCl, pH 8, 50 mM KCl, 2 mM EDTA, 0.1 mg/ml fatty acid free BSA and 10 mM DTT). For each 96 well 2.4 ug equivalent of GST-PPARα-LBD fusion protein and radioligand, e.g. 40000 dpm 2(S)-(2-benzoyl-phenylamino)-3-{4-[1,1-ditritio-2-(5-methyl-2-phenyl-oxazol-4-yl)-ethoxy]-phenyl}-propionic acid, were incubated in 100 ul volume at RT for 2 hrs. Bound ligand was removed from unbound ligand by solid phase separation using MultiScreen plates (Millipore) filled with 80 ul of SG25 according to the manufacturer's recommendations.

PPARγ receptor binding was assayed in TKE50 (50 mM Tris-HCl, pH 8, 50 mM KCl, 2 mM EDTA, 0.1 mg/ml fatty acid-free BSA and 10 mM DTT). For each 96 well reaction an 140 ng equivalent of GST-PPARγ-LBD fusion protein was bound to 10 ug SPA beads (PharmaciaAmersham) in a final volume of 50 ul by shaking. The resulting slurry was incubated for 1 h at RT and centrifuged for 2 min at 1300 g. The supernatant containing unbound protein was removed and the semidry pellet containig the recptor-coated beads was resolved in 50 ul of TKE. For radioligand binding e.g. 10000 dpm 2(S)-(2-benzoyl-phenylamino)-3-{4-[1,1-ditritio-2-(5-methyl-2-phenyl-oxazol-4-yl)-ethoxy]-phenyl}-propionic acid in 50 ul were added, the reaction incubated at RT for 1 h and scintillation proximity counting performed. All binding assays were performed in 96 well plates and the amount of bound ligand measured on a Packard TopCount using OptiPlates (Packard). Nonspecific binding was determined in the presence of $10^{-4}$ M unlabelled compound. Dose response curves were done in triplicates within a range of concentration from $10^{-10}$ M to $10^{-4}$ M.

Luciferase Transcriptional Reporter Gene Assays

Baby hamster kidney cells (BHK21 ATCC CCL10) were grown in DMEM medium containing 10% FBS at 37° C. in a 95%O2:5%CO$_2$ atmosphere. Cells were seeded in 6 well plates at a density of $10^5$ Cells/well and then batch-transfected with either the pFA-PPARγ-LBD or pFA-PPARα-LBD expression plasmids plus a reporter plasmid and an expression plasmid encoding the secretable form of alkaline phosphatase (SEAP) as a normalization control. Transfection was accomplished with the Fugene 6 reagent (Roche Molecular Biochemicals) according to the suggested protocol. Six hours following transfection, the cells were harvested by trypsinization and seeded in 96 well plates at a density of $10^4$ cells/well. After 24 hours to allow attachment of cells, the medium was removed and replaced with 100 ul of phenol red-free medium containing the test substances or control ligands (final DMSO concentration: 0.1%). Following incubation of the cells for 24 hours with substances, 50 ul of the supernatant was recovered and analyzed for SEAP activity (Roche Molecular Biochemicals). The remainder of the supernatant was discarded, 50 ul PBS was added per well followed by one volume of Luciferase Constant-Light Reagent (Roche Molecular Biochemicals) to lyse the cells and initiate the luciferase reaction. Luminescence for both SEAP and luciferase was measured in a Packard TopCount. Luciferase activity was normalized to the SEAP control and transcriptional activation in the presence of a test substance was expressed as fold-activation over cells incubated in the absence of the substance. EC50 values were calculated using the XLfit program (ID Business Solutions Ltd. UK).

The the free acids of the compounds of the present invention ($R^8$ is hydrogen) exhibit $IC_{50}$ values of 0.1 nM to 50 µM, preferably 1 nM to 10 µM for PPARα and PPARγ. The compounds further exhibit $EC_{50}$ values of 0.1 nM to 50 µM, preferably 1 nM to 10 µM for PPARα and PPARγ. Compounds, in which $R^8$ is not hydrogen are converted in vivo to compounds in which $R^8$ is hydrogen. The following table shows measured values for some selected compounds of the present invention and for a compound already known in the art (e.g.: Rosiglitazone, Drugs 1999, Vol 57(6), 921–930).

|  | PPARα $IC_{50}$ | PPARγ $IC_{50}$ | PPARα $EC_{50}$ | PPARγ $EC_{50}$ |
| --- | --- | --- | --- | --- |
| Example 1 | 53 nmol/l | 153 nmol/l | 35 nmol/l | 237 nmol/l |
| Example 8 | not determined | 69 nmol/l | 27 nmol/l | 19 nmol/l |
| Example 31 | not determined | 202 nmol/l | 62 nmol/l | 80 nmol/l |
| Example 33 | not determined | 162 nmol/l | 6 nmol/l | 67 nmol/l |
| Rosiglitazone | inactive | 1090 nmol/l | inactive | 405 nmol/l |

The compounds of formula (I) and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragees, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula (I) and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragees and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1–500 mg, preferably 0.5–100 mg, of a compound of formula (I).

The following examples serve to illustrate the present invention in more detail. They are, however, not intended to limit its scope in any manner.

EXAMPLES

Abbreviations:

AcOEt=ethyl acetate, 9-BBN=9-borabicyclo[3.3.1]nonane, nBu$_2$BOTf=dibutylboron triflate, DBAD=di-tert-butyl azodicarboxylate, DBU=1,8-diazabicyclo[5.4.0]undec-7-ene, DEAD=diethyl azodicarboxylate, DIAD=diisopropyl azodicarboxylate, DMPU=1,3-dimethyl-3,4,5,6-tetrahydro-2(1H)-pyrimidinone, DMSO=dimethyl sulfoxide, eq.=equivalents, h=hour(s), HPLC=high performance liquid chromatography, LDA=lithium diisopropylamide, min=minute(s), POCl$_3$=phosphorous oxychloride, THF=tetrahydrofuran Example 1 a] 2-tert-Butyl-4,5-dimethyl-oxazole 3-oxide 10.0 g of pivaldehyde (116 mmol) was dissolved in 64 ml of AcOH and treated with 1.00 eq. of diacetyl monooxime (11.7 g). The reaction flask was cooled down to 0° C. and a stream of dry HCl was bubbled for 30 min. through the solution (strongly exothermic). After one additional h, 100 ml of EtOEt was added; however, the product didn't crystallize. Therefore, all solvents were removed by evaporation and the title compound thereby obtained as yellowish oil (30 g, contaminated with AcOH) used as such for the next step.

MS: 170.3 (M+H)$^+$.

b] 2-tert-Butyl-4-chloromethyl-5-methyl-oxazole 30 g of the above prepared 2-tert-butyl-4,5-dimethyl-oxazole 3-oxide (~115 mmol) was dissolved in 390 ml of CH$_2$Cl$_2$ and treated dropwise with 12.74 ml of POCl$_3$ (139 mmol). The reaction mixture was refluxed over night and then quenched by carefully pouring onto crashed ice/3N NaOH. Separation of the layers, additional extraction of the aqueous phase with CH$_2$Cl$_2$, drying of the combined organic phase over sodium sulfate, evaporation of the solvents, and, finally, flash chromatography (SiO$_2$, hexane/AcOEt=85/15) yielded 16.29 g of the title compound as white crystals of mp. 41–44°.

MS: 188.3 (M+H)$^+$.

c] (2-tert-Butyl-5-methyl-oxazol-4-yl)-acetonitrile

To 5.72 g of NaCN (116.8 mmol), dissolved in 77 ml of DMSO, was slowly added via dropping funnel 14.14 g of the above prepared 2-tert-butyl-4-chloromethyl-5-methyl-oxazole (75.3 mmol) at such a rate that the internal temperature stayed at 25–30°. Stirring was continued for an additional 1.5 h at 35°. The reaction mixture was then poured onto crashed ice/AcOEt, the organic layer washed with water, dried over sodium sulfate, and evaporated to dryness. Thereby, 13.19 g of the title product was obtained, which was used without further purification for the next step.

MS: 178.3 (M)$^+$.

d] (2-tert-Butyl-5-methyl-oxazol-4-yl)-acetic acid 13.19 g of the above prepared (2-tert-butyl-5-methyl-oxazol-4-yl)-acetonitrile (74.0 mmol) was dissolved in 170 ml EtOH/water=1/1 and treated with 5 eq. of NaOH-pellets (14.8 g). Hydrolysis was allowed to proceed over night at 65° C. Pouring onto crashed ice/HCl, twofold extraction with AcOEt, washing with water, drying over sodium sulfate, followed by evaporation of the solvents, yielded 13.77 g of the title acid as waxy solid.

MS: 196.1 (M–H)$^-$.

e] 2-(2-tert-Butyl-5-methyl-oxazol-4-yl)-ethanol 13.77 g of the above prepared (2-tert-butyl-5-methyl-oxazol-4-yl)-acetic acid (69.8 mmol) was dissolved in 460 ml of abs. THF and treated at 0° C. with 174.5 ml of 1M BH$_3$.THF (2.5 eq.). The reaction mixture was then kept over night at ambient temperature. Careful quenching with ice, twofold extraction with AcOEt, washing with water, drying over sodium sulfate, and evaporation of the solvents left a crude product which was refluxed for 60 Min. in MeOH to liberate quantitatively the free alcohol. Removing of the solvent and flash chromatography (SiO$_2$, AcOEt) delivered finally 9.23 g of the title compound as colorless oil.

MS: 183.3 (M)$^+$.

f] 4-[2-(2-tert-Butyl-5-methyl-oxazol-4-yl)-ethoxy]-naphthalene-1-carbaldehyde 0.800 g of the above prepared 2-(2-tert-butyl-5-methyl-oxazol-4-yl)-ethanol (4.37 mmol) was dissolved in 25 ml of toluene and treated successively at 0° C. with 0.752 g of 4-hydroxy-naphthalene-1-carbaldehyde (4.37 mmol), 1.145 g of triphenylphosphine (4.37 mmol), and 0.883 g (4.37 mmol) of DIAD. The cooling bath was then removed and stirring continued for 4 h. Pouring onto crashed ice, twofold extraction with EtOEt, washing with dil. NaOH and water, drying over sodium sulfate, and evaporation of the solvents, followed by flash chromatography (SiO$_2$, hexane/AcOEt=6/4) and crystallization from EtOEt, delivered finally 0.791 g of the title compound as off-white crystals of mp. 155–57° (dec.).

MS: 338.3 (M+H)$^+$.

g] (S)-4-Benzyl-3-((2S,3R)-3-{4-[2-(2-tert-butyl-5-methyl-oxazol-4-yl)-ethoxy]-naphthalen-1-yl}-2-ethoxy-3-hydroxy-propionyl)-oxazolidin-2-one 0.234 g of (S)-4-benzyl-3-ethoxyacetyl-oxazolidin-2-one (0.889 mmol) was dissolved under an argon atmosphere in 3 ml of abs. CH$_2$Cl$_2$ and treated with 0.149 ml of triethylamine (1.2 eq.). After cooling to –78°, nBu$_2$BOTf was added slowly (0.980 ml of 1M solution in CH$_2$Cl$_2$) and enolborinate formation allowed to proceed for 15 Min. at –78° and for 50 Min. at 0°. After recooling, a solution of 0.300 g of the above prepared 4-[2-(2-tert-butyl-5-methyl-oxazol-4-yl)-ethoxy]-naphthalene-1-carbaldehyde (0.889 mmol) in 5 ml of abs. CH$_2$Cl$_2$ was slowly added via dropping funnel and the mixture kept for 30 Min. at –78° and for additional 30 Min. at 0°. Pouring onto crashed ice/NH$_4$Cl, twofold extraction with AcOEt, washing with water, drying over magnesium sulfate, and evaporation of the solvents, followed by flash chromatography (silica gel, hexane/AcOEt=1/1) left finally 0.268 g of the title compound as white foam.

MS: 601.4 (M+H)+.

h] (S)-4-Benzyl-3-((S)-3-{4-[2-(2-tert-butyl-5-methyl-oxazol-4-yl)-ethoxy]-naphthalen-1-yl}-2-ethoxy-propionyl)-oxazolidin-2-one 0.267 g of the above prepared (S)-4-benzyl-3-((2S,3R)-3-{4-[2-(2-tert-butyl-5-methyl-oxazol-4-yl)-ethoxy]-naphthalen-1-yl}-2-ethoxy-3-hydroxy-propionyl)-oxazolidin-2-one (0.444 mmol) was dissolved in 1.4 ml of trifluoroacetic acid, treated at 0° with 0.353 ml of triethylsilane (5 eq.) and then kept for 4 h at 0°, when TLC indicated the disappearance of starting material. The reaction mixture was then poured onto crashed ice/AcOEt/NaHCO₃, the organic layer washed with water (pH of aq. phase~8), dried over magnesium sulfate, and evaporated to dryness. Flash chromatography (SiO₂, hexane/AcOEt=65/35) delivered 0.237 g of the title compound as white foam.

MS: 585.4 (M+H)+.

i] (S)-3-{4-[2-(2-tert-Butyl-5-methyl-oxazol-4-yl)-ethoxy]-naphthalen-1-yl}-2-ethoxy-propionic acid 0.237 g of the above prepared (S)-4-benzyl-3-((S)-3-{4-[2-(2-tert-butyl-5-methyl-oxazol-4-yl)-ethoxy]-naphthalen-1-yl}-2-ethoxy-propionyl)-oxazolidin-2-one (0.405 mmol) was dissolved in 3 ml of THF and treated with 1.01 ml of 1N NaOH (2.5 eq.). The reaction mixture was kept at 0° and progress of the hydrolysis followed by TLC. After 1 h the reaction mixture was poured onto crashed ice/AcOEt/HCl dil., the organic layer washed with water, dried over magnesium sulfate, and evaporated to dryness. In order to remove the chiral auxiliary, the crude product was redissolved in EtOEt and extracted with 0.05 N NaOH. The aqueous layer was then acidified with HCl dil., extracted twice with AcOEt, washed with water, dried over magnesium sulfate, and evaporated to dryness. Twofold crystallization from AcOEt/hexane yielded finally 0.111 g of the title product as white crystals of mp. 103–05°.

MS: 424.3 (M–H)−.

Example 2

(S)-2-But-3-enyloxy-3-{4-[2-(2-tert-butyl-5-methyl-oxazol-4-yl)-ethoxy]-naphthalen-1-yl}-propionic acid was prepared in analogy to example 1, but using in step g] (S)-4-benzyl-3-but-3-enyloxyacetyl-oxazolidin-2-one instead of (S)-4-benzyl-3-ethoxyacetyl-oxazolidin-2-one as white foam.

MS: 450.3 (M–H)−.

The necessary building block (S)-4-benzyl-3-but-3-enyloxyacetyl-oxazolidin-2-one was prepared as follows:

a] But-3-enyloxy-acetic acid

To 480 mg of NaH (50% in mineral oil, ~20 mmol) in 10 ml of abs. THF was added at 0° 721 mg of 3-buten-1-ol (10 mmol) and the mixture stirred for 5 Min. (H₂-evolution). 1.39 g of bromo-acetic acid (10 mmol), dissolved in 10 ml of THF, was then added and the mixture kept for additional 5 Min. at 0° and for 2 h at ambient temperature. Pouring onto crashed ice/HCl dil., twofold extraction with AcOEt, washing with brine, drying over sodium sulfate and evaporation of the solvents afforded 1.65 g of the title compound, contaminated with mineral oil, but sufficiently pure for the next step.

b] (S)-4-Benzyl-3-methoxyacetyl-oxazolidin-2-one 1.6 g of the above prepared but-3-enyloxy-acetic acid (9.9 mmol) was treated with 3.35 ml=5.03 g of oxalic acid (4 eq.) and one drop of abs. DMF. Immediate gas-evolution set in and the reaction mixture was kept for 3 h. Careful evaporation of the excess of reagent and drying yielded 1.35 g of acid chloride which was used for the next step without further purification. 1.77 g of (S)-4-Benzyl-2-oxazolidinone (10 mmol) was dissolved in 30 ml of abs. THF and cooled down to −78°. 6.67 ml of 1.5M nBuLi (hexane) was added via syringe (strongly exothermic) to deprotonate the NH. Ten Min. later, the crude, above prepared acid chloride, dissolved in 10 ml of THF, was added and stirring continued for 30 Min. at −78° and for 30 Min at 0°. Pouring onto crashed ice/NH₄Cl, twofold extraction with AcOEt, washing with water, drying over sodium sulfate, and evaporation of the solvents, followed by flash chromatography (SiO₂, hexane/AcOEt=7/3) afforded 0.691 g of the title compound as colorless, viscous oil.

Example 3

(S)-3-{4-[2-(2-tert-Butyl-5-methyl-oxazol-4-yl)-ethoxy]-3,5-dimethyl-phenyl}-2-ethoxy-propionic acid was prepared in analogy to example 1, but using in step f] 3,5-dimethyl-4-hydroxy-benzaldehyde as coupling partner for the Mitsunobu-reaction instead of 4-hydroxy-naphthalene-1-carbaldehyde as colorless oil.

MS: 402.3 (M–H)−.

Example 4

(S)-3-{4-[2-(2-tert-Butyl-5-methyl-oxazol-4-yl)-ethoxy]-3,5-dimethyl-phenyl}-2-propoxy-propionic acid was prepared in analogy to example 3, but using in step g] (S)-4-benzyl-3-propoxyacetyl-oxazolidin-2-one instead of (S)-4-benzyl-3-ethoxyacetyl-oxazolidin-2-one as colorless solid.

MS: 416.2 (M–H)−.

Example 5

(S)-3-{4-[2-(2-tert-Butyl-5-methyl-oxazol-4-yl)-ethoxy]-3,5-dimethyl-phenyl}-2-isopropoxy-propionic acid was prepared in analogy to example 3, but using in step g] (S)-4-benzyl-3-isopropoxyacetyl-oxazolidin-2-one instead of (S)-4-benzyl-3-ethoxyacetyl-oxazolidin-2-one as colorless oil.

MS: 416.2 (M–H)−.

Example 6

(S)-3-{4-[2-(2-tert-Butyl-5-methyl-oxazol-4-yl)-ethoxy]-benzo[b]thiophen-7-yl}-2-ethoxy-propionic acid was prepared in analogy to example 1, but using in step f] 14-hydroxy-benzo[b]thiophene-7-carbaldehyde as coupling partner for the Mitsunobu-reaction instead of 4-hydroxy-naphthalene-1-carbaldehyde as white crystals of mp. 155–56°.

MS: 430.3 (M–H)−.

Example 7

(S)-2-But-3-enyloxy-3-{4-[2-(2-tert-butyl-5-methyl-oxazol-4-yl)-ethoxy]-benzo[b]thiophen-7-yl}-propionic acid was prepared in analogy to example 2, but using in step f] 4-hydroxy-benzo[b]thiophene-7-carbaldehyde as coupling partner for the Mitsunobu-reaction instead of 4-hydroxy-naphthalene-1-carbaldehyde as white crystals of mp. 70–71°.

MS: 456.4 (M–H)−.

Example 8 a] 4-[2-(2-tert-Butyl-5-methyl-oxazol-4-yl)-ethoxy]-benzo[b]thiophene-7-carbaldehyde 0.800 g of the above prepared (example 1, step f]) 2-(2-tert-butyl-5-methyl-oxazol-4-yl)-ethanol (4.37 mmol) was dissolved in 25 ml of toluene and treated successively at 0° C. with 0.778 g of 4-hydroxy-benzo[b]thiophene-7-carbaldehyde (4.37 mmol), 1.145 g of triphenylphosphine (4.37 mmol), and 0.883 g (4.37 mmol) of DIAD. The cooling bath was then removed and stirring continued for 4 h. Pouring onto crashed ice, twofold extraction with EtOEt, washing with dil. NaOH and water, drying over sodium sulfate, and evaporation of the solvents, followed by flash chromatography (SiO$_2$, hexane/AcOEt=6/4) and crystallization from EtOEt, produced finally 0.713 g of the title compound as off-white crystals of mp. 140–42° (dec.).

MS: 344.3 (M+H)$^+$.

b] 3-{4-2-(2-tert-Butyl-5-methyl-oxazol-4-yl)-ethoxy]-benzo[b]thiophen-7-yl}-3-hydroxy-2-isopropoxy-propionic acid ethyl ester LDA-solution in THF was prepared according to standard procedure from 0.300 g of diisopropylamine (2.97 mmol) and 1.69 ml of 1.6 M nBuLi (hexane) in 7 ml of abs. THF at −10°. After cooling to −40°, 0.395 g of ethyl isopropoxyacetate (2.70 mmol), dissolved in 2.6 ml of THF, was added and stirring continued for 15 Min. to complete enolate formation. 0.309 g of the above prepared 4-[2-(2-tert-butyl-5-methyl-oxazol-4-yl)-ethoxy]-benzo[b]thiophene-7-carbaldehyde (0.900 mmol), dissolved in 3.9 ml of THF, was then added at −78° and the mixture kept for another 30 Min. at this temperature. Pouring onto crashed ice/NH$_4$Cl, twofold extraction with AcOEt, washing with water, drying over sodium sulfate, and evaporation of the solvents, followed by flash chromatography (SiO$_2$, hexane/AcOEt=/1) delivered 0.434 g of the title compound(syn/anti-isomers) as yellowish foam.

MS: 490.3 (M+H)$^+$.

c] 3-{4-[2-(2-tert-Butyl-5-methyl-oxazol-4-yl)-ethoxy]-benzo[b]thiophen-7-yl}-2-isopropoxy-propionic acid ethyl ester 0.434 g of the above prepared 3-{4-[2-(2-tert-butyl-5-methyl-oxazol-4-yl)-ethoxy]-benzo[b]thiophen-7-yl}-3-hydroxy-2-isopropoxy-propionic acid ethyl ester (0.886 mmol) was dissolved in 4.5 ml of trifluoroacetic acid, treated at 0° with 1.408 ml of triethylsilane (10 eq.) and then kept for 2 h at 0° under vigorous stirring, when TLC indicated the disappearance of starting material. The reaction mixture was then poured onto crashed ice/AcOEt/NaHCO$_3$, the organic layer washed with water (pH of aq. phase~8), dried over sodium sulfate, and evaporated to dryness. Flash chromatography (SiO$_2$, hexane/AcOEt=8/2) yielded 0.322 g of the title compound as colorless oil.

MS: 474.4 (M+H)$^+$.

d] 3-{4-[2-(2-tert-Butyl-5-methyl-oxazol-4-yl)-ethoxy]-benzo[b]thiophen-7-yl}-2-isopropoxy-propionic acid 0.322 g of the above prepared 3-{4-[2-(2-tert-butyl-5-methyl-oxazol-4-yl)-ethoxy]-benzo[b]thiophen-7-yl}-2-isopropoxy-propionic acid ethyl ester (0.680 mmol) was dissolved in 3.4 ml of THF/EtOH=1/1, treated with 1.133 ml of 3N NaOH (5 eq.), and kept at ambient temperature for 1.5 h. The reaction mixture was then poured onto crashed ice/AcOEt/HCl dil., the organic layer washed with water, dried over sodium sulfate, and evaporated to dryness. Crystallization from hexane/AcOEt afforded finally 0.287 g of the title compound as a white solid of mp. 159–60°.

MS: 444.2 (M−H)$^−$.

Example 9

3-{4-[2-(2-tert-Butyl-5-methyl-oxazol-4-yl)-ethoxy]-benzo[b]thiophen-7-yl}-2-ethoxy-propionic acid was prepared in analogy to example 8, but using in step b] ethyl ethoxyacetate instead of ethyl isopropoxyacetate as white crystals of mp. 152–53°.

MS: 430.4 (M−H)$^−$.

Example 10

3-{4-[2-(2-tert-Butyl-5-methyl-oxazol-4-yl)-ethoxy]-benzo[b]thiophen-7-yl}-2-methoxy-propionic acid was prepared in analogy to example 8, but using in step b] ethyl methoxyacetate instead of ethyl isopropoxyacetate as white crystals of mp. 163–65°.

MS: 416.2 (M−H)$^−$.

Example 11

3-{4-[2-(2-tert-Butyl-5-methyl-oxazol-4-yl)-ethoxy]-naphthalen-1-yl}-2-isopropoxy-propionic acid was prepared in analogy to example 8, but using in step a] 4-hydroxy-naphthalene-1-carbaldehyde instead of 4-hydroxy-benzo[b]thiophene-7-carbaldehyde as colorless foam.

MS: 438.2 (M−H)$^−$.

Example 12

3-{4-[2-(2-tert-Butyl-5-methyl-oxazol-4-yl)-ethoxy]-naphthalen-1-yl}-2-ethoxy-propionic acid was prepared in analogy to example 11, but using in step b] ethyl ethoxyacetate instead of ethyl isopropoxyacetate as white solid.

MS: 424.3 (M−H)$^−$.

Example 13

3-{4-[2-(2-tert-Butyl-5-methyl-oxazol-4-yl)-ethoxy]-naphthalen-1-yl}-2-methoxy-propionic acid was prepared in analogy to example 11, but using in step b] ethyl methoxyacetate instead of ethyl isopropoxyacetate as white crystals of mp. 141–43°.

MS: 410.4 (M−H)$^−$.

Example 14

3-{4-[2-(2-tert-Butyl-5-methyl-oxazol-4-yl)-ethoxy]-naphthalen-1-yl}-2-propoxy-propionic acid was prepared in analogy to example 11, but using in step b] ethyl propoxyacetate instead of ethyl isopropoxyacetate as white crystals of mp. 135–37°.

MS: 438.3 (M−H)$^−$.

Example 15

3-{4-[2-(2-tert-Butyl-5-methyl-oxazol-4-yl)-ethoxy]-3,5-dimethyl-phenyl}-2-methoxy-propionic acid was prepared in analogy to example 13, but using in step a] 3,5-dimethyl-4-hydroxy-benzaldehyde as coupling partner for the Mitsunobu-reaction instead of 4-hydroxy-naphthalene-1-carbaldehyde as white crystals of mp. 78–80°.

MS: 388.1 (M−H)$^−$.

Example 16

3-{4-[2-(2-tert-Butyl-5-methyl-oxazol-4-yl)-ethoxy]-3,5-dimethyl-phenyl}-2-ethoxy-propionic acid was prepared in analogy to example 15, but using in step b] ethyl ethoxy-acetate instead of ethyl methoxyacetate as white crystals of mp. 104–06°.

MS: 402.2 (M−H)⁻.

Example 17

3-{4-[2-(2-tert-Butyl-5-methyl-oxazol-4-yl)-ethoxy]-3-methyl-phenyl}-2-ethoxy-propionic acid was prepared in analogy to example 16, but using in step a] 4-hydroxy-3-methyl-benzaldehyde as coupling partner for the Mitsunobu-reaction instead of 3,5-dimethyl-4-hydroxy-benzaldehyde as colorless oil.

MS: 388.2 (M−H)⁻.

Example 18

3-{4-[2-(2-tert-Butyl-5-methyl-oxazol-4-yl)-ethoxy]-3-methyl-phenyl}-2-isopropoxy-propionic acid was prepared in analogy to example 17, but using in step b] ethyl isopropoxyacetate instead of ethyl ethoxyacetate as colorless oil.

MS: 402.4 (M−H)⁻.

Example 19 a] 4-(2-tert-Butyl-5-methyl-oxazol-4-ylmethoxy)-benzo[b]thiophene-7-carbaldehyde 0.600 g of 2-tert-butyl-4-chloromethyl-5-methyl-oxazole (example 1, step b], 3.197 mmol) was dissolved in 12 ml of acetone and treated successively with 0.570 g of 4-hydroxy-benzo[b]thiophene-7-carbaldehyde (3.197 mmol), 1.146 g of $Cs_2CO_3$ (3.517 mmol), and 0.0265 g of KI (0.16 mmol). The mixture was then refluxed under an atmosphere of Ar. After cooling, the reaction mixture was poured onto crashed ice, extracted twice with AcOEt, the organic layer washed with water, dried over magnesium sulfate, and the solvents removed i.V. Flash chromatography ($SiO_2$, hexane/AcOEt=8/2) yielded 0.901 g of the title compound as white crystals of mp. 119–200.

MS: 330.3 (M+H)⁺.

b] 3-[4-(2-tert-Butyl-5-methyl-oxazol-4-ylmethoxy)-benzo[b]thiophen-7-yl]-2-ethoxy-3-hydroxy-propionic acid ethyl ester LDA-solution in THF was prepared according to standard procedure from 0.180 g of diisopropylamine (1.783 mmol) and 1.080 ml of 1.5 M nBuLi (hexane) in 3 ml of abs. THF at −10°. After cooling to −75°, 0.214 g of ethyl ethoxyacetate (1.62 mmol), dissolved in 1.0 ml of THF, was added and stirring continued for 30 Min. to complete enolate formation. 0.178 g of the above prepared 4-(2-tert-butyl-5-methyl-oxazol-4-ylmethoxy)-benzo[b]thiophene-7-carbaldehyde (0.540 mmol), dissolved in 2.0 ml of THF, was then added at −75° and the mixture kept for another 30 Min. at this temperature. Pouring onto crashed ice/$NH_4Cl$, twofold extraction with AcOEt, washing with water, drying over magnesium sulfate, and evaporation of the solvents, followed by flash chromatography ($SiO_2$, hexane/AcOEt=7/3) afforded 0.201 g of the title compound (syn/anti-isomers) as yellowish oil.

MS: 462.3 (M+H)⁺.

c] 3-[4-(2-tert-Butyl-5-methyl-oxazol-4-ylmethoxy)-benzo[b]thiophen-7-yl]-2-ethoxy-propionic acid ethyl ester 0.200 g of the above prepared 3-[4-(2-tert-butyl-5-methyl-oxazol-4-ylmethoxy)-benzo[b]thiophen-7-yl]-2-ethoxy-3-hydroxy-propionic acid ethyl ester (0.433 mmol) was dissolved in 1.4 ml of trifluoroacetic acid, treated at 0° with 0.688 ml of triethylsilane (10 eq.) and then kept for 6 h at 0° under vigorous stirring. The reaction mixture was then poured onto crashed ice/AcOEt/$NaHCO_3$, the organic layer washed with water (pH of aq. phase ~8), dried over magnesium sulfate, and evaporated to dryness. Flash chromatography ($SiO_2$, hexane/AcOEt=8/2) yielded 0.127 g of the title compound as colorless oil.

MS: 446.3 (M+H)⁺.

d] 3-[4-(2-tert-Butyl-5-methyl-oxazol-4-ylmethoxy)-benzo[b]thiophen-7-yl]-2-ethoxy-propionic acid 0.125 g of the above prepared 3-[4-(2-tert-butyl-5-methyl-oxazol-4-ylmethoxy)-benzo[b]thiophen-7-yl]-2-ethoxy-propionic acid ethyl ester (0.281 mmol) was dissolved in 1.7 ml of THF/EtOH=1/1, treated with 0.840 ml of 1N NaOH (3 eq.), and kept at ambient temperature for 1.0 h. The reaction mixture was then poured onto crashed ice/AcOEt/HCl dil., the aqueous phase reextracted once more with AcOEt, the combined organic layers washed with water, dried over magnesium sulfate, and evaporated to dryness. Crystallization from hexane/AcOEt yielded finally 0.111 g of the title compound as white crystals of mp. 179–80°.

MS: 416.3 (M−H)⁻.

Example 20

3-[4-(2-tert-Butyl-5-methyl-oxazol-4-ylmethoxy)-3,5-dimethyl-phenyl]-2-ethoxy-propionic acid was prepared in analogy to example 19, but using in step a] 3,5-dimethyl-4-hydroxy-benzaldehyde as coupling partner instead of 4-hydroxy-benzo[b]thiophene-7-carbaldehyde as white foam.

MS: 388.3 (M−H)⁻.

Example 21

3-[4-(2-tert-Butyl-5-methyl-oxazol-4-ylmethoxy)-3-methyl-phenyl]-2-ethoxy-propionic acid was prepared in analogy to example 19, but using in step a] 4-hydroxy-3-methyl-benzaldehyde as coupling partner instead of 4-hydroxy-benzo[b]thiophene-7-carbaldehyde as white crystals of mp. 95–97°.

MS: 376.3 (M+H)⁺.

Example 22

3-[4-(2-tert-Butyl-5-methyl-oxazol-4-ylmethoxy)-naphthalen-1-yl]-2-ethoxy-propionic acid was prepared in analogy to example 19, but using in step a] 4-hydroxy-naphthalene-1-carbaldehyde as coupling partner instead of 4-hydroxy-benzo[b]thiophene-7-carbaldehyde as white crystals of mp. 185–86°.

MS: 412.4 (M+H)⁺.

Example 23

3-[4-(2-tert-Butyl-5-methyl-oxazol-4-ylmethoxy)-benzo[b]thiophen-7-yl]-2-isopropoxy-propionic acid was prepared in analogy to example 19, but using in step b] ethyl isopropoxyacetate instead of ethyl ethoxyacetate as white crystals of mp. 166–67°.

MS: 432.3 (M+H)+.

Example 24

3-[4-(2-tert-Butyl-5-methyl-oxazol-4-ylmethoxy)-naphthalen-1-yl]-2-propoxy-propionic acid was prepared in analogy to example 22, but using in step b] ethyl propoxyacetate instead of ethyl ethoxyacetate as white crystals of mp. 169–70°.

MS: 424.3 (M–H)−.

Example 25 a] 2-Cyclohexyl-4,5-dimethyl-oxazole 3-oxide 10.0 g of cyclohexanecarboxaldehyde (89.1 mmol) was dissolved in 49 ml of AcOH and treated with 1.00 eq. of diacetyl monooxime (9.01 g). The reaction flask was cooled down to 0° C. and a stream of dry HCl was bubbled for 30 min. through the solution (strongly exothermic). After one additional h, 100 ml of EtOEt was added; the product separated as oily layer. All solvents were removed by evaporation and the title compound thereby obtained as off-white semisolid (25.1 g, contaminated with small amounts of AcOH), sufficiently pure to be used as such for the next step.

MS: 196.2 (M+H)+.

b] 4-Chloromethyl-2-cyclohexyl-5-methyl-oxazole 25.1 g of the above prepared 2-cyclohexyl-4,5-dimethyl-oxazole 3-oxide (~88.8 mmol) was dissolved in 325 ml of $CH_2Cl_2$ and treated dropwise with 9.755 ml of $POCl_3$ (1.2 eq.). The reaction mixture was refluxed over night and then quenched by carefully pouring onto crashed ice/3N NaOH. Separation of the layers, additional extraction of the aqueous phase with $CH_2Cl_2$, washing with $Na_2CO_3$ and water, drying of the combined organic phase over sodium sulfate, evaporation of the solvents, and, finally, flash chromatography ($SiO_2$, hexane/AcOEt=9/1) afforded 4.12 g of the title compound as yellowish oil, exhibiting in the $^1$H-NMR the typical signal at 4.46 ppm (2H). The other, unstable regioisomer was not isolated.

c] (2-Cyclohexyl-5-methyl-oxazol-4-yl)-acetonitrile

To 1.464 g of NaCN (29.88 mmol), dissolved in 20 ml of DMSO, was slowly added via dropping funnel 4.12 g of the above prepared 4-chloromethyl-2-cyclohexyl-5-methyl-oxazole (19.28 mmol) at such a rate that the internal temperature stayed at 25–30°. Stirring was continued for additional 2 h at 35°. The reaction mixture was then poured onto crashed ice/AcOEt, the organic layer washed with water, dried over sodium sulfate, and evaporated to dryness. Flash chromatography ($SiO_2$, hexane/AcOEt=8/2) gave 1.900 g of the title compound as colorless liquid.

MS: 204.1 (M)+.

d] (2-Cyclohexyl-5-methyl-oxazol-4-yl)-acetic acid 1.900 g of the above prepared (2-cyclohexyl-5-methyl-oxazol-4-yl)-acetonitrile (9.30 mmol) was dissolved in 21 ml EtOH/water=1/1 and treated with 5 eq. of NaOH-pellets (1.86 g). Hydrolysis was allowed to proceed over night at 60° C. After cooling, 25% HCl was added, followed by AcOEt. After separation of the two layers, the aq. phase was again extracted with AcOEt, the combined organic layers washed with water, dried over sodium sulfate, and evaporated to dryness to yield 1.920 g of the title acid as light-brown, waxy solid.

MS: 222.0 (M–H)−.

e] 2-(2-Cyclohexyl-5-methyl-oxazol-4-yl)-ethanol 1.920 g of the above prepared (2-cyclohexyl-5-methyl-oxazol-4-yl)-acetic acid (8.60 mmol) was dissolved in 56 ml of abs. THF and treated at 0° C. with 21.5 ml of 1M $BH_3THF$ (2.5 eq.). The reaction mixture was then kept over weekend at ambient temperature. 3.5 ml of MeOH was added and the mixture stirred for 3 h at ambient temperature and for 3 h at 50° C. to liberate the free alcohol. Removing of the solvents i. V., followed by flash chromatography ($SiO_2$, hexane/AcOEt=4/6) yielded finally 1.314 g of the title compound as colorless oil.

MS: 210.2 (M+H)+.

f] 4-[2-(2-Cyclohexyl-5-methyl-oxazol-4-yl)-ethoxy]-3,5-dimethyl-benzaldehyde 0.400 g of the above prepared 2-(2-cyclohexyl-5-methyl-oxazol-4-yl)-ethanol (1.91 mmol) was dissolved in 10 ml of toluene and treated successively at 0° C. with 0.287 g of 3,5-dimethyl-4-hydroxybenzaldehyde (1.91 mmol), 0.501 g of triphenylphosphine (1.91 mmol), and 0.387 g (1.91 mmol) of DIAD. The cooling bath was then removed and stirring continued for 2 h. Pouring onto crashed ice, twofold extraction with AcOEt, washing with dil. NaOH and water, drying over sodium sulfate, and evaporation of the solvents, followed by flash chromatography ($SiO_2$, hexane/AcOEt=85/15) delivered finally 0.415 g of the title compound as colorless oil.

MS: 342.2 (M+H)+.

g] 3-{4-[2-(2-Cyclohexyl-5-methyl-oxazol-4-yl)-ethoxy]-3,5-dimethyl-phenyl}-3-hydroxy-2-isopropoxy-propionic acid ethyl ester LDA-solution in THF was prepared according to standard procedure from 0.162 g of diisopropylamine (1.60 mmol) and 1.00 ml of 1.5 M nBuLi (hexane) in 3 ml of abs. THF at −10°. After cooling to −78°, 0.219 g of ethyl isopropoxyacetate (1.50 mmol), dissolved in 0.8 ml of THF, was added and stirring continued for 30 Min. to complete enolate formation. 0.169 g of the above prepared 4-[2-(2-cyclohexyl-5-methyl-oxazol-4-yl)-ethoxy]-3,5-dimethyl-benzaldehyde (0.495 mmol), dissolved in 2 ml of THF, was then added at −78° and the mixture kept for 10 Min. at this temperature. Pouring onto crashed ice/$NH_4Cl$, twofold extraction with AcOEt, washing with water, drying over sodium sulfate, and evaporation of the solvents, followed by flash chromatography ($SiO_2$, hexane/AcOEt=65/35) afforded 0.191 g of the title compound (syn/anti-isomers) as colorless, sticky oil.

MS: 488.5 (M+H)+.

h] 3-{4-[2-(2-Cyclohexyl-5-methyl-oxazol-4-yl)-ethoxy]-3,5-dimethyl-phenyl}-2-isopropoxy-propionic acid ethyl ester 0.189 g of the above prepared 3-{4-[2-(2-cyclohexyl-5-methyl-oxazol-4-yl)-ethoxy]-3,5-dimethyl-phenyl}-3-hydroxy-2-isopropoxy-propionic acid ethyl ester (0.388 mmol) was dissolved in 1.5 ml of trifluoroacetic acid, treated at 0° with 0.620 ml of triethylsilane (10 eq.) and then kept for 32 h at RT under vigorous stirring. The reaction mixture was then poured onto crashed ice/AcOEt/$NaHCO_3$, the organic layer washed with water (pH of aq. Phase ~9), dried over sodium sulfate, and evaporated to dryness. Flash chromatography ($SiO_2$, hexane/AcOEt=8/2) produced 0.182 g of the title compound as colorless oil.

MS: 472.4 (M+H)+.

i]3-{4-[2-(2-Cyclohexyl-5-methyl-oxazol-4-yl)-ethoxy]-3,5-dimethyl-phenyl}-2-isopropoxy-propionic acid 0.181 g of the above prepared 3-{4-[2-(2-cyclohexyl-5-methyl-oxazol-4-yl)-ethoxy]-3,5-dimethyl-phenyl}-2-isopropoxy-propionic acid ethyl ester (0.384 mmol) was dissolved in 6 ml of THF/EtOH=1/1, treated with 0.959 ml of 2N NaOH (5 eq.), and kept at ambient temperature for 14 h. The reaction mixture was then poured onto crashed ice/AcOEt/HCl dil., the aqueous phase reextracted once more with AcOEt, the combined organic layers washed with water, dried over magnesium sulfate, and evaporated to dryness. Boiling up in hexane, followed by decantation after cooling, yielded 0.149 g of the title compound as pale-yellow oil.

MS: 442.4 (M–H)$^-$.

Example 26

3-{4-[2-(2-Cyclohexyl-5-methyl-oxazol-4-yl)-ethoxy]-3,5-dimethyl-phenyl}-2-ethoxy-propionic acid was prepared in analogy to example 25, but using in step g] ethyl ethoxyacetate instead of ethyl isopropoxyacetate as colorless oil.

MS: 430.4 (M+H)$^+$.

Example 27

3-{4-[2-(2-Cyclohexyl5-methyl-oxazol-4-yl)-ethoxy-naphthalen-1-yl}-2-ethoxy-propionic acid was prepared in analogy to example 25, but using in step f] 4-hydroxy-naphthalene-1-carbaldehyde as coupling partner instead of 3,5-dimethyl-4-hydroxybenzaldehyde and in step g] ethyl ethoxyacetate instead of ethyl isopropoxyacetate as white solid of mp. 101–04° (dec.).

MS: 452.3 (M+H)$^+$.

Example 28

3-{4-[2-(2-Cyclohexyl-5-methyl-oxazol-4-yl)-ethoxy]-naphthalen-1-yl}-2-propoxy-propionic acid was prepared in analogy to example 27, but using in step g] ethyl propoxyacetate instead of ethyl ethoxyacetate as white solid of mp. 106–07°.

MS: 466.4 (M+H)$^+$.

Example 29

3-{4-[2-(2-Cyclopropyl-5-methyl-oxazol-4-yl)-ethoxy]-naphthalen-1-yl}-2-isopropoxy-propionic acid was prepared in analogy to example 28, but starting the whole reaction sequence in step a] with cyclopropanecarboxaldehyde instead of cyclohexanecarboxaldehyde and using in step g] ethyl isopropoxyacetate instead of ethyl propoxyacetate as off-white foam.

MS: 424.3 (M+H)$^+$.

In step b], both products were isolated and characterized as follows: 36.27 g of 2-cyclopropyl-4,5-dimethyl-oxazole 3-oxide (152 mmol, prepared from cyclohexanecarboxaldehyde and diacetyl monooxime as described above) was dissolved in 555 ml of CH$_2$Cl$_2$ and treated dropwise with 16.75 ml of POCl$_3$ (1.2 eq.). The reaction mixture was refluxed over night and then quenched by carefully pouring onto crashed ice/3N NaOH. Separation of the layers, additional extraction of the aqueous phase with CH$_2$Cl$_2$, washing with Na$_2$CO$_3$ and water, drying of the combined organic phase over sodium sulfate, evaporation of the solvents, and, finally, flash chromatography (SiO$_2$, hexane/AcOEt=9/1) yielded in the less polar fractions 6.53 g of 2-(1,3-dichloro-propyl)-4,5-dimethyl-oxazole (MS: 207.1, 209.1 (M$^+$)) and in the more polar ones 10.33 g of 4-chloromethyl-2-cyclopropyl-5-methyl-oxazole as colorless liquid, exhibiting in the $^1$H-NMR the typical signals at 4.42 ppm (s, 2H), 2.27 (s, 3H), 1.97–2.03 ppm (m, 1H), 0.98–1.04 ppm (m, 4H).

MS: 171.1 (M)$^+$.

Example 30

3-{4-[2-(2-Cyclopropyl-5-methyl-oxazol-4-yl)-ethoxy]-naphthalen-1-yl}-2-ethoxy-propionic acid was prepared in analogy to example 29, but using in step g] ethyl ethoxyacetate instead of ethyl isopropoxyacetate as white foam.

MS: 410.3 (M+H)$^+$.

Example 31

3-{4-[2-(2-Cyclopropyl-5-methyl-oxazol-4-yl)-ethoxy]-benzo[b]thiophen-7-yl}-2-propoxy-propionic acid was prepared in analogy to example 29, but using in step f] 4-hydroxy-benzo[b]thiophene-7-carbaldehyde as coupling partner instead of 4-hydroxy-naphthalene-1-carbaldehyde and in step g] ethyl propoxyacetate instead of ethyl isopropoxyacetate as off-white solid of mp. 61–63°.

MS: 430.3 (M+H)$^+$.

Example 32

3-{4-[2-(2-Cyclopropyl-5-methyl-oxazol-4-yl)-ethoxy]-benzo[b]thiophen-7-yl}-2-ethoxy-propionic acid was prepared in analogy to example 31, but using in step g] ethyl ethoxyacetate instead of ethyl propoxyacetate as white foam.

MS: 416.2 (M+H)$^+$.

Example 33

3-(4-{2-[2-(2,2-Dimethyl-propyl)-5-methyl-oxazol-4-yl]-ethoxy}-naphthalen-1-yl)-2-propoxy-propionic acid was prepared in analogy to example 28, but starting the whole reaction sequence in step a] with 3,3-dimethylbutyraldehyde instead of cyclohexanecarboxaldehyde as colorless oil.

MS: 452.3 (M–H)$^-$.

In this series, reaction step b] yielded an 7/1 mixture in favor of the undesired 2-(1-chloro-2,2-dimethyl-propyl)-4,5-dimethyl-oxazole over the wished-for 4-chloromethyl-2-(2,2-dimethyl-propyl)-5-methyl-oxazole.

Example 34

3-(4-{2-[2-(2,2-Dimethyl-propyl)-5-methyl-oxazol-4-yl]-ethoxy}-naphthalen-1-yl)-2-ethoxy-propionic acid was prepared in analogy to example 33, but using in step g] ethyl ethoxyacetate instead of ethyl propoxyacetate as light yellow foam.

MS: 440.4 (M+H)$^+$.

Example 35

3-{4-[2-(2-tert-Butyl-5-ethyl-oxazol-4-yl)-ethoxy]-benzo[b]thiophen-7-yl}-2-ethoxy-propionic acid was prepared in analogy to example 9, but using for the Mitsunobu-coupling 2-(2-tert-butyl-5-ethyl-oxazol-4-yl)-ethanol instead of 2-(2-tert-butyl-5-methyl-oxazol-4-yl)-ethanol as white crystals of mp. 146–480.

MS: 444.3 (M–H)$^-$.

The former intermediate can be prepared as follows:

a] (2,2-Dimethyl-propionylamino)-acetic acid ethyl ester 10.00 g of glycine ethyl ester hydrochloride (71.6 mmol) and 21.97 ml of NEt$_3$ (2.2 eq.) were dissolved in 210 ml of CH$_2$Cl$_2$ and treated between 0° and 5° dropwise with 9.256 ml of benzoyl chloride (1.05 eq.), dissolved in 30 ml of CH$_2$Cl$_2$. The reaction mixture was allowed to reach ambient temperature (2.5 h) and then quenched by carefully pouring onto crashed ice/HCl/AcOEt. Separation of the layers, additional extraction of the aqueous phase with AcOEt, washing with Na$_2$CO$_3$ and brine, drying of the combined organic phase over sodium sulfate, and evaporation of the solvents left finally 13.06 g of pure title compound as colorless liquid.

MS: 188.3 (M+H)$^+$.

b] 2-(2,2-Dimethyl-propionylamino)-pent-4-enoic acid ethyl ester 13.06 g of the above prepared (2,2-dimethyl-propionylamino)-acetic acid ethyl ester (69.75 mmol) was dissolved in 350 ml of abs. THF and cooled down to –78°. 146 ml of 1M lithium hexamethyldisilazide in THF (2.1 eq.) were slowly added via dropping funnel. After keeping the yellow suspension for 30 Min. at –78°, 6.491 ml of allyl bromide (1.1 eq.) was added and stirring continued for 15 Min. at the same temperature and for 40 Min. at 0°. Pouring of the homogeneous reaction mixture onto crashed ice/HCl, twofold extraction with AcOEt, twofold washing with water, drying over sodium sulfate, and evaporation of the solvents, followed by flash chromatography (SiO$_2$, hexane/AcOEt=8/2) afforded 10.50 g of the title compound as colorless solid. In addition, 2.70 g of the di-allylated product (2-allyl-2-(2,2-dimethyl-propionylamino)-pent-4-enoic acid ethyl ester) was obtained from the less polar fractions.

MS: 228.1 (M+H)$^+$.

c] 2-(2,2-Dimethyl-propionylamino)-pent-4-enoic acid 10.50 g of the above prepared 2-(2,2-dimethyl-propionylamino)-pent-4-enoic acid ethyl ester (46.19 mmol) were dissolved in 146 ml of a 1:1 mixture of EtOH and THF and treated under cooling with an ice bath with 46.19 ml of 2N NaOH (2 eq.). After 1 h, the reaction mixture was poured onto crashed ice/AcOEt/HCl, the aqueous phase reextracted once more with AcOEt, the combined organic layers washed with water, dried over sodium sulfate, and evaporated to dryness. Thereby, 8.45 g of the title product was obtained as white solid of mp. 87–88°.

MS: 198.2 (M–H)$^-$.

d] 2,2-Dimethyl-N-(1-propionyl-but-3-enyl)-propionamide 4.27 g of the above synthesized 2-(2,2-dimethyl-propionylamino)-pent-4-enoic acid (21.43 mmol) were dissolved in 13.5 ml of pyridine with 132.81 ml of propionic anhydride (5 eq.), and heated to 100° for 15 h. After cooling, 10.04 ml of water were added and the mixture kept for 45 Min. at 90°. Careful pouring onto crashed ice/HCl, twofold extraction with AcOEt, washing twice with Na$_2$CO$_3$ and water, drying over sodium sulfate, and evaporation of the solvents, followed by flash chromatography (silica gel, hexane/AcOEt=8/2) left finally 2.10 g of the title compound as yellowish oil.

MS: 212.2 (M–H)$^-$.

e] 4-Allyl-2-tert-butyl-5-ethyl-oxazole 2.10 g of the above prepared 2,2-dimethyl-N-(1-propionyl-but-3-enyl)-propionamide (9.94 mmol) were treated with 16.74 ml of trifluoroacetic acid (219 mmol) and 8.29 ml of trifluoroacetic anhydride (6 eq.) and kept for 4 h at 50°, when TLC indicated the disappearance of starting material. The reaction mixture was then poured onto crashed ice/Na$_2$CO$_3$, the aqueous layer (pH ~8), extracted twice with AcOEt, washed with water, dried over sodium sulfate, and evaporated to dryness. Flash chromatography (SiO$_2$, hexane/AcOEt=95/5) delivered 1.29 g of the title compound as yellowish liquid.

MS: 194.3 (M+H)$^+$.

f] 2-(2-tert-Butyl-5-ethyl-oxazol-4-yl)-ethanol 0.596 g of the above prepared 4-allyl-2-tert-butyl-5-ethyl-oxazole (3.083 mmol) were dissolved in 10 ml of THF and 4 ml of water. 0.387 ml of a 2.5% OsO$_4$ solution in tBuOH (0.01 eq.) and 1.405 g of NaIO$_4$ (2.13 eq.) were added, and the exothermic reaction allowed to proceed for 30 Min. After TLC-check, the reaction mixture was poured onto crashed ice, extracted twice with AcOEt, washed with water, dried over sodium sulfate, and evaporated to dryness to provide ~0.6 g of crude aldehyde. This was redissolved in 9 ml of EtOH and reduced by adding 0.233 g of NaBH$_4$ (2 eq.) at 0°. After 1 h at the same temperature, standard work-up delivered after final purification by flash chromatography (SiO$_2$, hexane/AcOEt=1/1) 0.386 g of the title compound as colorless oil.

MS: 198.3 (M+H)$^+$.

Example 36

3-(4-{2-[2-(2,2-Dimethyl-propyl)-5-methyl-oxazol-4-yl]-ethoxy}-benzo[b]thiophen-7-yl)-2-ethoxy-propionic acid was prepared in analogy to example 34, but using for the Mitsunobu-coupling 4-hydroxy-benzo[b]thiophene-7-carbaldehyde as coupling partner instead of 4-hydroxy-naphthalene-1-carbaldehyde as colorless foam.

MS: 446.3 (M+H)$^+$.

Example 37

3-(4-{2-[2-(2,2-Dimethyl-propyl)-5-methyl-oxazol-4-yl]-ethoxy}-benzo[b]thiophen-7-yl)-2-isopropoxy-propionic acid was prepared in analogy to example 36, using in the aldol-step ethyl isopropoxyacetate instead of ethyl propoxyacetate as off-white foam.

MS: 460.4 (M+H)$^+$.

Example 38

3-[4-(2-Cyclopropyl-5-methyl-oxazol-4-ylmethoxy)-naphthalen-1-yl]-2-ethoxy-propionic acid was prepared in analogy to example 22, but starting the whole reaction sequence with cyclopropanecarboxaldehyde instead of pivaldehyde, as white solid of mp. 166–68°.

MS: 394.2 (M–H)$^-$.

Example 39

3-[4-(2-Cyclopropyl-5-methyl-oxazol-4-ylmethoxy)-naphthalen-1-yl]-2-propoxy-propionic acid was prepared in analogy to example 38, using in the aldol-step ethyl propoxyacetate instead of ethyl ethoxyacetate as white solid of mp. 116–190.

MS: 408.3 (M–H)$^-$.

Example 40

3-[4-(2-Cyclopropyl-5-methyl-oxazol-4-ylmethoxy)-naphthalen-1-yl]-2-isopropoxy-propionic acid was prepared in analogy to example 38, using in the aldol-step ethyl isopropoxyacetate instead of ethyl ethoxyacetate as white solid of mp. 129–30°.
MS: 408.3 (M–H)⁻.

Example 41

3-[4-(2-Cyclopropyl-5-methyl-oxazol-4-ylmethoxy)-benzo[b]thiophen-7-yl]-2-propoxy-propionic acid was prepared in analogy to example 39, but using for the Mitsunobu-coupling 4-hydroxy-benzo[b]thiophene-7-carbaldehyde as coupling partner instead of 4-hydroxy-naphthalene-1-carbaldehyde as white solid of mp. 88–89'.
MS: 414.2 (M–H)⁻.

Example 42

3-[4-(2-Cyclopropyl-5-methyl-oxazol-4-ylmethoxy)-benzo[b]thiophen-7-yl]-2-isopropoxy-propionic acid was prepared in analogy to example 41, using in the aldol-step ethyl isopropoxyacetate instead of ethyl propoxyacetate as off-white solid of mp. 71–72°.
MS: 414.2 (M–H)⁻.

Example 43

3-[4-(2-Cyclopropyl-5-methyl-oxazol-4-ylmethoxy)-benzo[b]thiophen-7-yl]-2-ethoxy-propionic acid was prepared in analogy to example 41, using in the aldol-step ethyl ethoxyacetate instead of ethyl propoxyacetate as white solid of mp. 153–54°.
MS: 400.1 (M–H)⁻.

Example 44

3-[4-(2-tert-Butyl-5-methyl-oxazol-4-ylmethoxy)-3,5-dimethyl-phenyl]-2-isopropoxy-propionic acid was prepared in analogy to example 23, but using for the Mitsunobu-coupling 3,5-dimethyl-4-hydroxy-benzaldehyde as coupling partner instead of 4-hydroxy-benzo[b]thiophene-7-carbaldehyde as colorless, viscous oil.
MS: 402.4 (M–H)⁻.

Example 45

3-[4-(2-tert-Butyl-5-methyl-oxazol-4-ylmethoxy)-3-methyl-phenyl]-2-propoxy-propionic acid was prepared in analogy to example 21, but using in the aldol-step ethyl propoxyacetate instead of ethyl ethoxyyacetate as colorless, viscous oil.
MS: 388.3 (M–H)⁻.

Example 46 a] 3-(4-Benzyloxy-2-methyl-phenyl)-2(Z,E)-ethoxy-acrylic acid ethyl ester
A suspension of (1,2-diethoxy-2-oxoethyl)triphenyl phosphonium chloride [Tetrahedron 50(25), 7543–56(1994)] (35.5 g, 82.9 mmol) and DBU (13.6 ml, 91.2 mmol) in THF (60 ml) was stirred for 10 min at ambient temperature. 4-Benzyloxy-2-methyl-benzaldehyde (12.5 g, 55.2 mmol) was added and the reaction mixture was heated under reflux for 16 h. The solvent was concentrated at reduced pressure, the residue was taken up in AcOEt and washed with saturated aqueous NH₄Cl solution and brine. The organic layer was dried over sodium sulfate, the solvent removed under reduced pressure and the residue purified by column chromatography (silica gel, hexane/AcOEt) to give 14.5 g (42.6 mmol, 77%) of the title compound as yellow liquid.
MS: 340.2 (M)⁺, 249.2, 147.1, 91.1.

b] [rac]-2 Ethoxy-3-(4-hydroxy-2-methyl-phenyl)-propionic acid ethyl ester
A solution of 3-(4-benzyloxy-2-methyl-phenyl)-2(Z,E)-ethoxy-acrylic acid ethyl ester (1 g, 2.9 mmol) in ethanol (50 ml) was hydrogenated over 10% palladium on charcoal (250 mg) at ambient temperature for 2 h. The catalyst was filtered off and the solvent evaporated under reduced pressure to give 600 mg (2.4 mmol, 81%) of the title compound as yellow liquid which was used in the next step without further purification.
MS: 270.4 (M+NH₄)⁺, 253 (M)⁺, 207.2, 165.3.

c] [rac]-3-[4-(2-tert-Butyl-5-methyl-oxazol-4-ylmethoxy)-2-methyl-phenyl]-2-ethoxy-propionic acid ethyl ester
A mixture of [rac]-2-ethoxy-3-(4-hydroxy-2-methyl-phenyl)-propionic acid ethyl ester (50 mg, 0.2 mmol), 2-tert-butyl-4-chloromethyl-5-methyl-oxazole (41 mg, 0.22 mmol, example 1, step b]), cesium carbonate (71 mg, 0.22 mmol) and a trace of potassium iodide were suspended in acetone (5 ml). The suspension was heated under reflux for 14 h, the solvent evaporated under reduced pressure and the residue dissolved in 2 N HCl/ice water 1/1 and ethyl acetate. The layers were separated and the aqueous layer was extracted two times with ethyl acetate. The combined organic layers were washed two times with brine and dried over sodium sulfate. The solvent was removed under reduced pressure and the residue purified by column chromatography (silica gel, cyclohexane/AcOEt) to give 50 mg (0.12 mmol, 63%) of the title compound as colorless oil.
MS: 426.3 (M+Na)⁺, 404.4 (M+H)⁺, 361.3, 291.4, 225.4, 152.2.

d] [rac]-3-[4-(2-tert-Butyl-5-methyl-oxazol-4-ylmethoxy)-2-methyl-phenyl]-2-ethoxy-propionic acid
To a solution of [rac]-3-[4-(2-tert-butyl-5-methyl-oxazol-4-ylmethoxy)-2-methyl-phenyl]-2-ethoxy-propionic acid ethyl ester (50 mg, 0.124 mmol) in THF/methanol 2/1 (0.75 ml) was added a 1 N aqueous LiOH solution (0.75 ml, 0.72 mmol). The reaction mixture was stirred for 2 h at ambient temperature, neutralized with 1 N aqueous HCl solution under ice cooling and concentrated under reduced pressure. The residue was dissolved in 1 N HCl/ice water 1/1 and ethyl acetate, the layers were separated and the aqueous layer was extracted with ethyl acetate. The combined organic layers were washed with ice water/brine 1/1, dried over sodium sulfate and the solvent was evaporated in vacuo to give the title compound (44 mg, 0.117 mmol, 95%) as colorless crystals.
MS: 374.1 (M–H)⁻, 328.2, 281.0, 229.2.

Example 47 a] [rac]-3-{4-[2-(2-tert-Butyl-5-methyl-oxazol-4-yl)-ethoxy]-2-methyl-phenyl}-2-ethoxy-propionic acid ethyl ester
In analogy to the Mitsunobu-procedure described in example 1, step f, [rac]-2-ethoxy-3-(4-hydroxy-2-methyl-phenyl)-propionic acid ethyl ester (example 46 b]) was reacted with 2-(2-tert-butyl-5-methyl-oxazol-4-yl)-ethanol (example 1, step e]) in the presence of triphenylphosphine and di-tert-butyl azodicarboxylate to yield [rac]-3-{4-[2-(2-tert-butyl-5-methyl-oxazol-4-yl)-ethoxy]-2-methyl-phenyl}-2-ethoxy-propionic acid ethyl ester as colorless oil.

MS: 440.4 (M+Na)+, 418.4 (M+H)+, 374.4, 349.4, 282.3, 226.3.

b] [rac]-3-{4-[2-(2-tert-Butyl-5-methyl-oxazol-4-yl)-ethoxy-2-methyl-phenyl}-2-ethoxy-propionic acid In analogy to the procedure described in example 46 d], [rac]-3-{4-[2-(2-tert-butyl-5-methyl-oxazol-4-yl)-ethoxy]-2-methyl-phenyl}-2-ethoxy-propionic acid ethyl ester was treated with LiOH to obtain [rac]-3-{4-[2-(2-tert-butyl-5-methyl-oxazol-4-yl)-ethoxy]-2-methyl-phenyl}-2-ethoxy-propionic acid as colorless liquid.

MS: 388.1 (M–H)−, 341.9, 310.9, 254.9.

Example 48 a] 1-Ethyl-3-(phenylmethoxy)-benzene

To a suspension of potassium carbonate (17 g, 123 mmol) in N,N-dimethylformamide (40 ml) was added a solution of 3-ethyl-phenol (14.8 ml, 123 mmol) in N,N-dimethylformamide (40 ml) at 2° C. under an argon atmosphere. After stirring for 50 min at 2° C., benzyl bromide (14.6 ml, 123 mmol) was added over a period of 15 min at 2° C. The suspension was stirred for additional 30 min at 2° C. and for 12 h at ambient temperature. After adding ice water (250 ml), the solution was extracted two times with diethyl ether. The combined extracts were washed two times with brine and dried over sodium sulfate. Evaporation of the solvent gave a yellow oil which was purified by column chromatography (silica gel, cyclohexane) to yield 24.3 g (114 mmol, 93%) of the title compound as yellow liquid.

MS: 212.2 (M+H)+, 183.1, 91.2, 65.1.

b] 1-Bromo-2-ethyl-4-(phenylmethoxy)-benzene

To a solution of 1-ethyl-3-(phenylmethoxy)-benzene (15 g, 71 mmol) in THF (200 ml) were added N-bromosuccinimide (16.3 g, 92 mmol) and concentrated sulfuric acid (2.4 ml). The solution was stirred for 5 h at ambient temperature. Sodium bicarbonate (3.6 g) and 10% aqueous NaHSO₃ solution. (400 ml) were added under ice cooling. The resulting mixture was stirred for 10 min and then poured into ethyl acetate. The phases were separated and the aqueous phase was extracted with ethyl acetate. The combined extracts were washed with ice water and brine and dried over sodium sulfate. Removal of the solvent under reduced pressure gave a yellow oil which was purified by column chromatography (silica gel, cyclohexane) to yield 17.1 g (58.7 mmol, 83%) of the title compound as colorless liquid.

MS: 292.0 (M)+, 290.0 (M)+, 212.2, 91.1, 65.2.

c] 4-Benzyloxy-2-ethyl-benzaldehyde

A 1.6 M solution of n-BuLi in hexane (44.4 ml, 69.9 mmol) was added within 10 min to a stirred cooled (−85° C.) solution of 1-bromo-2-ethyl-4-(phenylmethoxy)-benzene (18.5 g, 63.5 mmol) in dry THF (22 ml). The mixture was stirred for 1 h at −85° C. under an argon atmosphere. N,N-Dimethylformamide (25.5 ml, 330.4 mmol) was added and the temperature was allowed to rise slowly to room temperature. An aqueous saturated NH₄Cl solution (70 ml) was added under ice cooling. The mixture was extracted two times with dichloromethane, the combined extracts were washed with brine and dried over sodium sulfate. Removal of the solvent under reduced pressure gave a yellow oil which was purified by column chromatography (silica gel, cyclohexane/AcOEt) to yield 11.9 g (49.5 mmol, 78%) of the title compound as yellow oil.

MS: 240.1 (M+H)+, 91.1, 77.1, 65.2.

d] (S)-4-Benzyl-3-[(2S,3R)-3-(4-benzyloxy-2-ethyl-phenyl)-2-ethoxy-3-hydroxy-propionyl]-oxazolidin-2-one (S)-4-Benzyl-3-ethoxyacetyl-oxazolidin-2-one (6.21 g, 24 mmol) (for the preparation of (S)-4-benzyl-3-ethoxyacetyl-oxazolidin-2-one see: D. Haigh, H. C. Birrell, B. C. C. Cantello, D. S. Eggleston, R. C. Haltiwanger, R. M. Hindley, A. Ramaswamy, N. C. Stevens, *Tetrahedron: Asymmetry* 1999, 10, 1353–1367) was dissolved in dry dichloromethane (135 ml) under an argon atmosphere and the solution was cooled to −78° C. Triethylamine (3.98 ml, 28 mmol) was added, followed by the slow addition, over approximately 20 min, of di-n-butylboron triflate (1 M solution in dichloromethane, 25 ml, 25 mmol) such that the reaction temperature was kept below −70° C. The mixture was stirred at −78° C. for 50 min, the cooling bath was replaced with an ice bath and the mixture stirred at 0° C. for additional 50 min before being recooled to −78° C. A solution of 4-benzyloxy-2-methyl-benzaldehyde (6 g, 24 mmol) in dry dichloromethane (65 ml) was added over ca. 45 min, such that the reaction temperature was maintained below −70° C. The resulting mixture was stirred at −78° C. for 45 min, warmed from −78° C. to 0° C. and stirred at 0° C. for a further 1.5 h. The reaction mixture was poured onto ice water/brine and extracted two times with dichloromethane. The combined extracts were washed with brine and dried over sodium sulfate. The solvent was removed under reduced pressure and the residue purified by column chromatography (silica gel, cyclohexane/AcOEt) to give 6.9 g (13.7 mmol, 58%) of the title compound as yellow foam. According to ¹H-NMR spectroscopy, one of the four isomers is strongly predominating. The configuration was tentatively assigned as 2S,3R according to D. Haigh et al., *Tetrahedron: Asymmetry* 1999, 10, 1353–1367.

MS: 526.3 (M+Na)+, 521.3 (M+NH₄)+, 486.2, 381.2, 309.2, 281.2, 253.3, 178.1.

e] (2S,3R)-3-(4-Benzyloxy-2-ethyl-phenyl)-2-ethoxy-3-hydroxy-propionic acid methyl ester A 5.4 M solution of sodium methoxide (640 µl, 3.5 mmol) was added to an ice-cooled and stirred suspension of (S)-4-benzyl-3-[(2S,3R)-3-(4-benzyloxy-2-ethyl-phenyl)-2-ethoxy-3-hydroxy-propionyl]-oxazolidin-2-one (1.58 g, 3.1 mmol) in dry methanol (9 ml). The mixture was stirred at 0° C. for 15 min, quenched and neutralized by the addition of dilute aqueous hydrochloric acid (1.0 M). The solution was concentrated under reduced pressure and the residue dissolved in ice water/ethyl acetate 1/1. The layers were separated and the aqueous layer was extracted two times with ethyl acetate. The combined organic layers were washed with ice water and dried over sodium sulfate. The solvent was removed under reduced pressure and the residue purified by column chromatography (silica gel, cyclohexane/AcOEt) to give 730 mg (2.0 mmol, 65%) of the title compound as colorless liquid. According to ¹H-NMR spectroscopy, one single diastereomer was obtained.

MS: 381.2 (M+Na)+, 376.3 (M+NH₄)+, 341.3, 295.3, 253.2, 225.3.

f] (2S)-3-(4-Benzyloxy-2-ethyl-phenyl)-2-ethoxy-propionic acid methyl ester

Triethylsilane (3.2 ml, 20 mmol) was added to a vigorously stirred, ice-cooled solution of (2S,3R)-3-(4-benzyloxy-2-ethyl-phenyl)-2-ethoxy-3-hydroxy-propionic acid methyl ester (720 mg, 2 mmol) in trifluoroacetic acid (10 ml) under an argon atmosphere. The mixture was stirred at 0° C. for 30 min and for additional 2 h at ambient temperature. The solution was poured onto crashed ice and extracted with ethyl acetate. The organic layer was washed two times with water and neutralized with saturated aqueous sodium bicarbonate solution. The ethyl acetate layer was washed with brine and dried over sodium sulfate. The solvent was removed under reduced pressure to give a colorless oil which was purified by column chromatography (silica gel, cyclohexane/AcOEt) to yield 390 mg (1.1 mmol, 57%) of the title compound as colorless liquid.

MS: 365.2 (M+Na)$^+$, 360.2 (M+NH$_4$)$^+$, 297.3, 283.2, 237.2, 209.3, 181.2.

g] (2S)-2-Ethoxy-3-(2-ethyl-4-hydroxy-phenyl)-propionic acid methyl ester

In analogy to the procedure described in example 46 b], (2S)-3-(4-benzyloxy-2-ethyl-phenyl)-2-ethoxy-propionic acid methyl ester was hydrogenated over 10% palladium on charcoal to give (2S)-2-ethoxy-3-(2-ethyl-4-hydroxy-phenyl)-propionic acid methyl ester as colorless liquid.

MS: 275.2 (M+Na)$^+$, 270.3 (M+NH$_4$)$^+$, 253.3 (M+H)$^+$, 207.2, 175.2, 165.3, 147.2.

h] (S)-3-[4-(2-tert-Butyl-5-methyl-oxazol-4-ylmethoxy)-2-ethyl-phenyl]-2-ethoxy-propionic acid methyl ester In analogy to the procedure described in example 46 c], (2S)-2-ethoxy-3-(2-ethyl-4-hydroxy-phenyl)-propionic acid methyl ester was reacted with 2-tert-butyl-4-chloromethyl-5-methyl-oxazole (example 1, step b]) in the presence of cesium carbonate and potassium iodide to yield (S)-3-[4-(2-tert-butyl-5-methyl-oxazol-4-ylmethoxy)-2-ethyl-phenyl]-2-ethoxy-propionic acid methyl ester as colorless liquid.

MS: 426.4 (M+Na)$^+$, 404.4 (M+H)$^+$, 385.2, 267.4, 208.3, 152.2.

i] (S)-3-[4-(2-tert-Butyl-5-methyl-oxazol-4-ylmethoxy)-2-ethyl-phenyl]-2-ethoxy-propionic acid In analogy to the procedure described in example 46 d], (S)-3-[4-(2-tert-butyl-5-methyl-oxazol-4-ylmethoxy)-2-ethyl-phenyl]-2-ethoxy-propionic acid methyl ester was treated with LiOH to obtain (S)-3-[4-(2-tert-butyl-5-methyl-oxazol-4-ylmethoxy)-2-ethyl-phenyl]-2-ethoxy-propionic acid as colorless solid.

MS: 412.3 (M+Na)$^+$, 390.2 (M+H)$^+$, 338.2, 267.2, 222.3, 193.4, 152.2.

Example 49 a] (S)-4-Benzyl-3-[(2S,3R)-3-(4-benzyloxy-2-chloro-phenyl)-2-ethoxy-3-hydroxy-propionyl]-oxazolidin-2-one In analogy to the procedure described in example 48 d], (S)-4-benzyl-3-ethoxyacetyl-oxazolidin-2-one (for the preparation of (S)-4-benzyl-3-ethoxyacetyl-oxazolidin-2-one see: D. Haigh, H. C. Birrell, B. C. C. Cantello, D. S. Eggleston, R. C. Haltiwanger, R. M. Hindley, A. Ramaswamy, N. C. Stevens, Tetrahedron: Asymmetry 1999, 10,1353–1367) was reacted with 4-benzyloxy-2-chloro-benzaldehyde (for the preparation of 4-benzyloxy-2-chloro-benzaldehyde see: T. Kimachi, M. Kawase, S. Matsuki, K. Tanaka, F. Yoneda, J. Chem. Soc., Perkin Trans. 1 1990, 253–256) in the presence of triethylamine and di-n-butyl-boron triflate to give (S)-4-benzyl-3-[(2S,3R)-3-(4-benzyloxy-2-chloro-phenyl)-2-ethoxy-3-hydroxy-propionyl]-oxazolidin-2-one as colorless liquid. According to $^1$H-NMR spectroscopy, one of the four isomers is strongly predominating. The configuration was tentatively assigned as 2S,3R according to D. Haigh et al., Tetrahedron: Asymmetry 1999, 10, 1353–1367.

MS: 532.3 (M+Na)$^+$, 527.2 (M+NH$_4$)$^+$, 446.1, 381.2, 315.1, 287.2, 243.2, 178.2.

b] (2S,3R)-3-(4-Benzyloxy-2-chloro-phenyl)-2-ethoxy-3-hydroxy-propionic acid methyl ester In analogy to the procedure described in example 48 e], (S)-4-benzyl-3-[(2S,3R)-3-(4-benzyloxy-2-chloro-phenyl)-2-ethoxy-3-hydroxy-propionyl]-oxazolidin-2-one was treated with sodium methoxide in methanol to give (2S,3R)-3-(4-benzyloxy-2-chloro-phenyl)-2-ethoxy-3-hydroxy-propionic acid methyl ester as colorless liquid. According to $^1$H-NMR spectroscopy, one single diastereomer was obtained.

MS: 387.1 (M+Na)$^+$, 382.2 (M+NH$_4$)$^+$, 328.2, 319.2, 279.2, 203.2.

c] (2S)-3-(4-Benzyloxy-2-chloro-phenyl)-2-ethoxy-propionic acid methyl ester

In analogy to the procedure described in example 48 f], (2S,3R)-3-(4-benzyloxy-2-chloro-phenyl)-2-ethoxy-3-hydroxy-propionic acid methyl ester was treated with triethylsilane in trifluoroacetic acid to yield (2S)-3-(4-benzyloxy-2-chloro-phenyl)-2-ethoxy-propionic acid methyl ester as colorless liquid.

MS: 371.4 (M+Na)$^+$, 366.2 (M+NH$_4$)$^+$, 303.2, 269.2, 222.2, 187.2.

d] (2S)-3-(2-Chloro-4-hydroxy-phenyl)-2-ethoxy-propionic acid methyl ester

Dimethyl sulfide (5.8 ml, 79 mmol) and boron trifluoride diethyl etherate (46% purity, 4.3 ml, 16 mmol) were added to a ice cold solution of (2S)-3-(4-benzyloxy-2-chloro-phenyl)-2-ethoxy-propionic acid methyl ester (1.1 g, 3.2 mmol) in dichloromethane (34 ml) under an argon atmosphere. The mixture was stirred for 5 h at ambient temperature, poured into ice water/brine 1/1 and extracted two times with dichloromethane. The combined extracts were washed with ice water/brine 1/1 and dried over sodium sulfate. Removal of the solvent under reduced pressure gave a colorless oil which was purified by column chromatography (silica gel, cyclohexane/AcOEt) to yield 0.6 g (2.3 mmol, 74%) of the title compound as colorless oil.

MS: 281.0 (M+Na)$^+$, 276.1 (M+NH$_4$)$^+$, 251.3, 213.3, 187.2.

e] (S)-3-[4-(2-tert-Butyl-5-methyl-oxazol-4-ylmethoxy)-2-chloro-phenyl]-2-ethoxy-propionic acid methyl ester In analogy to the procedure described in example 46 c], (2S)-3-(2-chloro-4-hydroxy-phenyl)-2-ethoxy-propionic acid methyl ester was reacted with 2-tert-butyl-4-chloromethyl-5-methyl-oxazole (example 1, step b]) in the presence of cesium carbonate and potassium iodide to yield (S)-3-[4-(2-tert-butyl-5-methyl-oxazol-4-ylmethoxy)-2-chloro-phenyl]-2-ethoxy-propionic acid methyl ester as colorless liquid.

MS: 432.4 (M+Na)$^+$, 410.4 (M+H)$^+$, 365.2, 331.1, 267.1, 225.0.

f] (S)-3-[4-(2-tert-Butyl-5-methyl-oxazol-4-ylmethoxy)-2-chloro-phenyl]-2-ethoxy-propionic acid In analogy to the procedure described in example 46 d], (S)-3-[4-(2-tert-butyl-5-methyl-oxazol-4-ylmethoxy)-2-chloro-phenyl]-2-ethoxy-propionic acid methyl ester was treated with LiOH to obtain (S)-3-[4-(2-tert-butyl-5-methyl-oxazol-4-ylmethoxy)-2-chloro-phenyl]-2-ethoxy-propionic acid as colorless solid.

MS: 394.3 (M−H)$^−$, 347.9, 309.5, 267.4, 206.7, 168.7, 152.4.

Example 50 a] (S)-4-Benzyl-3-[(2S,3R)-3-(4-benzyloxy-2-methoxy-phenyl)-2-ethoxy-3-hydroxy-propionyl]-oxazolidin-2-one In analogy to the procedure described in example 48 d], (S)-4-benzyl-3-ethoxyacetyl-oxazolidin-2-one (for the preparation of (S)-4-benzyl-3-ethoxyacetyl-oxazolidin-2-one see: D. Haigh, H. C. Birrell, B. C. C. Cantello, D. S. Eggleston, R. C. Haltiwanger, R. M. Hindley, A. Ramaswamy, N. C. Stevens, *Tetrahedron: Asymmetry* 1999, 10, 1353–1367) was reacted with 4-benzyloxy-2-methoxy-benzaldehyde in the presence of triethylamine and di-n-butylboron triflate to give (S)-4-benzyl-3-[(2S,3R)-3-(4-benzyloxy-2-methoxy-phenyl)-2-ethoxy-3-hydroxy-propionyl]-oxazolidin-2-one as light yellow solid. According to $^1$H-NMR spectroscopy, one of the four isomers is strongly predominating. The configuration was tentatively assigned as 2S,3R according to D. Haigh et al., *Tetrahedron: Asymmetry* 1999, 10, 1353–1367.

MS: 528.3 $(M+Na)^+$, 523.3 $(M+NH_4)^+$, 488.3, 442.4, 311.2, 239.3.

b] (2S,3R)-3-(4-Benzyloxy-2-methoxy-phenyl)-2-ethoxy-3-hydroxy-propionic acid methyl ester In analogy to the procedure described in example 48 e], (S)-4-benzyl-3-[(2S,3R)-3-(4-benzyloxy-2-methoxy-phenyl)-2-ethoxy-3-hydroxy-propionyl]-oxazolidin-2-one was treated with sodium methoxide in methanol to give (2S,3R)-3-(4-benzyloxy-2-methoxy-phenyl)-2-ethoxy-3-hydroxy-propionic acid methyl ester as colorless liquid. According to $^1$H-NMR spectroscopy, one single diastereomer was obtained.

MS: 383.2 $(M+Na)^+$, 378.2 $(M+NH_4)^+$, 343.2, 311.2, 283.2, 239.3, 163.2.

c] (2S)-2-Ethoxy-3-(4-hydroxy-2-methoxy-phenyl)-propionic acid methyl ester

A solution of (2S,3R)-3-(4-benzyloxy-2-methoxy-phenyl)-2-ethoxy-3-hydroxy-propionic acid methyl ester (100 mg, 200 μmol) and oxalic acid dihydrate (150 mg, 1.2 mmol) in isopropanol (2 ml) was hydrogenated at a pressure of 50 atmospheres over 10% palladium on charcoal (20 mg) at ambient temperature for 6.5 h. The catalyst was filtered off and the solvent evaporated under reduced pressure. The residue was dissolved in ice water/aqueous sodium bicarbonate solution 1/1 and extracted two times with ethyl acetate. The combined extracts were washed two times with ice water/brine 1/1 and dried over sodium sulfate. The solvent was removed under reduced pressure to give a yellow liquid which was purified by column chromatography (silica gel, cyclohexane/AcOEt) to yield 43 mg (170 μmol, 85%) of the title compound as light yellow liquid.

MS: 277.1 $(M+Na)^+$, 209.2, 195.3, 181.2, 177.2, 167.2.

d] (S)-3-[4-(2-tert-Butyl-5-methyl-oxazol-4-ylmethoxy)-2-methoxy-phenyl]-2-ethoxy-propionic acid methyl ester In analogy to the procedure described in example 46 c], (2S)-2-ethoxy-3-(4-hydroxy-2-methoxy-phenyl)-propionic acid methyl ester was reacted with 2-tert-butyl-4-chloromethyl-5-methyl-oxazole (example 1, step b]) in the presence of cesium carbonate and potassium iodide to yield (S)-3-[4-(2-tert-butyl-5-methyl-oxazol-4-ylmethoxy)-2-methoxy-phenyl]-2-ethoxy-propionic acid methyl ester as colorless liquid.

MS: 428.4 $(M+Na)^+$, 406.3 $(M+H)^+$, 360.3, 249.2, 209.3, 152.2.

e] (S)-3-[4-(2-tert-Butyl-5-methyl-oxazol-4-ylmethoxy)-2-methoxy-phenyl]-2-ethoxy-propionic acid In analogy to the procedure described in example 46 d], (S)-3-[4-(2-tert-butyl-5-methyl-oxazol-4-ylmethoxy)-2-methoxy-phenyl]-2-ethoxy-propionic acid methyl ester was treated with LiOH to obtain (S)-3-[4-(2-tert-butyl-5-methyl-oxazol-4-ylmethoxy)-2-methoxy-phenyl]-2-ethoxy-propionic acid as colorless liquid.

MS: 414.2 $(M+Na)^+$, 392.2 $(M+H)^+$, 340.5, 267.2, 241.2, 195.3, 152.2.

Example 51 a] 4-Benzyloxy-2,6-dimethyl-benzaldehyde

In analogy to the procedure described in example 48 a], 4-hydroxy-2,6-dimethyl-benzaldehyde was reacted with benzyl bromide in the presence of potassium carbonate to yield 4-benzyloxy-2,6-dimethyl-benzaldehyde as orange liquid.

MS: 241.2 $(M+H)^+$, 181.0.

b] (S)-4-Benzyl-3-[(2S,3R)-3-(4-benzyloxy-2,6-dimethyl-phenyl)-2-ethoxy-3-hydroxy-propionyl]-oxazolidin-2-one In analogy to the procedure described in example 48 d], (S)-4-benzyl-3-ethoxyacetyl-oxazolidin-2-one (for the preparation of (S)-4-benzyl-3-ethoxyacetyl-oxazolidin-2-one see: D. Haigh, H. C. Birrell, B. C. C. Cantello, D. S. Eggleston, R. C. Haltiwanger, R. M. Hindley, A. Ramaswamy, N.C. Stevens, *Tetrahedron: Asymmetry* 1999, 10, 1353–1367) was reacted with 4-benzyloxy-2,6-dimethyl-benzaldehyde in the presence of triethylamine and di-n-butylboron triflate to give (S)-4-benzyl-3-[(2S,3R)-3-(4-benzyloxy-2,6-dimethyl-phenyl)-2-ethoxy-3-hydroxy-propionyl]-oxazolidin-2-one as colorless liquid. According to $^1$H-NMR spectroscopy, one of the four isomers is strongly predominating. The configuration was tentatively assigned as 2S,3R according to D. Haigh et al., *Tetrahedron: Asymmetry* 1999, 10, 1353–1367.

MS: 526.3 $(M+Na)^+$, 486.3, 425.3, 358.2, 309.1, 281.2, 253.1, 237.2, 178.2.

c] (2S,3R)-3-(4-Benzyloxy-2,6-dimethyl-phenyl)-2-ethoxy-3-hydroxy-propionic acid methyl ester In analogy to the procedure described in example 48 e], (S)-4-benzyl-3-[(2S,3R)-3-(4-benzyloxy-2,6-dimethyl-phenyl)-2-ethoxy-3-hydroxy-propionyl]-oxazolidin-2-one was treated with sodium methoxide in methanol to give (2S,3R)-3-(4-benzyloxy-2,6-dimethyl-phenyl)-2-ethoxy-3-hydroxy-propionic acid methyl ester as colorless liquid. According to $^1$H-NMR spectroscopy, one single diastereomer was obtained.

MS: 381.2 $(M+Na)^+$, 376.3 $(M+NH_4)^+$, 341.2, 313.2, 269.2, 213.3, 187.2.

d] (2S)-3-(4-Benzyloxy-2,6-dimethyl-phenyl)-2-ethoxy-propionic acid methyl ester In analogy to the procedure described in example 48 f], (2S,3R)-3-(4-benzyloxy-2,6-dimethyl-phenyl)-2-ethoxy-3-hydroxy-propionic acid methyl ester was treated with triethylsilane in trifluoroacetic acid to yield (2S)-3-(4-benzyloxy-2,6-dimethyl-phenyl)-2-ethoxy-propionic acid methyl ester as colorless liquid.

MS: 360.3 $(M+NH_4)^+$, 284.1, 269.2, 201.1, 163.3.

e] (2S)-2-Ethoxy-3-(4-hydroxy-2,6-dimethyl-phenyl)-propionic acid methyl ester

In analogy to the procedure described in example 46 b], (2S)-3-(4-benzyloxy-2,6-dimethyl-phenyl)-2-ethoxy-propionic acid methyl ester was hydrogenated over 10% palladium on charcoal to give (2S)-2-ethoxy-3-(4-hydroxy-2,6-dimethyl-phenyl)-propionic acid methyl ester as colorless liquid.

MS: 275.2 (M+Na)$^+$, 270.3 (M+NH$_4$)$^+$, 253.3 (M+H)$^+$, 207.2, 165.3.

f] (S)-3-[4-(2-tert-Butyl-5-methyl-oxazol-4-ylmethoxy)-2,6-dimethyl-phenyl]-2-ethoxy-propionic acid methyl ester In analogy to the procedure described in example 46 c], (2S)-2-ethoxy-3-(4-hydroxy-2,6-dimethyl-phenyl)-propionic acid methyl ester was reacted with 2-tert-butyl-4-chloromethyl-5-methyl-oxazole (example 1, step b]) in the presence of cesium carbonate and potassium iodide to yield (S)-3-[4-(2-tert-butyl-5-methyl-oxazol-4-ylmethoxy)-2,6-dimethyl-phenyl]-2-ethoxy-propionic acid methyl ester as colorless liquid.

MS: 426.4 (M+Na)$^+$, 404.4 (M+H)$^+$, 300.3, 193.3, 152.2.

g] (S)-3-[4-(2-tert-Butyl-5-methyl-oxazol-4-ylmethoxy)-2,6-dimethyl-phenyl]-2-ethoxy-propionic acid In analogy to the procedure described in example 46 d], (S)-3-[4-(2-tert-butyl-5-methyl-oxazol-4-ylmethoxy)-2,6-dimethyl-phenyl]-2-ethoxy-propionic acid methyl ester was treated with LiOH to obtain (S)-3-[4-(2-tert-butyl-5-methyl-oxazol-4-ylmethoxy)-2,6-dimethyl-phenyl]-2-ethoxy-propionic acid as colorless solid.

MS: 388.1 (M–H)$^-$, 342.1, 320.9, 252.8, 236.8, 209.3, 190.6, 163.4.

Example 52 a] (S)-3-{4-[2-(2-tert-Butyl-5-methyl-oxazol-4-yl)-ethoxy]-2,6-dimethyl-phenyl}-2-ethoxy-propionic acid methyl ester In analogy to the Mitsunobu-procedure described in example 1, step f], (2S)-2-ethoxy-3-(4-hydroxy-2,6-dimethyl-phenyl)-propionic acid methyl ester (example 51 e]) was reacted with 2-(2-tert-butyl-5-methyl-oxazol-4-yl)-ethanol (example 1, step e])) in the presence of tributylphosphine and N,N,N',N'-tetramethyl azodicarboxamide to yield (S)-3-{4-[2-(2-tert-butyl-5-methyl-oxazol-4-yl)-ethoxy]-2,6-dimethyl-phenyl}-2-ethoxy-propionic acid methyl ester as colorless oil.

MS: 418.4 (M+H)$^+$.

b] (S)-3-{4-[2-(2-tert-Butyl-5-methyl-oxazol-4-yl)-ethoxy-2,6-dimethyl-phenyl}-2-ethoxy-propionic acid In analogy to the procedure described in example 46 d], (S)-3-{4-[2-(2-tert-butyl-5-methyl-oxazol-4-yl)-ethoxy]-2,6-dimethyl-phenyl}-2-ethoxy-propionic acid methyl ester was treated with LiOH to obtain (S)-3-{4-[2-(2-tert-butyl-5-methyl-oxazol-4-yl)-ethoxy]-2,6-dimethyl-phenyl}-2-ethoxy-propionic acid as colorless liquid.

MS: 402.3 (M–H)$^-$, 356.1, 293.0, 247.0.

Example 53

[rac]-3-{4-[3-(2-tert-Butyl-5-ethyl-oxazol-4-yl)-propoxy]-benzo[b]thiophen-7-yl}-2-ethoxy-propionic acid was prepared in analogy to example 35, but using for the Mitsunobu-coupling 3-(2-tert-butyl-5-ethyl-oxazol-4-yl)-propan-1-ol instead of 2-(2-tert-butyl-5-ethyl-oxazol-4-yl)-ethanol as white solid of mp. 94–95°.

MS: 458.3 (M–H)$^-$.

The former intermediate was prepared from 4-allyl-2-tert-butyl-5-ethyl-oxazole, whose preparation is detailed in example 35 e], as follows:

0.693 g of 4-allyl-2-tert-butyl-5-ethyl-oxazole (3.585 mmol) was dissolved under an argon atmosphere in 10 ml of abs. THF and treated at 0° with 3 eq. of 9-BBN (0.5 M, hexane). After 3 h at ambient temperature, when TLC indicated the absence of starting material, 20.9 ml of 30% H$_2$O$_2$ and 10.3 ml of 3N NaOH was added dropwise, but simultaneously. After cessation of the strongly exothermic reaction, the mixture was diluted with AcOEt and water, the layers separated, the aqueous phase reextracted with AcOEt, and the combined organic phases washed with water. Drying over sodium sulfate and evaporation of the solvents, followed by flash chromatography (SiO$_2$, hexane/AcOEt=1/1) afforded 0.400 g of 3-(2-tert-butyl-5-ethyl-oxazol-4-yl)-propan-1-ol as colorless oil.

MS: 212.0 (M+H)$^+$.

Example 54

[rac]-3-{4-[3-(2-tert-Butyl-5-methyl-oxazol-4-yl)-propoxy]-benzo[b]thiophen-7-yl}-2-ethoxy-propionic acid was prepared in analogy to example 53, but using for the Mitsunobu-coupling 3-(2-tert-butyl-5-methyl-oxazol-4-yl)-propan-1-ol instead of 3-(2-tert-butyl-5-ethyl-oxazol-4-yl)-propan-1-ol as off-white solid of mp. 125–26°.

MS: 444.3 (M–H)—.

Example 55

[rac]-3-{4-[3-(2-tert-Butyl-5-methyl-oxazol-4-yl)-propoxy]-naphthalen-1-yl}-2-isopropoxy-propionic acid was prepared in analogy to example 11, but using for the Mitsunobu-coupling 3-(2-tert-butyl-5-methyl-oxazol-4-yl)-propan-1-ol instead of 2-(2-tert-butyl-5-methyl-oxazol-4-yl)-ethanol as white solid of mp. 118–19°.

MS: 452.3 (M–H)$^-$.

Example 56

[rac]-3-{4-[3-(2-tert-Butyl-5-methyl-oxazol-4-yl)-propoxy]-naphthalen-1-yl}-2-ethoxy-propionic acid was prepared in analogy to example 55, but using in the Aldol-coupling ethyl ethoxyacetate instead of ethyl isopropoxyacetate as white solid of mp. 138–40°.

MS: 438.3 (M–H)$^-$.

Example 57

[rac]-3-{4-[3-(2-tert-Butyl-5-methyl-oxazol-4-yl)-propoxy]-naphthalen-1-yl}-2-propoxy-propionic acid was prepared in analogy to example 55, but using in the Aldol-coupling ethyl propoxyacetate instead of ethyl isopropoxyacetate as white solid of mp. 140–41°.

MS: 452.3 (M–H)$^-$.

Example 58

[rac]-3-{4-[3-(2-tert-Butyl-5-methyl-oxazol-4-yl)-propoxy]-benzo[b]thiophen-7-yl}-2-methoxy-propionic acid was prepared in analogy to example 54, but using in the Aldol-coupling ethyl methoxyacetate instead of ethyl ethoxyacetate as white solid of mp. 110–13°.

MS: 430.3 (M–H)$^-$.

Example 59

[rac]-2-Ethoxy-3-{4-[2-(2-isopropyl-5-methyl-oxazol-4-yl)-ethoxy]-naphthalen-1-yl}-propionic acid was prepared in analogy to example 12, but using for the Mitsunobu-coupling 2-(2-isopropyl-5-methyl-oxazol-4-yl)-ethanol instead of 2-(2-tert-butyl-5-methyl-oxazol-4-yl)-ethanol as colorless, viscous oil.

MS: 410.3 (M–H)$^-$.

The former intermediate can be prepared as follows:

a] Isobutyrylamino-acetic acid ethyl ester 10.00 g of glycine ethyl ester hydrochloride (71.6 mmol) and 21.97 ml of NEt$_3$ (2.2 eq.) were dissolved in 200 ml of CH$_2$Cl$_2$ and treated between 0° and 5° dropwise with 7.81 ml of isobutyryl chloride (1.05 eq.), dissolved in 50 ml of CH$_2$Cl$_2$. The reaction mixture was allowed to reach ambient temperature (2.5 h) and then quenched by carefully pouring onto crashed ice/HCl/AcOEt. Separation of the layers, additional extraction of the aqueous phase with AcOEt, washing with Na$_2$CO$_3$ and brine, drying of the combined organic phase over magnesium sulfate, and evaporation of the solvents, followed by flash chromatography (SiO$_2$, hexane/AcOEt=6/4) yielded 11.74 g of the title compound as colorless oil.

b] 2-Isobutyrylamino-pent-4-enoic acid ethyl ester 11.74 g of the above prepared isobutyrylamino-acetic acid ethyl ester (67.78 mmol) was dissolved in 250 ml of abs. THF and cooled down to –78°. 139 ml of 1M lithium hexamethyldisilazide in hexane (2.05 eq.) were added within 30 Min. via dropping funnel. After keeping the yellow suspension for additional 30 Min. at –78°, 6.021 ml of allyl bromide (1.05 eq.) was added and stirring continued for 15 Min. at the same temperature and for 30 Min. at 0°. Pouring of the homogeneous reaction mixture onto crashed ice/HCl, twofold extraction with AcOEt, twofold washing with water and brine, drying over magnesium sulfate, and evaporation of the solvents, followed by flash chromatography (SiO$_2$, hexane/AcOEt=7/3) afforded. 11.70 g of the title compound as pale-yellow oil.

MS: 214.3 (M+H)$^+$.

c] 2-Isobutyrylamino-pent-4-enoic acid 11.70 g of the above prepared 2-isobutyrylamino-pent-4-enoic acid ethyl ester (67.55 mmol) were dissolved in 110 ml of a 1:1 mixture of EtOH and THF and treated under cooling with an ice bath with 33.80 ml of 2N NaOH (2 eq.). After 2.5 h, the reaction mixture was poured onto crashed ice/AcOEt/HCl, the aqueous phase reextracted once more with AcOEt, the combined organic layers washed with water and brine, dried over magnesium sulfate, and evaporated to dryness. Crystallization from AcOEt/hexane afforded 7.95 g of the title product as white solid.

d] N-(1-Acetyl-but-3-enyl)-isobutyramide 7.77 g of the above synthesized 2-isobutyrylamino-pent-4-enoic acid (41.95 mmol) were dissolved in 36.5 ml of pyridine, treated with 19.83 ml of acetic anhydride (5 eq.), and heated to 100° for 1 h. After cooling, 28.3 ml of water were added and the mixture kept for 20 Min. at 90°. Careful pouring onto crashed ice/HCl, twofold extraction with AcOEt, washing with water and brine, drying over magnesium sulfate, and evaporation of the solvents, followed by flash chromatography (silica gel, hexane/AcOEt=1/1) left finally 6.63 g of the title compound as yellowish oil.

MS: 184.2 (M+H)$^+$.

e] 4-Allyl-2-isopropyl-5-methyl-oxazole 6.63 g of the above prepared N-(1-acetyl-but-3-enyl)-isobutyramide(33.61 mmol) were treated with 37 ml of trifluoroacetic acid (483 mmol) and 28.03 ml of trifluoroacetic anhydride (6 eq.) and kept for 3 h at 40°, when TLC indicated the disappearance of starting material. The reaction mixture was then poured onto crashed ice/NaHCO$_3$, the aqueous layer (pH ~8) extracted twice with AcOEt, washed with water and brine, dried over magnesium sulfate, and evaporated to dryness. Flash chromatography (SiO$_2$, hexane/AcOEt=92/8) yielded 3.92 g of the title compound as yellowish oil.

MS: 165.1 (M)$^+$.

f] 2-(2-Isopropyl-5-methyl-oxazol-4-yl)-ethanol 3.92 g of the above prepared 4-allyl-2-isopropyl-5-methyl-oxazole (23.7 mmol) were dissolved in 65 ml of THF and 27.3 ml of water. 2.58 ml of a 2.5% OsO$_4$ solution in tBuOH (0.01 eq.) and 10.8 g of NaIO$_4$ (2.13 eq.) were added, and the exothermic reaction allowed to proceed for 60 Min. The reaction mixture was then poured onto crashed ice, extracted twice with EtOEt, washed with water and brine, dried over magnesium sulfate, and evaporated to dryness to provide ~4 g of crude product. This was redissolved in 50 ml of EtOH and reduced by adding 1.346 g of NaBH$_4$ (1.5 eq.) at 0°. The cooling bath was then removed and the mixture allowed to reach ambient temperature. Standard work-up delivered after final purification by flash chromatography (SiO$_2$, hexane/AcOEt=7/3) 0.870 g of the title compound as yellowish oil, besides of 2.35 g of starting material in the less polar fractions.

MS: 169.1 (M)$^+$.

Example 60

[rac]-2-Isopropoxy-3-{4-[2-(2-isopropyl-5-methyl-oxazol-4-yl)-ethoxy]-naphthalen-1-yl}-propionic acid was prepared in analogy to example 59, but using in the Aldol-coupling ethyl isopropoxyacetate instead of ethyl ethoxyacetate as colorless oil.

MS: 424.3 (M–H)$^-$.

Example 61

[rac]-2-Ethoxy-3-{4-[3-(2-isopropyl-5-methyl-oxazol-4-yl)-propoxy]-benzo[b]thiophen-7-yl}-propionic acid was prepared in analogy to example 54, but using for the Mitsunobu-coupling 3-(2-isopropyl-5-methyl-oxazol-4-yl)-propan-1-ol instead of 3-(2-tert-butyl-5-methyl-oxazol-4-yl)-propan-1-ol, as colorless oil.

MS: 430.3 (M–H)$^-$.

Example 62

[rac]-2-Isopropoxy-3-{4-[3-(2-isopropyl-5-methyl-oxazol-4-yl)-propoxy]-benzo[b]thiophen-7-yl}-propionic acid was prepared in analogy to example 61, but using in the Aldol-coupling ethyl isopropoxyacetate instead of ethyl ethoxyacetate, as white crystals of mp. 125–26°.

MS: 446.2 (M+H)$^+$.

Example 63

[rac]-2-Ethoxy-3-{4-[2-(2-isopropyl-5-methyl-oxazol-4-yl)-ethoxy]-benzo[b]thiophen-7-yl}-propionic acid was prepared in analogy to example 59, but using for the Mitsunobu-coupling 4-hydroxy-benzo[b]thiophene-7-carbaldehyde instead of 4-hydroxy-naphthalene-1-carbaldehyde, as light yellow oil.

MS: 416.2 (M−H)⁻.

Example 64

[rac]-2-Isopropoxy-3-{4-[2-(2-isopropyl-5-methyl-oxazol-4-yl)-ethoxy]-benzo[b]thiophen-7-yl}-propionic acid was prepared in analogy to example 63, but using in the Aldol-coupling ethyl isopropoxyacetate instead of ethyl ethoxyacetate, as light yellow oil.

MS: 430.3 (M+H)⁺.

Example 65

[rac]-2-Ethoxy-3-{4-[3-(2-ethyl-5-methyl-oxazol-4-yl)-propoxy]-naphthalen-1-yl}-propionic acid was prepared in analogy to example 59, but starting the reaction sequence with propionyl chloride instead of isobutyryl chloride, and elaborating the terminal double bond via hydroboration with 9-BBN (as described in example 53) into a primary hydroxy group instead of oxidative cleavage with $OsO_4/NaBH_4$, as off-white solid of mp. 113–17°.

MS: 410.2 (M−H)⁻.

Example 66

[rac]-2-Ethoxy-3-{4-[2-(2-ethyl-5-methyl-oxazol-4-yl)-ethoxy]-benzo[b]thiophen-7-yl}-propionic acid was prepared in analogy to example 65, but elaborating the terminal double bond via oxidative cleavage with $OsO_4/NaBH_4$ instead of hydroboration with 9-BBN, as off-white solid of mp. 84–85°.

MS: 402.2 (M−H)⁻.

Example 67

[rac]-2-Ethoxy-3-(4-{3-[2-(1-ethyl-propyl)-5-methyl-oxazol-4-yl]-propoxy}-benzo[b]thiophen-7-yl)-propionic acid was prepared in analogy to example 59, but starting the reaction sequence with 2-ethyl-butyryl chloride instead of isobutyryl chloride, elaborating the terminal double bond via hydroboration with 9-BBN (as described in example 53) into a primary hydroxy group instead of oxidative cleavage with $OsO_4/NaBH_4$, and using for the Mitsunobu-coupling 4-hydroxy-benzo[b]thiophene-7-carbaldehyde instead of 4-hydroxy-naphthalene-1-carbaldehyde, as white solid of mp. 54–56°.

MS: 458.4 (M−H)⁻.

Example 68

[rac]-2-Ethoxy-3-(4-{2-[2-(1-ethyl-propyl)-5-methyl-oxazol-4-yl]-ethoxy}-benzo[b]thiophen-7-yl)-propionic acid was prepared in analogy to example 59, but starting the reaction sequence with 2-ethyl-butyryl chloride instead of isobutyryl chloride and using for the Mitsunobu-coupling 4-hydroxy-benzo[b]thiophene-7-carbaldehyde instead of 4-hydroxy-naphthalene-1-carbaldehyde, as white solid of mp. 120–21°.

MS: 446.2 (M+H)⁻.

Example A

Tablets containing the following ingredients can be manufactured in a conventional manner:

| Ingredients | Per tablet |
| --- | --- |
| Compound of formula (I) | 10.0–100.0 mg |
| Lactose | 125.0 mg |
| Maize starch | 75.0 mg |
| Talc | 4.0 mg |
| Magnesium stearate | 1.0 mg |

Example B

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

Example C

Injection solutions can have the following composition:

| | |
| --- | --- |
| Compound of formula (I) | 3.0 mg |
| Gelatine | 150.0 mg |
| Phenol | 4.7 mg |
| Sodium carbonate | to obtain a final pH of 7 |
| Water for injection solutions | ad 1.0 ml |

We claim:
1. A compound of formula (I)

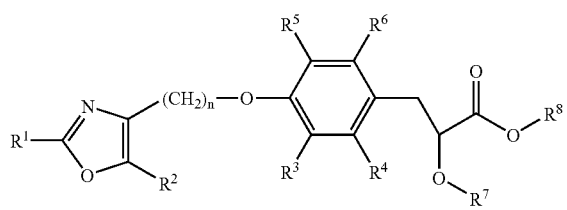

wherein
$R^1$ is alkyl, fluoro-lower-alkyl, cycloalkyl, bicyclic cycloalkyl, or tricyclic cycloalkyl;
$R^2$ is hydrogen, lower-alkyl, or fluoro-lower-alkyl;
$R^3$, $R^4$, $R^5$, and $R^6$ are independently selected from the group consisting of hydrogen, hydroxy, halogen, lower-alkyl, fluoro-lower-alkyl, hydroxy-lower-alkyl, loweralkoxy-lower-alkyl, lower-alkoxy, fluoro-lower-alkoxy, hydroxy-lower-alkoxy, lower-alkoxy-lower-alkoxy, and lower-alkenyl, wherein at least one of $R^3$, $R^4$, $R^5$, or $R^6$ is not hydrogen, or $R^3$ and $R^4$ are bonded to each other to form a ring together with the carbon atoms to which they are attached, and $R^3$ and $R^4$ together are —CH=CH—S—, —S—CH=CH—, —CH=CH—O—, —O—CH=CH—, —CH=CH—CH=CH—, —O—$(CH_2)_{2-3}$—, —$(CH_2)_{2-3}$—O—, or —$(CH_2)_{3-5}$—, and $R^5$ and $R^6$ are as defined above, $R^7$ is lower-alkyl, fluoro-lower-alkyl, lower-alkenyl, aryl, or aryl-lower-alkyl;

$R^8$ is hydrogen or lower-alkyl;

n is 1, 2 or 3;

or pharmaceutically acceptable salts or pharmaceutically acceptable esters thereof.

2. The compound according to claim 1, wherein $R^1$ is lower-alkyl, fluoro-lower-alkyl, cycloalkyl, bicyclic cycloalkyl, or tricyclic cycloalkyl.

3. The compound according to claim 1, wherein $R^1$ is lower-alkyl or cycloalkyl.

4. The compound according to claim 1, wherein $R^1$ is t-butyl, 2,2-dimethyl-propyl, cyclopropyl, or cyclohexyl.

5. The compound according to claim 1, wherein $R^2$ is lower-alkyl.

6. The compound according to claim 1, wherein $R^2$ is methyl.

7. The compound according to claim 6, wherein $R^1$ is t-butyl, 2,2-dimethyl-propyl, cyclopropyl, or cyclohexyl.

8. The compound according to claim 1, wherein $R^3$, $R^4$, $R^5$, and $R^6$ independently from each other are hydrogen, halogen, lower-alkyl, or lower-alkoxy, wherein at least one of $R^3$, $R^4$, $R^5$, or $R^6$ is not hydrogen; or $R^3$ and $R^4$ are bonded to each other to form a ring together with the carbon atoms to which they are attached, and $R^3$ and $R^4$ together are —CH=CH—S— or —CH=CH—CH=CH—, and $R^5$ and $R^6$ are hydrogen.

9. The compound according to claim 1, wherein $R^3$, $R^4$, $R^5$, and $R^6$ independently from each other are hydrogen or lower-alkyl, wherein at least one of $R^3$, $R^4$, $R^5$, or $R^6$ is not hydrogen.

10. The compound according to claim 1, wherein $R^3$, $R^4$, $R^5$, and $R^6$ independently from each other are hydrogen or methyl, wherein at least one of $R^3$, $R^4$, $R^5$, or $R^6$ is not hydrogen.

11. The compound according to claim 10, wherein $R^1$ is t-butyl, 2,2-dimethyl-propyl, cyclopropyl, or cyclohexyl.

12. The compound according to claim 11, wherein $R^2$ is methyl.

13. The compound according to claim 1, wherein $R^3$ and $R^4$ are bonded to each other to form a ring together with the carbon atoms to which they are attached, and $R^3$ and $R^4$ together are —CH=CH—S— or —CH=CH—CH=CH—, and $R^5$ and $R^6$ are hydrogen.

14. The compound according to claim 13, wherein $R^1$ is t-butyl, 2,2-dimethyl-propyl, cyclopropyl, or cyclohexyl.

15. The compound according to claim 14, wherein $R^2$ is methyl.

16. The compound according to claim 1, wherein $R^7$ is lower-alkyl or lower-alkenyl.

17. The compound according to claim 1, wherein $R^7$ is ethyl, n-propyl, i-propyl, or but-3-enyl.

18. The compound according to claim 17, wherein $R^1$ is t-butyl, 2,2-dimethyl-propyl, cyclopropyl, or cyclohexyl.

19. The compound according to claim 18, wherein $R^2$ is methyl.

20. The compound according to claim 19, wherein $R^3$, $R^4$, $R^5$, and $R^6$ independently from each other are hydrogen or methyl, wherein at least one of $R^3$, $R^4$, $R^5$, or $R^6$ is not hydrogen.

21. The compound according to claim 19, wherein $R^3$ and $R^4$ are bonded to each other to form a ring together with the carbon atoms to which they are attached, and $R^3$ and $R^4$ together are —CH=CH—S— or —CH=CH—CH=CH—, and $R^5$ and $R^6$ are hydrogen.

22. The compound according to claim 1, wherein $R^8$ is hydrogen.

23. The compound according to claim 22, wherein $R^1$ is t-butyl, 2,2-dimethyl-propyl, cyclopropyl, or cyclohexyl.

24. The compound according to claim 23, wherein $R^2$ is methyl.

25. The compound according to claim 24, wherein $R^3$, $R^4$, $R^5$, and $R^6$ independently from each other are hydrogen or methyl, wherein at least one of $R^3$, $R^4$, $R^5$, or $R^6$ is not hydrogen.

26. The compound according to claim 25, wherein $R^7$ is ethyl, n-propyl, i-propyl, or but-3-enyl.

27. The compound according to claim 24, wherein $R^3$ and $R^4$ are bonded to each other to form a ring together with the carbon atoms to which they are attached, and $R^3$ and $R^4$ together are —CH=CH—S— or —CH=CH—CH=CH—, and $R^5$ and $R^6$ are hydrogen.

28. The compound according to claim 27, wherein $R^7$ is ethyl, n-propyl, i-propyl, or but-3-enyl.

29. The compound according to claim 1, wherein n is 1 or 2.

30. The compound according to claim 1, wherein n is 2.

31. The compound according to claim 30, wherein $R^1$ is t-butyl, 2,2-dimethyl-propyl, cyclopropyl, or cyclohexyl.

32. The compound according to claim 31, wherein $R^2$ is methyl.

33. The compound according to claim 32, wherein $R^3$, $R^4$, $R^5$, and $R^6$ independently from each other are hydrogen or methyl, wherein at least one of $R^3$, $R^4$, $R^5$, or $R^6$ is not hydrogen.

34. The compound according to claim 33, wherein $R^7$ is ethyl, n-propyl, i-propyl, or but-3-enyl.

35. The compound according to claim 34, wherein $R^8$ is hydrogen.

36. The compound according to claim 32, wherein $R^3$ and $R^4$ are bonded to each other to form a ring together with the carbon atoms to which they are attached, and $R^3$ and $R^4$ together are —CH=CH—S— or —CH=CH—CH=CH—, and $R^5$ and $R^6$ are hydrogen.

37. The compound according to claim 36, wherein $R^7$ is ethyl, n-propyl, i-propyl, or but-3-enyl.

38. The compound according to claim 37, wherein $R^8$ is hydrogen.

39. A compound of formula (Ic)

$$\text{(Ic)}$$

wherein
- $R^1$ is alkyl, fluoro-lower-alkyl, cycloalkyl, bicyclic cycloalkyl, or tricyclic cycloalkyl;
- $R^2$ is hydrogen, lower-alkyl, or fluoro-lower-alkyl;
- $R^3$, $R^4$, $R^5$, and $R^6$ are independently selected from the group consisting of hydrogen, hydroxy, halogen, lower-alkyl, fluoro-lower-alkyl, hydroxy-lower-alkyl, lower-alkoxy-lower-alkyl, lower-alkoxy, fluoro-lower-alkoxy, hydroxy-lower-alkoxy, lower-alkoxy-lower-alkoxy, and lower-alkenyl, wherein at least one of $R^3$, $R^4$, $R^5$, or $R^6$ is not hydrogen, or
- $R^3$ and $R^4$ are bonded to each other to form a ring together with the carbon atoms to which they are attached, and $R^3$ and $R^4$ together are —CH=CH—S—, —S—CH=CH—, —CH=CH—O—, —O—CH=CH—, —CH=CH—CH=CH—, —O—(CH$_2$)$_{2-3}$—, —(CH$_2$)$_{2-3}$—O—, or —(CH$_2$)$_{3-5}$—, and $R^5$ and $R^6$ are as defined above,
- $R^7$ is lower-alkyl, fluoro-lower-alkyl, lower-alkenyl, aryl, or aryl-lower-alkyl;
- $R^8$ is hydrogen or lower-alkyl;
- n is 1, 2 or 3;

or pharmaceutically acceptable salts or pharmaceutically acceptable esters thereof.

40. The compound according to claim 39, wherein $R^1$ is t-butyl, 2,2-dimethyl-propyl, cyclopropyl, or cyclohexyl.

41. The compound according to claim 39, wherein $R^2$ is methyl.

42. The compound according to claim 39, wherein $R^3$, $R^4$, $R^5$, and $R^6$ independently from each other are hydrogen or methyl, wherein at least one of $R^3$, $R^4$, $R^5$, or $R^6$ is not hydrogen.

43. The compound according to claim 39, wherein $R^7$ is ethyl, n-propyl, i-propyl, or but-3-enyl.

44. The compound according to claim 39, wherein $R^8$ is hydrogen.

45. The compound according to claim 39, wherein $R^3$ and $R^4$ are bonded to each other to form a ring together with the carbon atoms to which they are attached, and $R^3$ and $R^4$ together are —CH=CH—S— or —CH=CH—CH=CH—, and $R^5$ and $R^6$ are hydrogen.

46. The compound according to claim 39, wherein $R^7$ is ethyl, n-propyl, i-propyl, or but-3-enyl.

47. The compound according to claim 39, wherein $R^8$ is hydrogen.

48. The compound according to claim 1, selected from the group consisting of
- (S)-3-{4-[2-(2-tert-Butyl-5-methyl-oxazol-4-yl)-ethoxy]-naphthalen-1-yl}-2-ethoxy-propionic acid,
- (S)-2-But-3-enyloxy-3-{4-[2-(2-tert-butyl-5-methyl-oxazol-4-yl)-ethoxy]-naphthalen 1-yl}-propionic acid,
- 3-{4-[2-(2-tert-Butyl-5-methyl-oxazol-4-yl)-ethoxy]-naphthalen-1-yl}-2-isopropoxy-propionic acid,
- 3-{4-[2-(2-Cyclohexyl-5-methyl-oxazol-4-yl)-ethoxy]-naphthalen-1-yl}-2-propoxy-propionic acid, and
- 3-(4-{2-[2-(2,2-Dimethyl-propyl)-5-methyl-oxazol-4-yl]-ethoxy}-naphthalen-1-yl)-2-propoxy-propionic acid, or pharmaceutically acceptable salts or pharmaceutically acceptable esters thereof.

49. The compound according to claim 1, selected from the group consisting of
- 3-{4-[2-(2-tert-Butyl-5-methyl-oxazol-4-yl)-ethoxy]-benzo[b]thiophen-7-yl}-2-isopropoxy-propionic acid,
- 3-{4-[2-(2-tert-Butyl-5-methyl-oxazol-4-yl)-ethoxy]-benzo[b]thiophen-7-yl}-2-ethoxy-propionic acid,
- 3-{4-[2-(2-Cyclopropyl-5-methyl-oxazol-4-yl)-ethoxy]-benzo[b]thiophen-7-yl}-2-propoxy-propionic acid, and
- 3-{4-[2-(2-Cyclopropyl-5-methyl-oxazol-4-yl)-ethoxy]-benzo[b]thiophen-7-yl}-2-ethoxy-propionic acid, or pharmaceutically acceptable salts or pharmaceutically acceptable esters thereof.

50. The compound according to claim 1, selected from the group consisting of
- 3-{4-[2-(2-tert-Butyl-5-methyl-oxazol-4-yl)-ethoxy]-3-methyl-phenyl}-2-isopropoxy-propionic acid, and
- [rac]-3-{4-[2-(2-tert-Butyl-5-methyl-oxazol-4-yl)-ethoxy]-2-methyl-phenyl}-2-ethoxy-propionic acid, or pharmaceutically acceptable salts or pharmaceutically acceptable esters thereof.

51. A process for the manufacture of the compound according to claim 1, which process comprises removing a protecting group in a compound of formula (II)

$$\text{(II)}$$

wherein PG is a protecting group.

52. A compound manufactured by the process according to claim 51.

53. A pharmaceutical composition comprising a compound according to claim 1, and a pharmaceutically acceptable carrier and/or adjuvant.

* * * * *